(12) United States Patent
Cowart et al.

(10) Patent No.: US 7,351,828 B2
(45) Date of Patent: Apr. 1, 2008

(54) BENZIMIDAZOLES THAT ARE USEFUL IN TREATING SEXUAL DYSFUNCTION

(75) Inventors: Marlon D. Cowart, Round Lake Beach, IL (US); Pramila A. Bhatia, Libertyville, IL (US); Jerome F. Daanen, Racine, WI (US); Andrew O. Stewart, Libertyville, IL (US); Meena V. Patel, Green Oaks, IL (US); Teodozyj Kolasa, Lake Villa, IL (US); Jorge D. Brioni, Vernon Hills, IL (US); Jeffrey Rohde, Evanston, IL (US)

(73) Assignee: Abbott Laboratories, Abbott Park, IL (US)

( * ) Notice: Subject to any disclaimer, the term of this patent is extended or adjusted under 35 U.S.C. 154(b) by 274 days.

(21) Appl. No.: 10/699,465

(22) Filed: Oct. 31, 2003

(65) Prior Publication Data

US 2004/0110766 A1 Jun. 10, 2004

Related U.S. Application Data

(62) Division of application No. 10/094,265, filed on Mar. 8, 2002, now Pat. No. 7,022,728.

(60) Provisional application No. 60/274,805, filed on Mar. 9, 2001, provisional application No. 60/296,078, filed on Jun. 5, 2001, provisional application No. 60/340,452, filed on Dec. 14, 2001.

(51) Int. Cl.
*C07D 401/04* (2006.01)
*C07D 403/04* (2006.01)

(52) U.S. Cl. .................. 544/295; 544/364; 544/370
(58) Field of Classification Search .............. 544/295, 544/364, 370
See application file for complete search history.

(56) References Cited

U.S. PATENT DOCUMENTS

| | | | |
|---|---|---|---|
| 3,362,956 A | 1/1968 | Archer | |
| 3,472,854 A | 10/1969 | Archer | |
| 5,714,498 A | 2/1998 | Kulagowski et al. | |
| 5,714,854 A | 2/1998 | Mizuta et al. | |
| 5,792,768 A | 8/1998 | Kulagowski et al. | |
| 6,960,589 B2 * | 11/2005 | Cowart et al. ......... | 514/252.14 |
| 2002/0169166 A1 * | 11/2002 | Cowart et al. ......... | 514/252.19 |
| 2003/0008878 A1 * | 1/2003 | Cowart et al. ......... | 514/252.19 |

FOREIGN PATENT DOCUMENTS

| | | |
|---|---|---|
| EP | 0 468 884 | 7/1991 |
| EP | 0 882 718 | 12/1998 |
| ES | 2 154 605 | 9/1999 |
| WO | 98/31368 | 7/1998 |
| WO | 00/23056 | 4/2000 |
| WO | 02/88093 | 11/2002 |

OTHER PUBLICATIONS

Sule et al. Chemical Abstracts, vol. 90 No. 204028 (1979).*
Sule et al. Bull Haff Instt, vol. 6, pp. 62-64 (1978).*
Andersson, K. et al., "Physiology of penile erection," Physiol. Rev. 75:191-236, 1995.
Bendele, A.M. et al., "Anti-Inflammatory Activity of Pergolide, a Dopamine Receptor Agonist," Journal of Pharmacology and Experimental Therapeutics 259(1):169-175 (1991).
Berge, S.M. et al., J. Pharmaceutical Sciences 66:1et seq (1977).
Chen, F.F. et al., "Effects of dopamine, Apomorphine, -Hydroxybutyric Acid, Haloperidol and Pimozide on Reflex Bradycardia in Rats," Journal of Pharmacology and Experimental Therapeutics 214(2):427-432 (1980).
DeGroat, W. et al., "Neural Control of Penile Erection, in : Nervous control of urogenital system," Hardwood Academic Publishers, Chur, Switzerland, vol. 3 (ed. Maggi, C.):467-524 (1993).
Dula, E. et al., "Efficacy and safety of fixed-dose and dose-optimization regimens of sublingual apomorphine versus placebo in men with erectile dysfunction," Urology 56:130-135 (2000).
Hahn, R.A. et al., "Primate Cardiovascular Responses Mediated by Dopamine Receptors: Effects of N, N-di-n-Propyldopamine and LY171555," Journal of Pharmacology and Experimental therapeutics 229(1):132-138 (1984).
Harris, M. C. et al., "Sequential N-Arylation of Primary Amines as a Route to Alkyldiarylamines," J. Org. Chem. 64:6019-6022 (1999).
Hrib, N. J., et al., "The dopamine $D_4$ receptor: a controversial therapeutic target," Drugs of the Future 2000 25(6):587-611.
Koch, V. et al., "Chemistry of 3-Hydroxypyridien part 2: Synthesis of 5,6-Dihalo-3hydroypyridines," Synthesis 499-501 (1990).
Lissoni, et al., "Efficacy of bromocriptine in the treatment of metastatic breast cancer- and prostate cancer-related hyperprolactinemia," Neuroendocrinology Letters ISSN 21:405-408 (2000).

(Continued)

Primary Examiner—Emily Bernhardt
(74) Attorney, Agent, or Firm—Gabryleda Ferrari Dileo

(57) ABSTRACT

The present invention relates to the use of compounds of formula (I)

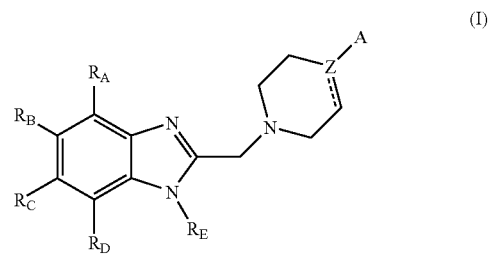

for the treatment of sexual dysfunction and to compositions containing compounds of formula (I) for the treatment of sexual dysfunction.

7 Claims, No Drawings

OTHER PUBLICATIONS

Lynch, J.K. et al., "Efficient asymmetric synthesis of ABT-594; a potent, orally effective analgesic," Tetrahedron: Asymmetry 9:2791-2794 (1998).

Melis, M et al., "Dopamine and Sexual Behavior," Neurosience and Biobehavioral Reviews, 19(1):193-35 (1995).

Milligan, G. et al., "Chimaeric G proteins: their potential use in drug discovery," Trends Pharmacol Sci 20:118-124 (1998).

Missale, C. et al. "Dopamine receptors: from structure to function," Pl•ysiol Rev 78:189-225 (1998).

Morales, A. et al., "Oral and Topical Treatment of Erectile Dysfunction: present and future," Urologic Clinics of North America, vol. 22:879-886 (1995).

Moreland, RB, et al., "Prospectives for Pharmacotherapy of Male Erectile Dysfunction," Curr Opinion CPNS Invest Drugs, 2:283-302 (2000).

Padma-Nathan, H. et al., "Efficacy and safety of apomorphine SL vs. placebo for male erectile dysfunction," Urology 161:214 (abstract 821) (1999).

Primus, R. et al., "Localization and characterization of dopamine $D_4$ binding sites in rat and human brain by use of the novel $D_4$ receptor-selective ligand [$^3$H]NGD 94-1," J. Pharmacol Exp. Ther 282:1020-1027 (1997).

Sule, D.P. et al., "Synthesis and Anthelmintic activity of 2-(N4-Substituted-N1-Piperazinyl) Methyl 5-(or 6)—substituted benzimidazoles," Bull. Haffkine Inst. 6(2):62-64 (1978).

Suzuki, M. et al., "$D_3$ dopamine receptor mRNA is widely express in human brain," Brian Res 779:58-74 (1998).

Vallone, D. et al., "Structure and function of dopamine receptors," Neurosci Biobehav. Rev. 24:125-132 (2000).

Wagaw, S. et al., "The Synthesis of Aminopyridines: A Method Employing Palladium-Catalyzed Carbon-Nitrogen Bond Formation," J. Org. Chem 61:7240-7241 (1996).

Yang B. et al., "Palladium-catalyzed amination of aryl halides and sulfonates," Journal of Organometallic Chemistry 576:125-146 (1999).

"IUPAC 1974 Recommendation for Section E, Fundamental Stereochemistry," Pure Appl. Chem. 45:13-30 (1976).

Bivalacqua et al., "Pharmacotherapy for erectile dysfunction," TIPS 21:484-489 (2000)

Shvedov et al., "Catalytic alkylation of amines with alcohols," Zhurnal Organicheskoi Khimii 6(9):1838-1840 (1970).

Pugsley et al., "The discovery of PD89211 and related compounds: selective dopamine D4 receptor antagonists," Progress in Neuro-Psychopharmacology & Biological Psyciatry 26(2):219-226 (2002).

* cited by examiner

BENZIMIDAZOLES THAT ARE USEFUL IN TREATING SEXUAL DYSFUNCTION

This is a divisional of U.S. patent application Ser. No. 10/094,265, filed Mar. 8, 2002, now U.S. Pat. No. 7,022,728; which claims priority from U.S. Provisional Application Ser. No. 60/274,805 filed on Mar. 9, 2001, from U.S. Provisional Application Ser. No. 60/296,078 filed on Jun. 5, 2001, and from U.S. Provisional Application Ser. No. 60/340,452 filed on Dec. 14, 2001.

TECHNICAL FIELD

The present invention relates to the use of benzimidazoles and compositions containing these compounds for the treatment of sexual dysfunction.

BACKGROUND OF THE INVENTION

Preclinical evidence indicates that dopamine (DA) plays a role in penile erection in mammals. Sexual stimulation can be initiated by sensory (erotic) information reaching the cerebral cortex in mammals. The cerebral cortex has extensive neuronal connections with limbic structures like the amygdala, as well as midbrain structures like the periaqueductal gray (PAG) and the hypothalamus. Two important nuclei in the hypothalamus are the medial preoptic area (MPOA) and the paraventricular nucleus (PVN). The MPOA and PVN nuclei play a critical role in sexual behavior as bilateral lesions of these areas completely eliminate male sexual behavior. The incerto-hypothalamic dopaminergic pathway that innervates the PVN and the MPOA nuclei has been associated with the pro-erectile effect of DA agents. Systemic administration of DA receptor agonists like apomorphine ((6aR) 5,6,6a,7-tetrahydro-6-methyl-4H-dibenzo[de,g]quinoline-10,11-diol), quinpirole and (−) 3-(3-hydroxyphenyl)-N-propylpiperidine (3-PPP) facilitate penile erection in rats, an effect blocked by haloperidol, a central DA antagonist. As the erectogenic effect can not be blocked by domperidone, a peripheral DA antagonist, it is believed that the pro-erectile effect of DA agonists is centrally mediated (Andersson K and Wagner G, Physiology of penile erection, Physiol Rev (1995) 75:191-236; deGroat W and Booth A, Neural Control of Penile Erection, in: Nervous control of urogenital system, Vol. 3, (ed. Maggi, C) (1993) p. 467-524, Hardwood Academic Publishers, Chur, Switzerland; and Moreland R B, Nakane M, Hsieh G and Brioni J D, Prospectives for Pharmacotherapy of Male Erectile Dysfunction, Curr Opinion CPNS Invest Drugs (2000) 2:283-302).

Clinical data also indicates that DA systems in the CNS play a role on the regulation of male sexual behavior as indicated by the sexual stimulatory effect of L-dopa in Parkinson's patients and by the pro-erectile effect of apomorphine in humans (Morales A, Geaton J, Johnston B and Adams M, Oral and Topical Treatment of Erectile Dysfunction: present and future, in: Urologic Clinics of North America, (1995) Vol. 22, p. 879-886; Padma-Nathan H, Auerbach S, Lewis R, Lewand M and Perdok R, Efficacy and safety of apomorphine SL vs. placebo for male erectile dysfunction (MED), Urology (1999) 161:214 (abstract 821); and Dula E, Keating W, Siami P, Edmonds A, O'Neil J, Efficacy and safety of fixed-dose and dose-optimization regimens of sublingual apomorphine versus placebo in men with erectile dysfunction, Urology (2000) 56:130-135).

DA receptors belong to a superfamily of protein receptors that signal across the cell membrane by coupling to intracellular GTP-binding proteins. Several G proteins have been identified (including Gs, Gq and Gi) that lead to specific intracellular events (Milligan G and Rees S, Chimaeric G proteins: their potential use in drug discovery, Trends Pharmacol Sci (1999) 20:118-124).

There are five known DA receptors which are classified into two groups, $D_1$-like and $D_2$-like. The $D_1$-like receptors include $D_1$ and $D_5$. The $D_2$-like receptors include $D_2$, $D_3$ and $D_4$ (Missale C, Nash S, Robinson S, Jaber M and Caron M, Dopamine receptors: from structure to function, Physiol Rev (1998) 78:189-225). The $D_1$-like family receptor subtypes are $G_s$-coupled and can activate adenylate cyclase. The $D_2$-like family receptor subtypes are $G_i$-coupled and they increase intracellular calcium level and inhibit adenylate cyclase.

The $D_1$-like family members are $G_s$-coupled receptors that can activate adenylate cyclase. The $D_1$ receptor is the most abundant and widespread DA receptor in the CNS both by mRNA expression and by immunohistochemical studies (Vallone D, Picetti R and Borreli E, Structure and function of dopamine receptors, Neurosci Biobehav Rev (2000) 24:125-132). It is found in the striatum, nucleus accumbens and olfactory tubercle as well as the limbic system, hypothalamus and thalamus. The $D_1$ receptor expression has been reported in the heart and kidney, and despite that the function of these peripheral $D_1$ receptors remains to be clarified, its role on the control of hemodynamic variables has been confirmed. The $D_5$ receptor, while having a higher affinity for DA than the $D_1$ receptor, is sparsely distributed in the CNS with no evidence of expression outside the CNS.

The $D_2$-like family members are $G_i$ coupled receptors that inhibit adenylate cyclase and increase intracellular calcium levels. The $D_2$ receptor is the most abundant of the $D_2$-like receptors and is located in brain areas such as the striatum and substantia nigra, and in peripheral areas such as the heart, pituitary gland and kidney. The $D_3$ receptor is found abundantly in the islands of Calleja with distinct cluster populations in the ventral striatum/nucleus accumbens regions, olfactory tubercle, dendate gyrus and striatal cortex (Suzuki M, Hurd Y, Sokoloff P, Schwartz J and Sedwall G, $D_3$dopamine receptor mRNA is widely express in human brain, Brain Res (1998) 779:58-74).

Expression of the $D_4$ receptor has been documented by in situ RNA hybridization and immunohistochemical studies. Recently, studies revealed that $D_4$ expression is highest in the entorhinal cortex, lateral septal nucleus, hippocampus and the medial preoptic area of the hypothalamus (Primus R, Thurkauf A, Xu J, Yevich E, Mcinerney S, Shaw K, Tallman J and Gallagher D, Localization and characterization of dopamine $D_4$ binding sites in rat and human brain by use of the novel $D_4$ receptor-selective ligand [$^3$H]NGD 94-1, J Pharmacol Exp Ther (1997) 282:1020-1027). Localization of $D_4$ is distinct from the distribution of $D_2$ in the brain, as D2 receptors are most abundant in striatal areas. The expression of $D_4$ receptors in the MPOA of the hypothalamus is of importance to the facilitation of penile erection in view of the role of the hypothalamus as an area of integration between the cortex and the spinal pathways. The participation of $D_4$ receptors in other CNS regions, thalamic, subthalamic and spinal can not be excluded.

U.S. Pat. No. 3,472,854 to Sterling discloses benzimidazole compounds useful as tranquilizers, sedatives, skeletal muscle relaxants, adrenolytic agents, hypothermic agents, anti-convulsants, hypotensive agents, and cardiovascular agents.

Sule et al. disclose 2-(N4-substituted-N1-piperazinyl)methyl-5-(or 6)-substituted benzimidazoles as potentially possessing anti-helmintic activity. In particular, the reference discloses the synthesis of 2-[(4-pyridin-2-ylpiperazin-1-yl)methyl]-1H-benzimidazole, although the compound was not considered effective as an anti-helmintic. Bull. Haffkine Inst., 1978, 6(2), 62-64.

U.S. Pat. No. 5,792,768 to Merck Sharp and Dome discloses benzimidazole compounds as $D_4$ antagonists and useful antipsychotic agents.

U.S. Pat. No. 5,714,498 to Merck Sharp and Dome discloses benzimidazole compounds as $D_4$ ligands for disorders of the dopamine system including schizophrenia, depression, nausea, Parkinson's disease, tardive dyskinesia, disorders of hypothalamio-pituitary function, upper gastrointestinal disorders, drug abuse, antipsychotic as well as cardiovascular disorders.

The present invention identifies a therapeutic use for benzimidazoles of formula (I) in the treatment of sexual dysfunction in mammals. More specifically, these compounds are useful in the treatment of sexual dysfunction including, but not limited to, male erectile dysfunction (MED).

SUMMARY OF THE INVENTION

The present invention relates to a method of treating sexual dysfunction in a mammal, in particular humans, comprising administering to said mammal a therapeutically effective amount of a compound of formula (I)

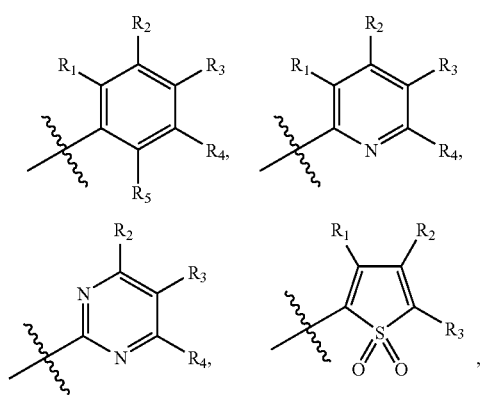

(I)

or a pharmaceutically acceptable salt, ester, amide, or prodrug thereof, wherein A is a selected from

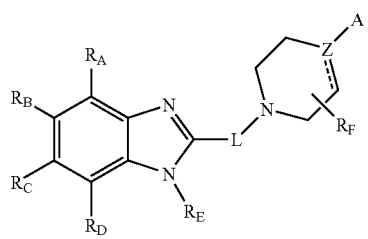

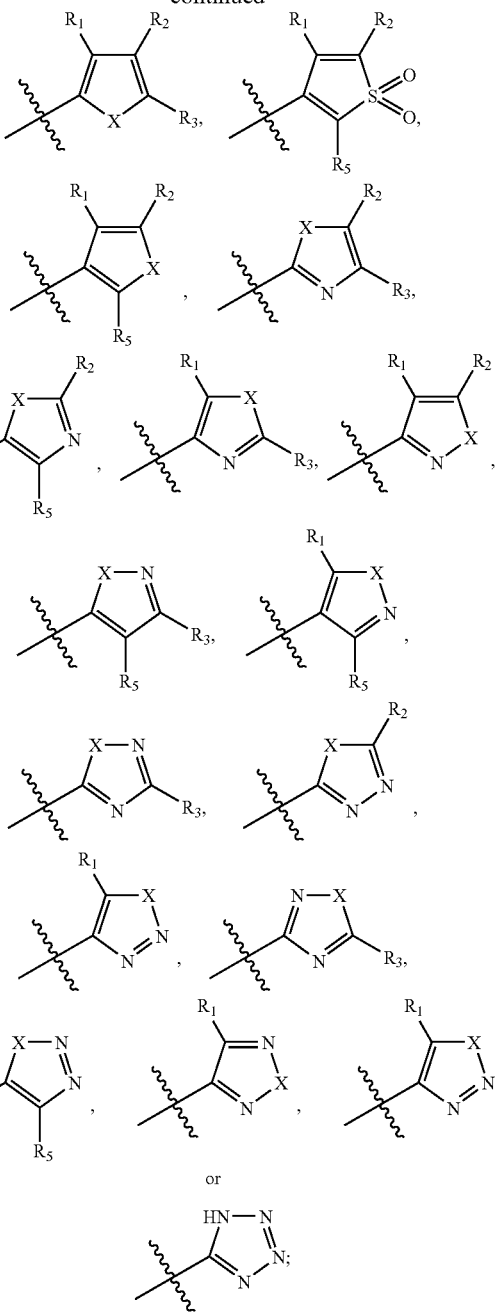

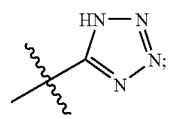

X is selected from NH, O or S;

L is selected from $CH_2$, $CH_2CH_2$, $CH_2CH_2CH_2$ or $CH_2CH_2CH_2CH_2$;

$R_1$, $R_2$, $R_3$, $R_4$ and $R_5$ are each independently selected from hydrogen, alkoxy, alkenyl, alkyl, alkylsulfinyl, alkylsulfonyl, alkylthio, alkynyl, alkoxycarbonyl, alkylcarbonyl, alkylcarbonyloxy, carboxy, cyano, formyl, halogen, haloalkoxy, haloalkyl, hydroxy, hydroxyalkyl, mercapto, nitro, $-NZ_1Z_2$, $(NZ_1Z_2)$carbonyl or $(NZ_1Z_2)$sulfonyl wherein $Z_1$ and $Z_2$ are each independently selected from the group consisting of hydrogen, alkyl, alkylcarbonyl, alkylsulfonyl or formyl;

$R_A$, $R_B$, $R_C$ and $R_D$ are each independently selected from hydrogen, alkoxy, alkenyl, alkyl, alkylsulfinyl, alkylsulfonyl, alkylthio, alkynyl, alkoxycarbonyl, alkylcarbonyl, alkylcarbonyloxy, carboxy, cyano, formyl, halogen, haloalkoxy, haloalkyl, hydroxy, hydroxyalkyl, mercapto, nitro, —$NZ_1Z_2$ or ($NZ_1Z_2$)carbonyl;

$R_E$ is selected from hydrogen, alkoxycarbonyl, alkyl, alkylcarbonyl, arylcarbonyl, cycloalkylcarbonyl, heterocyclecarbonyl or ($NZ_1Z_2$)carbonyl;

$R_F$ is selected from hydrogen or alkyl;

Z is selected from N, C or CH; and

— is a bond when Z is C and — is absent when Z is N or CH.

DETAILED DESCRIPTION OF THE INVENTION

All patents, patent applications, and literature references cited in the specification are herein incorporated by reference in their entirety.

In its principle embodiment, the present invention relates to a method of treating sexual dysfunction in a mammal, in particular humans, comprising administering to said mammal a therapeutically effective amount of a compound of formula (I)

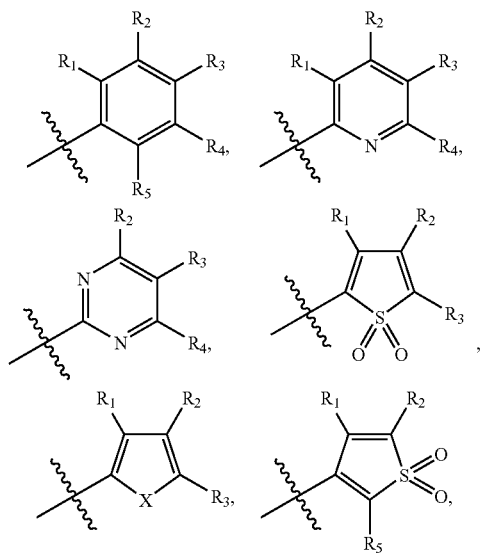

(I)

or a pharmaceutically acceptable salt, ester, amide, or prodrug thereof, wherein A is a selected from

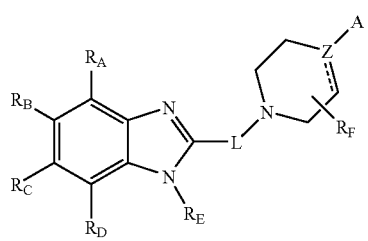

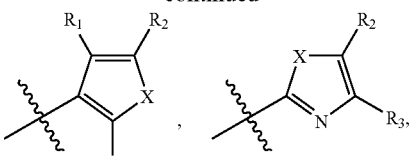

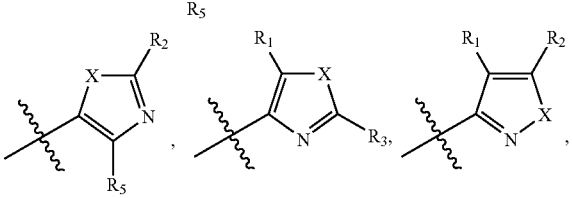

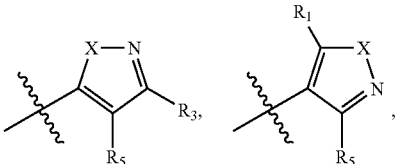

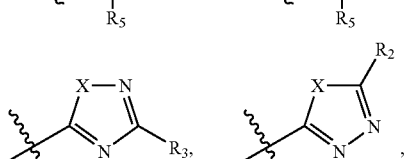

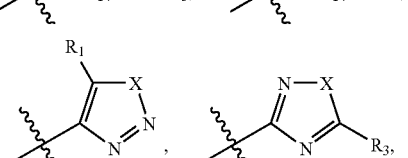

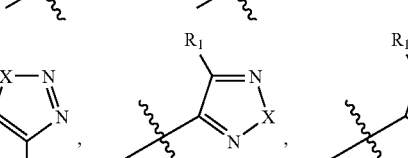

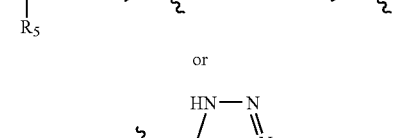

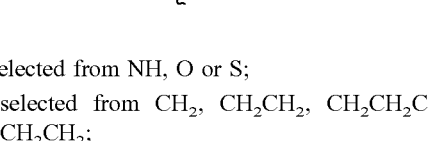

or

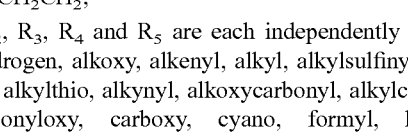

X is selected from NH, O or S;

L is selected from $CH_2$, $CH_2CH_2$, $CH_2CH_2CH_2$ or $CH_2CH_2CH_2CH_2$;

$R_1$, $R_2$, $R_3$, $R_4$ and $R_5$ are each independently selected from hydrogen, alkoxy, alkenyl, alkyl, alkylsulfinyl, alkylsulfonyl, alkylthio, alkynyl, alkoxycarbonyl, alkylcarbonyl, alkylcarbonyloxy, carboxy, cyano, formyl, halogen, haloalkoxy, haloalkyl, hydroxy, hydroxyalkyl, mercapto, nitro, —$NZ_1Z_2$ or ($NZ_1Z_2$)carbonyl wherein $Z_1$ and $Z_2$ are each independently selected from the group consisting of hydrogen, alkyl, alkylcarbonyl, alkylsulfonyl or formyl;

$R_A$, $R_B$, $R_C$ and $R_D$ are each independently selected from hydrogen, alkoxy, alkenyl, alkyl, alkylsulfinyl, alkylsulfonyl, alkylthio, alkynyl, alkoxycarbonyl, alkylcarbonyl, alkylcarbonyloxy, carboxy, cyano, formyl, halogen, haloalkoxy, haloalkyl, hydroxy, hydroxyalkyl, mercapto, nitro, —$NZ_1Z_2$ or ($NZ_1Z_2$)carbonyl;

$R_E$ is selected from hydrogen, alkoxycarbonyl, alkyl, alkylcarbonyl, arylcarbonyl, cycloalkylcarbonyl, heterocyclecarbonyl or $(NZ_1Z_2)$carbonyl;

$R_F$ is selected from hydrogen or alkyl;

Z is selected from N, C or CH; and

— is a bond when Z is C and — is absent when Z is N or CH.

In another embodiment, the present invention relates to a method of treating sexual dysfunction in a mammal comprising administering to said mammal a therapeutically effective amount of a compound of formula (I) wherein $R_A$, $R_B$, $R_C$ and $R_D$ are each independently selected from hydrogen or halogen; $R_E$ is hydrogen; Z is N; — is absent; and L and A are as defined in formula (I).

In another embodiment, the present invention relates to a method of treating sexual dysfunction in a mammal comprising administering to said mammal a therapeutically effective amount of a compound of formula (I) wherein $R_A$, $R_B$, $R_C$ and $R_D$ are each independently selected from hydrogen or halogen; $R_E$ is hydrogen; Z is N; — is absent; A is

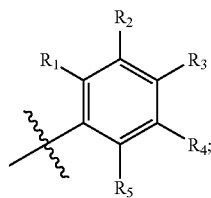

and L, $R_1$, $R_2$, $R_3$, $R_4$ and $R_5$ are as defined in formula (I).

In another embodiment, the present invention relates to a method of treating sexual dysfunction in a mammal comprising administering to said mammal a therapeutically effective amount of a compound of formula (I) wherein $R_A$, $R_B$, $R_C$ and $R_D$ are each independently selected from hydrogen or halogen; $R_E$ and $R_F$ are each hydrogen; L is $CH_2$; Z is N; — is absent; A is

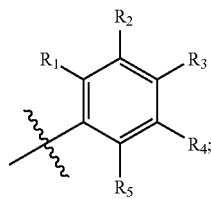

$R_2$, $R_3$ and $R_4$ are each hydrogen; and $R_1$ and $R_5$ are as defined in formula (I).

In another embodiment, the present invention relates to a method of treating sexual dysfunction in a mammal comprising administering to said mammal a therapeutically effective amount of a compound of formula (I) wherein $R_A$, $R_B$, $R_C$ and $R_D$ are each independently selected from hydrogen or halogen; $R_E$ and $R_F$ are each hydrogen; L is $CH_2$; Z is N; — is absent; A is

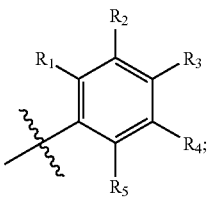

$R_1$, $R_2$, $R_4$ and $R_5$ are each hydrogen; and $R_3$ is as defined in formula (I).

In another embodiment, the present invention relates to a method of treating sexual dysfunction in a mammal comprising administering to said mammal a therapeutically effective amount of a compound of formula (I) wherein $R_A$, $R_B$, $R_C$ and $R_D$ are each independently selected from hydrogen or halogen; $R_E$ is hydrogen; Z is N; — is absent; A is

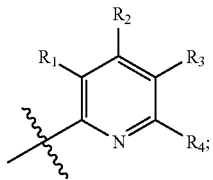

and L, $R_1$, $R_2$, $R_3$ and $R_4$ are as defined in formula (I).

In another embodiment, the present invention relates to a method of treating sexual dysfunction in a mammal comprising administering to said mammal a therapeutically effective amount of a compound of formula (I) wherein $R_A$, $R_B$, $R_C$ and $R_D$ are each independently selected from hydrogen or halogen; $R_E$ and $R_F$ are each hydrogen; L is $CH_2$; Z is N; — is absent; A is

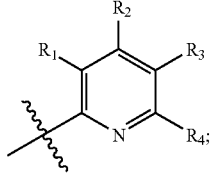

$R_2$, $R_3$ and $R_4$ are each hydrogen; and $R_1$ is as defined in formula (I).

In another embodiment, the present invention relates to a method of treating sexual dysfunction in a mammal comprising administering to said mammal a therapeutically effective amount of a compound of formula (I) wherein $R_A$, $R_B$, $R_C$, $R_D$, $R_E$ and $R_F$ are each hydrogen; L is $CH_2$; Z is N; — is absent; A is

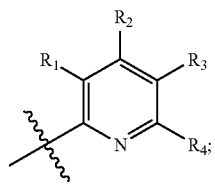

and R₁, R₂, R₃ and R₄ are each hydrogen.

In another embodiment, the present invention relates to a method of treating sexual dysfunction in a mammal comprising administering to said mammal a therapeutically effective amount of a compound of formula (I) wherein $R_A$, $R_B$, $R_C$ and $R_D$ are each independently selected from hydrogen or halogen; $R_E$ is hydrogen; $R_F$ is alkyl; L is $CH_2$; Z is N; — is absent; A is

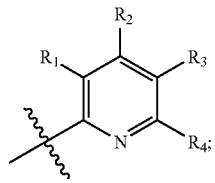

$R_2$, $R_3$ and $R_4$ are each hydrogen; and $R_1$ is as defined in formula (I).

In another embodiment, the present invention relates to a method of treating sexual dysfunction in a mammal comprising administering to said mammal a therapeutically effective amount of a compound of formula (I) wherein $R_A$, $R_B$, $R_C$ and $R_D$ are each independently selected from hydrogen or halogen; $R_E$ is hydrogen; $R_F$ is alkyl wherein said alkyl is methyl; L is $CH_2$; Z is N; — is absent; A is

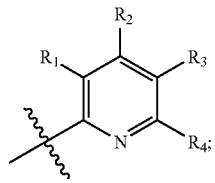

and R₁, R₂, R₃ and R₄ are each hydrogen.

In another embodiment, the present invention relates to a method of treating sexual dysfunction in a mammal comprising administering to said mammal a therapeutically effective amount of a compound of formula (I) wherein $R_A$, $R_B$, $R_C$ and $R_D$ are each independently selected from hydrogen or halogen; $R_E$ is hydrogen; Z is N; — is absent; A is

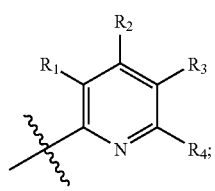

$R_1$, $R_2$, $R_3$ and $R_4$ are each independently selected from hydrogen or hydroxy; and L is as defined in formula (I).

In another embodiment, the present invention relates to a method of treating sexual dysfunction in a mammal comprising administering to said mammal a therapeutically effective amount of a compound of formula (I) wherein $R_A$, $R_B$, $R_C$ and $R_D$ are each independently selected from hydrogen or halogen; $R_E$ and $R_F$ are each hydrogen; L is $CH_2$; Z is N; — is absent; A is

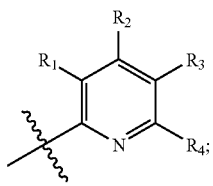

$R_1$, $R_2$ and $R_4$ are each hydrogen; and $R_3$ is hydroxy.

In another embodiment, the present invention relates to a method of treating sexual dysfunction in a mammal comprising administering to said mammal a therapeutically effective amount of a compound of formula (I) wherein $R_A$, $R_B$, $R_C$ and $R_D$ are each independently selected from hydrogen or halogen; $R_E$ is hydrogen; Z is N; — is absent; A is

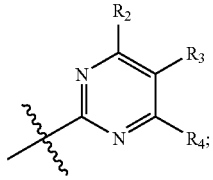

and L, $R_2$, $R_3$ and $R_4$ are as defined in formula (I).

In another embodiment, the present invention relates to a method of treating sexual dysfunction in a mammal comprising administering to said mammal a therapeutically effective amount of a compound of formula (I) wherein $R_A$, $R_B$, $R_C$ and $R_D$ are each independently selected from hydrogen or halogen; $R_E$ and $R_F$ are each hydrogen; L is $CH_2$; Z is N; — is absent; A is

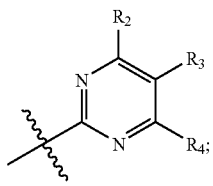

and $R_2$, $R_3$ and $R_4$ are each hydrogen.

In another embodiment, the present invention relates to a method of treating sexual dysfunction in a mammal comprising administering to said mammal a therapeutically effective amount of a compound of formula (I) wherein $R_A$, $R_B$, $R_C$, $R_D$, $R_E$ and $R_F$ are each hydrogen; L is $CH_2$; Z is N; — is absent; A is

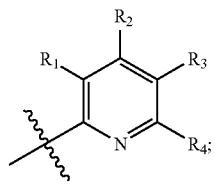

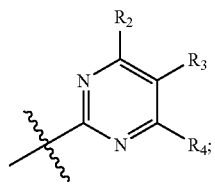

and $R_2$, $R_3$ and $R_4$ are each hydrogen.

In another embodiment, the present invention relates to a method of treating sexual dysfunction in a mammal comprising administering to said mammal a therapeutically effective amount of a compound of formula (I) wherein $R_A$, $R_B$, $R_C$ and $R_D$ are each independently selected from hydrogen or halogen; $R_E$ is hydrogen; Z is N; — is absent; A is

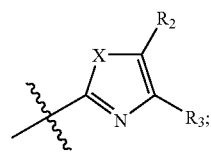

and X, L, $R_2$ and $R_3$ are as defined in formula (I).

In another embodiment, the present invention relates to a method of treating sexual dysfunction in a mammal comprising administering to said mammal a therapeutically effective amount of a compound of formula (I) wherein $R_A$, $R_B$, $R_C$ and $R_D$ are each independently selected from hydrogen or halogen; $R_E$ and $R_F$ are each hydrogen; L is $CH_2$; Z is N; — is absent; A is

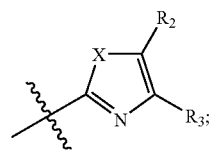

$R_2$ and $R_3$ are each hydrogen; and X is S.

In another embodiment, the present invention relates to a method of treating sexual dysfunction in a mammal comprising administering to said mammal a therapeutically effective amount of a compound of formula (I) wherein $R_A$, $R_B$, $R_C$ and $R_D$ are each independently selected from hydrogen and halogen; $R_E$ is selected from alkoxycarbonyl, alkylcarbonyl, alkyl, arylcarbonyl, cycloalkylcarbonyl, heterocyclecarbonyl or $(NZ_1Z_2)$carbonyl; Z is N; — is absent; A is

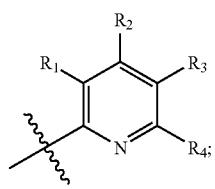

$Z_1$, $Z_2$, L, $R_1$, $R_2$, $R_3$ and $R_4$ are as defined in formula (I).

In another embodiment, the present invention relates to a method of treating sexual dysfunction in a mammal comprising administering to said mammal a therapeutically effective amount of a compound of formula (I) wherein $R_A$, $R_B$, $R_C$ and $R_D$ are each independently selected from hydrogen or halogen; $R_E$ is selected from alkoxycarbonyl, alkylcarbonyl, $(NZ_1Z_2)$carbonyl, or heterocyclecarbonyl wherein the heterocycle portion of said heterocyclecarbonyl is pyrrolidinyl; $R_F$ is hydrogen; L is $CH_2$; Z is N; — is absent; A is

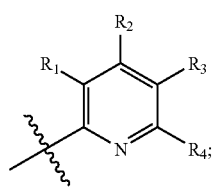

$R_2$, $R_3$ and $R_4$ are each hydrogen; and $Z_1$, $Z_2$ and $R_1$ are as defined in formula (I).

In another embodiment, the present invention relates to a method of treating sexual dysfunction in a mammal comprising administering to said mammal a therapeutically effective amount of a compound of formula (I) wherein $R_A$, $R_B$, $R_C$ and $R_D$ are each independently selected from hydrogen or halogen; $R_E$ is hydrogen; Z is CH; — is absent; A is

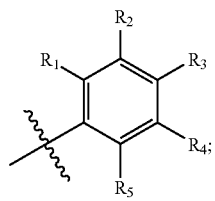

and L, $R_1$, $R_2$, $R_4$, $R_4$ and $R_5$ are as defined in formula (I).

In another embodiment, the present invention relates to a method of treating sexual dysfunction in a mammal comprising administering to said mammal a therapeutically effective amount of a compound of formula (I) wherein $R_A$, $R_B$, $R_C$ and $R_D$ are each independently selected from hydrogen or halogen; $R_E$ and $R_F$ are each hydrogen; L is $CH_2$; — is absent; Z is CH; A is

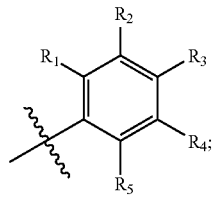

$R_2$, $R_3$ and $R_4$ are each hydrogen; and $R_1$ and $R_5$ are as defined in formula (I).

In another embodiment, the present invention relates to a method of treating sexual dysfunction in a mammal comprising administering to said mammal a therapeutically effective amount of a compound of formula (I) wherein $R_A$, $R_B$, $R_C$ and $R_D$ are each independently selected from hydrogen or halogen; $R_E$ is hydrogen; Z is CH; — is absent; A is

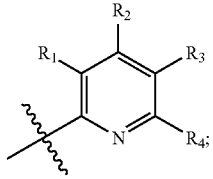

and L, $R_1$, $R_2$, $R_3$ and $R_4$ are as defined in formula (I).

In another embodiment, the present invention relates to a method of treating sexual dysfunction in a mammal comprising administering to said mammal a therapeutically effective amount of a compound of formula (I) wherein $R_A$, $R_B$, $R_C$ and $R_D$ are each independently selected from hydrogen or halogen; $R_E$ and $R_F$ are each hydrogen; L is CH$_2$; — is absent; Z is CH; A is

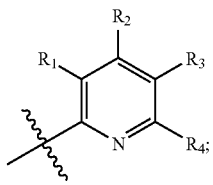

$R_2$, $R_3$ and $R_4$ are each hydrogen; and $R_1$ is as defined in formula (I).

In another embodiment, the present invention relates to a method of treating sexual dysfunction in a mammal comprising administering to said mammal a therapeutically effective amount of a compound of formula (I) wherein $R_A$, $R_B$, $R_C$ and $R_D$ are each independently selected from hydrogen or halogen; $R_E$ is hydrogen; Z is C; — is a bond; A is

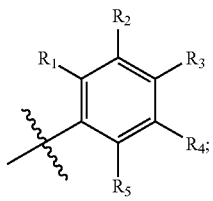

and L, $R_1$, $R_2$, $R_4$, $R_4$ and $R_5$ are as defined in formula (I).

In another embodiment, the present invention relates to a method of treating sexual dysfunction in a mammal comprising administering to said mammal a therapeutically effective amount of a compound of formula (I) wherein $R_A$, $R_B$, $R_C$ and $R_D$ are each independently selected from hydrogen or halogen; $R_E$ and $R_F$ are each hydrogen; L is CH$_2$; Z is C; — is a bond; A is

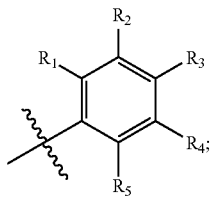

$R_2$, $R_3$ and $R_4$ are each hydrogen; and $R_1$ and $R_5$ are as defined in formula (I).

In another embodiment, the present invention relates to a method of treating sexual dysfunction including male sexual dysfunction and female sexual dysfunction in a human comprising administering to said human a therapeutically effective amount of a compound of formula (I) wherein said compound of formula (I) is selected from 2-{[4-(3-methylpyridin-2-yl)piperazin-1-yl]methyl}-1H-benzimidazole;

2-[4-(1H-benzimidazol-2-ylmethyl)piperazin-1-yl]nicotinonitrile;

5,7-dibromo-2-[(4-pyridin-2-ylpiperazin-1-yl)methyl]-1H-benzimidazole;

5-fluoro-2-[(4-pyridin-2-ylpiperazin-1-yl)methyl]-1H-benzimidazole;

2-{[4-(1,3-thiazol-2-yl)piperazin-1-yl]methyl}-1H-benzimidazole;

isobutyl 2-[(4-pyridin-2-ylpiperazin-1-yl)methyl]-1H-benzimidazole-1-carboxylate;

2-[(4-pyridin-2-ylpiperazin-1-yl)methyl]-1-(pyrrolidin-1-ylcarbonyl)-1H-benzimidazole;

N,N-dimethyl-2-[(4-pyridin-2-ylpiperazin-1-yl)methyl]-1H-benzimidazole-1-carboxamide;

2-[(4-phenylpiperazin-1-yl)methyl]-1H-benzimidazole;

2-[4-(1H-benzimidazol-2-ylmethyl)piperazin-1-yl]benzonitrile;

2-{[4-(2-chlorophenyl)piperazin-1-yl]methyl}-1H-benzimidazole;

2-{[4-(2-fluorophenyl)piperazin-1-yl]methyl}-1H-benzimidazole;

2-{[4-(2-nitrophenyl)piperazin-1-yl]methyl}-1H-benzimidazole;

2-{[4-(2-methoxyphenyl)piperazin-1-yl]methyl}-1H-benzimidazole;

4-[4-(1H-benzimidazol-2-ylmethyl)piperazin-1-yl]phenol;

2-({4-[2-(methylthio)phenyl]piperazin-1-yl}methyl)-1H-benzimidazole;

2-{[4-(2-ethoxyphenyl)piperazin-1-yl]methyl}-1H-benzimidazole;

2-[4-(1H-benzimidazol-2-ylmethyl)piperazin-1-yl]phenol;

2-{[4-(2-methoxyphenyl)piperidin-1-yl]methyl}-1H-benzimidazole;

2-[(4-pyridin-2-ylpiperidin-1-yl)methyl]-1H-benzimidazole;

2-[(4-phenyl-3,6-dihydropyridin-1(2H)-yl)methyl]-1H-benzimidazole;

2-{[4-(6-methylpyridin-2-yl)piperazin-1-yl]methyl}-1H-benzimidazole;

2-[(2-methyl-4-pyridin-2-ylpiperazin-1-yl)methyl]-1H-benzimidazole;

2-{[(2S)-2-methyl-4-pyridin-2-ylpiperazin-1-yl]methyl}-1H-benzimidazole;

2-{[(2R)-2-methyl-4-pyridin-2-ylpiperazin-1-yl]methyl}-1H-benzimidazole;

N-{2-[4-(1H-benzimidazol-2-ylmethyl)piperazin-1-yl]pyridin-3-yl}methanesulfonamide;

2-{[4-(3-fluoropyridin-2-yl)piperazin-1-yl]methyl}-1H-benzimidazole; or a pharmaceutically acceptable salt, ester, amide, or prodrug thereof.

In another embodiment, the present invention relates to a method of treating sexual dysfunction including male sexual dysfunction and female sexual dysfunction in a human comprising administering to said human a therapeutically effective amount of 2-[(4-pyridin-2-ylpiperazin-1-yl)methyl]-1H-benzimidazole or a pharmaceutically acceptable salt, ester, amide, or prodrug thereof.

In another embodiment, the present invention relates to a method of treating sexual dysfunction including male sexual dysfunction and female sexual dysfunction in a human comprising administering to said human a therapeutically effective amount of 2-[(4-pyridin-2-ylpiperazin-1-yl)methyl]-1H-benzimidazole bis((L)tartrate).

In another embodiment, the present invention relates to a method of treating sexual dysfunction including male sexual dysfunction and female sexual dysfunction in a human comprising administering to said human a therapeutically effective amount of 2-[(4-pyrimidin-2-ylpiperazin-1-yl)methyl]-1H-benzimidazole or a pharmaceutically acceptable salt, ester, amide, or prodrug thereof.

In another embodiment, the present invention relates to a method of treating sexual dysfunction including male sexual dysfunction and female sexual dysfunction in a human comprising administering to said human a therapeutically effective amount of 6-[4-(1H-benzimidazol-2-ylmethyl)piperazin-1-yl]pyridin-3-ol or a pharmaceutically acceptable salt, ester, amide, or prodrug thereof.

In another embodiment, the present invention relates to a method of treating sexual dysfunction including male sexual dysfunction and female sexual dysfunction in a human comprising administering to said human a therapeutically effective amount of a compound of formula (I) or a pharmaceutically acceptable salt, ester, amide, or prodrug thereof in combination with a pharmaceutically acceptable carrier.

In another embodiment, the present invention relates to a method of treating sexual dysfunction including male sexual dysfunction and female sexual dysfunction in a human comprising administering to said human a therapeutically effective amount of a compound of formula (I) wherein said compound of formula (I) is selected from 2-{[4-(3-methylpyridin-2-yl)piperazin-1-yl]methyl}-1H-benzimidazole;

2-[4-(1H-benzimidazol-2-ylmethyl)piperazin-1-yl]nicotinonitrile;

5,7-dibromo-2-[(4-pyridin-2-ylpiperazin-1-yl)methyl]-1H-benzimidazole;

5-fluoro-2-[(4-pyridin-2-ylpiperazin-1-yl)methyl]-1H-benzimidazole;

2-{[4-(1,3-thiazol-2-yl)piperazin-1-yl]methyl}-1H-benzimidazole;

isobutyl 2-[(4-pyridin-2-ylpiperazin-1-yl)methyl]-1H-benzimidazole-1-carboxylate;

2-[(4-pyridin-2-ylpiperazin-1-yl)methyl]-1-(pyrrolidin-1-ylcarbonyl)-1H-benzimidazole;

N,N-dimethyl-2-[(4-pyridin-2-ylpiperazin-1-yl)methyl]-1H-benzimidazole-1-carboxamide;

2-[(4-phenylpiperazin-1-yl)methyl]-1H-benzimidazole;

2-[4-(1H-benzimidazol-2-ylmethyl)piperazin-1-yl]benzonitrile;

2-{[4-(2-chlorophenyl)piperazin-1-yl]methyl}-1H-benzimidazole;

2-{[4-(2-fluorophenyl)piperazin-1-yl]methyl}-1H-benzimidazole;

2-{[4-(2-nitrophenyl)piperazin-1-yl]methyl}-1H-benzimidazole;

2-{[4-(2-methoxyphenyl)piperazin-1-yl]methyl}-1H-benzimidazole;

4-[4-(1H-benzimidazol-2-ylmethyl)piperazin-1-yl]phenol;

2-({4-[2-(methylthio)phenyl]piperazin-1-yl}methyl)-1H-benzimidazole;

2-{[4-(2-ethoxyphenyl)piperazin-1-yl]methyl}-1H-benzimidazole;

2-[4-(1H-benzimidazol-2-ylmethyl)piperazin-1-yl]phenol;

2-{[4-(2-methoxyphenyl)piperidin-1-yl]methyl}-1H-benzimidazole;

2-[(4-pyridin-2-ylpiperidin-1-yl)methyl]-1H-benzimidazole;

2-[(4-phenyl-3,6-dihydropyridin-1(2H)-yl)methyl]-1H-benzimidazole;

2-{[4-(6-methylpyridin-2-yl)piperazin-1-yl]methyl}-1H-benzimidazole;

2-[(2-methyl-4-pyridin-2-ylpiperazin-1-yl)methyl]-1H-benzimidazole;

2-{[(2S)-2-methyl-4-pyridin-2-ylpiperazin-1-yl]methyl}-1H-benzimidazole;

2-{[(2R)-2-methyl-4-pyridin-2-ylpiperazin-1-yl]methyl}-1H-benzimidazole;

N-{2-[4-(1H-benzimidazol-2-ylmethyl)piperazin-1-yl]pyridin-3-yl}methanesulfonamide;

2-{[4-(3-fluoropyridin-2-yl)piperazin-1-yl]methyl}-1H-benzimidazole; or a pharmaceutically acceptable salt, ester, amide, or prodrug thereof in combination with a pharmaceutically acceptable carrier.

In another embodiment, the present invention relates to a method of treating sexual dysfunction including male sexual dysfunction and female sexual dysfunction in a human comprising administering to said human a therapeutically effective amount of 2-[(4-pyridin-2-ylpiperazin-1-yl)methyl]-1H-benzimidazole or a pharmaceutically acceptable salt, ester, amide, or prodrug thereof in combination with a pharmaceutically acceptable carrier.

In another embodiment, the present invention relates to a method of treating sexual dysfunction including male sexual dysfunction and female sexual dysfunction in a human comprising administering to said human a therapeutically effective amount of 2-[(4-pyridin-2-ylpiperazin-1-yl)methyl]-1H-benzimidazole bis((L)tartrate) in combination with a pharmaceutically acceptable carrier.

In another embodiment, the present invention relates to a method of treating sexual dysfunction including male sexual dysfunction and female sexual dysfunction in a human comprising administering to said human a therapeutically effective amount of 2-[(4-pyrimidin-2-ylpiperazin-1-yl)methyl]-1H-benzimidazole or a pharmaceutically acceptable salt, ester, amide, or prodrug thereof in combination with a pharmaceutically acceptable carrier.

In another embodiment, the present invention relates to a method of treating sexual dysfunction including male sexual dysfunction and female sexual dysfunction in a human comprising administering to said human a therapeutically effective amount of 6-[4-(1H-benzimidazol-2-ylmethyl)piperazin-1-yl]pyridin-3-ol or a pharmaceutically acceptable salt, ester, amide, or prodrug thereof in combination with a pharmaceutically acceptable carrier.

In another embodiment, the present invention relates to a method of treating sexual dysfunction including male sexual dysfunction and female sexual dysfunction in a human comprising administering to said human a therapeutically effective amount of a compound of formula (I) or a pharmaceutically acceptable salt, ester, amide, or prodrug thereof in combination with a phosphodiesterase 5 inhibitor including, but not limited to, sildenafil or vardenafil.

In another embodiment, the present invention relates to a method of treating sexual dysfunction including male sexual dysfunction and female sexual dysfunction in a human comprising administering to said human a therapeutically effective amount of a compound of formula (I) wherein said compound of formula (I) is selected from 2-{[4-(3-methylpyridin-2-yl)piperazin-1-yl]methyl)-1H-benzimidazole;
2-[4-(1H-benzimidazol-2-ylmethyl)piperazin-1-yl]nicotinonitrile;
5,7-dibromo-2-[(4-pyridin-2-ylpiperazin-1-yl)methyl]-1H-benzimidazole;
5-fluoro-2-[(4-pyridin-2-ylpiperazin-1-yl)methyl]-1H-benzimidazole;
2-{[4-(1,3-thiazol-2-yl)piperazin-1-yl]methyl}-1H-benzimidazole;
isobutyl 2-[(4-pyridin-2-ylpiperazin-1-yl)methyl]-1H-benzimidazole-1-carboxylate;
2-[(4-pyridin-2-ylpiperazin-1-yl)methyl]-1-(pyrrolidin-1-ylcarbonyl)-1H-benzimidazole;
N,N-dimethyl-2-[(4-pyridin-2-ylpiperazin-1-yl)methyl]-1H-benzimidazole-1-carboxamide;
2-[(4-phenylpiperazin-1-yl)methyl]-1H-benzimidazole;
2-[4-(1H-benzimidazol-2-ylmethyl)piperazin-1-yl]benzonitrile;
2-{[4-(2-chlorophenyl)piperazin-1-yl]methyl}-1H-benzimidazole;
2-{[4-(2-fluorophenyl)piperazin-1-yl]methyl}-1H-benzimidazole;
2-{[4-(2-nitrophenyl)piperazin-1-yl]methyl}-1H-benzimidazole;
2-{[4-(2-methoxyphenyl)piperazin-1-yl]methyl}-1H-benzimidazole;
4-[4-(1H-benzimidazol-2-ylmethyl)piperazin-1-yl]phenol;
2-({4-[2-(methylthio)phenyl]piperazin-1-yl}methyl)-1H-benzimidazole;
2-{[4-(2-ethoxyphenyl)piperazin-1-yl]methyl}-1H-benzimidazole;
2-[4-(1H-benzimidazol-2-ylmethyl)piperazin-1-yl]phenol;
2-{[4-(2-methoxyphenyl)piperidin-1-yl]methyl}-1H-benzimidazole;
2-[(4-pyridin-2-ylpiperidin-1-yl)methyl]-1H-benzimidazole;
2-[(4-phenyl-3,6-dihydropyridin-1(2H)-yl)methyl]-1H-benzimidazole;
2-{[4-(6-methylpyridin-2-yl)piperazin-1-yl]methyl}-1H-benzimidazole;
2-[(2-methyl-4-pyridin-2-ylpiperazin-1-yl)methyl]-1H-benzimidazole;
2-{[(2S)-2-methyl-4-pyridin-2-ylpiperazin-1-yl]methyl}-1H-benzimidazole;
2-{[(2R)-2-methyl-4-pyridin-2-ylpiperazin-1-yl]methyl}-1H-benzimidazole;
N-{2-[4-(1H-benzimidazol-2-ylmethyl)piperazin-1-yl]pyridin-3-yl}methanesulfonamide;
2-{[4-(3-fluoropyridin-2-yl)piperazin-1-yl]methyl}-1H-benzimidazole; or a pharmaceutically acceptable salt, ester, amide, or prodrug thereof in combination with a phosphodiesterase 5 inhibitor including, but not limited to, sildenafil or vardenafil.

In another embodiment, the present invention relates to a method of treating sexual dysfunction including male sexual dysfunction and female sexual dysfunction in a human comprising administering to said human a therapeutically effective amount of 2-[(4-pyridin-2-ylpiperazin-1-yl)methyl]-1H-benzimidazole or a pharmaceutically acceptable salt, ester, amide, or prodrug thereof in combination with a phosphodiesterase 5 inhibitor including, but not limited to, sildenafil or vardenafil.

In another embodiment, the present invention relates to a method of treating sexual dysfunction including male sexual dysfunction and female sexual dysfunction in a human comprising administering to said human a therapeutically effective amount of 2-[(4-pyridin-2-ylpiperazin-1-yl)methyl]-1H-benzimidazole bis((L)tartrate in combination with a phosphodiesterase 5 inhibitor including, but not limited to, sildenafil or vardenafil.

In another embodiment, the present invention relates to a method of treating sexual dysfunction including male sexual dysfunction and female sexual dysfunction in a human comprising administering to said human a therapeutically effective amount of 2-[(4-pyrimidin-2-ylpiperazin-1-yl)methyl]-1H-benzimidazole or a pharmaceutically acceptable salt, ester, amide, or prodrug thereof in combination with a phosphodiesterase 5 inhibitor including, but not limited to, sildenafil or vardenafil.

In another embodiment, the present invention relates to a method of treating sexual dysfunction including male sexual dysfunction and female sexual dysfunction in a human comprising administering to said human a therapeutically effective amount of 6-[4-(1H-benzimidazol-2-ylmethyl)piperazin-1-yl]pyridin-3-ol or a pharmaceutically acceptable salt, ester, amide, or prodrug thereof in combination with a phosphodiesterase 5 inhibitor including, but not limited to, sildenafil or vardenafil.

In another embodiment, the present invention relates to a method of treating sexual dysfunction including male sexual dysfunction and female sexual dysfunction in a human comprising administering to said human a therapeutically effective amount of a compound of formula (I) or a pharmaceutically acceptable salt, ester, amide, or prodrug thereof in combination with an adrenergic receptor antagonist including, but not limited to, terazosin, prazosin or tamsulosin.

In another embodiment, the present invention relates to a method of treating sexual dysfunction including male sexual dysfunction and female sexual dysfunction in a human comprising administering to said human a therapeutically effective amount of a compound of formula (I) wherein said compound of formula (I) is selected from 2-{[4-(3-methylpyridin-2-yl)piperazin-1-yl]methyl}-1H-benzimidazole;
2-[4-(1H-benzimidazol-2-ylmethyl)piperazin-1-yl]nicotinonitrile;
5,7-dibromo-2-[(4-pyridin-2-ylpiperazin-1-yl)methyl]-1H-benzimidazole;
5-fluoro-2-[(4-pyridin-2-ylpiperazin-1-yl)methyl]-1H-benzimidazole;

2-{[4-(1,3-thiazol-2-yl)piperazin-1-yl]methyl}-1H-benzimidazole;
isobutyl 2-[(4-pyridin-2-ylpiperazin-1-yl)methyl]-1H-benzimidazole-1-carboxylate;
2-[(4-pyridin-2-ylpiperazin-1-yl)methyl]-1-(pyrrolidin-1-ylcarbonyl)-1H-benzimidazole;
N,N-dimethyl-2-[(4-pyridin-2-ylpiperazin-1-yl)methyl]-1H-benzimidazole-1-carboxamide;
2-[(4-phenylpiperazin-1-yl)methyl]-1H-benzimidazole;
2-[4-(1H-benzimidazol-2-ylmethyl)piperazin-1-yl]benzonitrile;
2-{[4-(2-chlorophenyl)piperazin-1-yl]methyl}-1H-benzimidazole;
2-{[4-(2-fluorophenyl)piperazin-1-yl]methyl}-1H-benzimidazole;
2-{[4-(2-nitrophenyl)piperazin-1-yl]methyl}-1H-benzimidazole;
2-{[4-(2-methoxyphenyl)piperazin-1-yl]methyl}-1H-benzimidazole;
4-[4-(1H-benzimidazol-2-ylmethyl)piperazin-1-yl]phenol;
2-({4-[2-(methylthio)phenyl]piperazin-1-yl}methyl)-1H-benzimidazole;
2-{[4-(2-ethoxyphenyl)piperazin-1-yl]methyl}-1H-benzimidazole;
2-[4-(1H-benzimidazol-2-ylmethyl)piperazin-1-yl]phenol;
2-{[4-(2-methoxyphenyl)piperidin-1-yl]methyl}-1H-benzimidazole;
2-[(4-pyridin-2-ylpiperidin-1-yl)methyl]-1H-benzimidazole;
2-[(4-phenyl-3,6-dihydropyridin-1(2H)-yl)methyl]-1H-benzimidazole;
2-{[4-(6-methylpyridin-2-yl)piperazin-1-yl]methyl}-1H-benzimidazole;
2-[(2-methyl-4-pyridin-2-ylpiperazin-1-yl)methyl]-1H-benzimidazole;
2-{[(2S)-2-methyl-4-pyridin-2-ylpiperazin-1-yl]methyl}-1H-benzimidazole;
2-{[(2R)-2-methyl-4-pyridin-2-ylpiperazin-1-yl]methyl}-1H-benzimidazole;
N-{2-[4-(1H-benzimidazol-2-ylmethyl)piperazin-1-yl]pyridin-3-yl}methanesulfonamide;
2-{[4-(3-fluoropyridin-2-yl)piperazin-1-yl]methyl}-1H-benzimidazole; or a pharmaceutically acceptable salt, ester, amide, or prodrug thereof in combination with an adrenergic receptor antagonist including, but not limited to, terazosin, prazosin or tamsulosin.

In another embodiment, the present invention relates to a method of treating sexual dysfunction including male sexual dysfunction and female sexual dysfunction in a human comprising administering to said human a therapeutically effective amount of 2-[(4-pyridin-2-ylpiperazin-1-yl)methyl]-1H-benzimidazole or a pharmaceutically acceptable salt, ester, amide, or prodrug thereof in combination with an adrenergic receptor antagonist including, but not limited to, terazosin, prazosin or tamsulosin.

In another embodiment, the present invention relates to a method of treating sexual dysfunction including male sexual dysfunction and female sexual dysfunction in a human comprising administering to said human a therapeutically effective amount of 2-[(4-pyridin-2-ylpiperazin-1-yl)methyl]-1H-benzimidazole bis((L)tartrate) in combination with an adrenergic receptor antagonist including, but not limited to, terazosin; prazosin or tamsulosin.

In another embodiment, the present invention relates to a method of treating sexual dysfunction including male sexual dysfunction and female sexual dysfunction in a human comprising administering to said human a therapeutically effective amount of 2-[(4-pyrimidin-2-ylpiperazin-1-yl)methyl]-1H-benzimidazole or a pharmaceutically acceptable salt, ester, amide, or prodrug thereof in combination with an adrenergic receptor antagonist including, but not limited to, terazosin, prazosin or tamsulosin.

In another embodiment, the present invention relates to a method of treating sexual dysfunction including male sexual dysfunction and female sexual dysfunction in a human comprising administering to said human a therapeutically effective amount of 6-[4-(1H-benzimidazol-2-ylmethyl)piperazin-1-yl]pyridin-3-ol or a pharmaceutically acceptable salt, ester, amide, or prodrug thereof in combination with an adrenergic receptor antagonist including, but not limited to, terazosin, prazosin or tamsulosin.

In another embodiment, the present invention relates to a method of treating sexual dysfunction including male sexual dysfunction and female sexual dysfunction in a human comprising administering to said human a therapeutically effective amount of a compound of formula (I) or a pharmaceutically acceptable salt, ester, amide, or prodrug thereof in combination with a dopamine agonist including, but not limited to, apomorphine.

In another embodiment, the present invention relates to a method of treating sexual dysfunction including male sexual dysfunction and female sexual dysfunction in a human comprising administering to said human a therapeutically effective amount of a compound of formula (I) wherein said compound of formula (I) is selected from
2-{[4-(3-methylpyridin-2-yl)piperazin-1-yl]methyl}-1H-benzimidazole;
2-[4-(1H-benzimidazol-2-ylmethyl)piperazin-1-yl]nicotinonitrile;
5,7-dibromo-2-[(4-pyridin-2-ylpiperazin-1-yl)methyl]-1H-benzimidazole;
5-fluoro-2-[(4-pyridin-2-yl)piperazin-1-yl)methyl]-1H-benzimidazole;
2-{[4-(1,3-thiazol-2-yl)piperazin-1-yl]methyl}-1H-benzimidazole;
isobutyl 2-[(4-pyridin-2-ylpiperazin-1-yl)methyl]-1H-benzimidazole-1-carboxylate;
2-[(4-pyridin-2-ylpiperazin-1-yl)methyl]-1-(pyrrolidin-1-ylcarbonyl)-1H-benzimidazole;
N,N-dimethyl-2-[(4-pyridin-2-ylpiperazin-1-yl)methyl]-1H-benzimidazole-1-carboxamide;
2-[(4-phenylpiperazin-1-yl)methyl]-1H-benzimidazole;
2-[4-(1H-benzimidazol-2-ylmethyl)piperazin-1-yl]benzonitrile;
2-{[4-(2-chlorophenyl)piperazin-1-yl]methyl}-1H-benzimidazole;
2-{[4-(2-fluorophenyl)piperazin-1-yl]methyl}-1H-benzimidazole;
2-{[4-(2-nitrophenyl)piperazin-1-yl]methyl}-1H-benzimidazole;
2-{[4-(2-methoxyphenyl)piperazin-1-yl]methyl}-1H-benzimidazole;
4-[4-(1H-benzimidazol-2-ylmethyl)piperazin-1-yl]phenol;
2-({4-[2-(methylthio)phenyl]piperazin-1-yl}methyl)-1H-benzimidazole;
2-{[4-(2-ethoxyphenyl)piperazin-1-yl]methyl}-1H-benzimidazole;
2-[4-(1H-benzimidazol-2-ylmethyl)piperazin-1-yl]phenol;
2-{[4-(2-methoxyphenyl)piperidin-1-yl]methyl}-1H-benzimidazole;
2-[(4-pyridin-2-ylpiperidin-1-yl)methyl]-1H-benzimidazole;

2-[(4-phenyl-3,6-dihydropyridin-1(2H)-yl)methyl]-1H-benzimidazole;
2-{[4-(6-methylpyridin-2-yl)piperazin-1-yl]methyl}-1H-benzimidazole;
2-[(2-methyl-4-pyridin-2-ylpiperazin-1-yl)methyl]-1H-benzimidazole;
2-{[(2S)-2-methyl-4-pyridin-2-ylpiperazin-1-yl]methyl}-1H-benzimidazole;
2-{[(2R)-2-methyl-4-pyridin-2-ylpiperazin-1-yl]methyl}-1H-benzimidazole;
N-{2-[4-(1H-benzimidazol-2-ylmethyl)piperazin-1-yl]pyridin-3-yl}methanesulfonamide;
2-{[4-(3-fluoropyridin-2-yl)piperazin-1-yl]methyl}-1H-benzimidazole; or a pharmaceutically acceptable salt, ester, amide, or prodrug thereof in combination with a dopamine agonist including, but not limited to, apomorphine.

In another embodiment, the present invention relates to a method of treating sexual dysfunction including male sexual dysfunction and female sexual dysfunction in a human comprising administering to said human a therapeutically effective amount of 2-[(4-pyridin-2-ylpiperazin-1-yl)methyl]-1H-benzimidazole or a pharmaceutically acceptable salt, ester, amide, or prodrug thereof in combination with a dopamine agonist including, but not limited to, apomorphine.

In another embodiment, the present invention relates to a method of treating sexual dysfunction including male sexual dysfunction and female sexual dysfunction in a human comprising administering to said human a therapeutically effective amount of 2-[(4-pyridin-2-ylpiperazin-1-yl)methyl]-1H-benzimidazole bis((L)tartrate) in combination with a dopamine agonist including, but not limited to, apomorphine.

In another embodiment, the present invention relates to a method of treating sexual dysfunction including male sexual dysfunction and female sexual dysfunction in a human comprising administering to said human a therapeutically effective amount of 2-[(4-pyrimidin-2-ylpiperazin-1-yl)methyl]-1H-benzimidazole or a pharmaceutically acceptable salt, ester, amide, or prodrug thereof in combination with a dopamine agonist including, but not limited to, apomorphine.

In another embodiment, the present invention relates to a method of treating sexual dysfunction including male sexual dysfunction and female sexual dysfunction in a human comprising administering to said human a therapeutically effective amount of 6-[4-(1H-benzimidazol-2-ylmethyl)piperazin-1-yl]pyridin-3-ol or a pharmaceutically acceptable salt, ester, amide, or prodrug thereof in combination with a dopamine agonist including, but not limited to, apomorphine.

In another embodiment, the present invention relates to a method of treating male erectile dysfunction in a male human comprising administering to said male human in need of such treatment a therapeutically effective amount of a compound of formula (I) or a pharmaceutically acceptable salt, ester, amide, or prodrug thereof.

In another embodiment, the present invention relates to a method of treating male erectile dysfunction in a male human comprising administering to said male human in need of such treatment a therapeutically effective amount of a compound of formula (I) wherein said compound of formula (I) is selected from 2-{[4-(3-methylpyridin-2-yl)piperazin-1-yl]methyl}-1H-benzimidazole;
2-[4-(1H-benzimidazol-2-ylmethyl)piperazin-1-yl]nicotinonitrile;
5,7-dibromo-2-[(4-pyridin-2-ylpiperazin-1-yl)methyl]-1H-benzimidazole;
5-fluoro-2-[(4-pyridin-2-ylpiperazin-1-yl)methyl]-1H-benzimidazole;
2-{[4-(1,3-thiazol-2-yl)piperazin-1-yl]methyl}-1H-benzimidazole;
isobutyl 2-[(4-pyridin-2-ylpiperazin-1-yl)methyl]-1H-benzimidazole-1-carboxylate;
2-[(4-pyridin-2-ylpiperazin-1-yl)methyl]-1-(pyrrolidin-1-ylcarbonyl)-1H-benzimidazole;
N,N-dimethyl-2-[(4-pyridin-2-ylpiperazin-1-yl)methyl]-1H-benzimidazole-1-carboxamide;
2-[(4-phenylpiperazin-1-yl)methyl]-1H-benzimidazole;
2-[4-(1H-benzimidazol-2-ylmethyl)piperazin-1-yl]benzonitrile;
2-{[4-(2-chlorophenyl)piperazin-1-yl]methyl}-1H-benzimidazole;
2-{[4-(2-fluorophenyl)piperazin-1-yl]methyl}-1H-benzimidazole;
2-{[4-(2-nitrophenyl)piperazin-1-yl]methyl}-1H-benzimidazole;
2-{[4-(2-methoxyphenyl)piperazin-1-yl]methyl}-1H-benzimidazole;
4-[4-(1H-benzimidazol-2-ylmethyl)piperazin-1-yl]phenol,
2-({4-[2-(methylthio)phenyl]piperazin-1-yl}methyl)-1H-benzimidazole;
2-{[4-(2-ethoxyphenyl)piperazin-1-yl]methyl}-1H-benzimidazole;
2-[4-(1H-benzimidazol-2-ylmethyl)piperazin-1-yl]phenol;
2-{[4-(2-methoxyphenyl)piperidin-1-yl]methyl}-1H-benzimidazole;
2-[(4-pyridin-2-ylpiperidin-1-yl)methyl]-1H-benzimidazole;
2-[(4-phenyl-3,6-dihydropyridin-1(2H)-yl)methyl]-1H-benzimidazole;
2-{[4-(6-methylpyridin-2-yl)piperazin-1-yl]methyl}-1H-benzimidazole;
2-[(2-methyl-4-pyridin-2-ylpiperazin-1-yl)methyl]-1H-benzimidazole;
2-{[(2S)-2-methyl-4-pyridin-2-ylpiperazin-1-yl]methyl}-1H-benzimidazole;
2-{[(2R)-2-methyl-4-pyridin-2-ylpiperazin-1-yl]methyl}-1H-benzimidazole;
N-{2-[4-(1H-benzimidazol-2-ylmethyl)piperazin-1-yl]pyridin-3-yl}methanesulfonamide;
2-{[4-(3-fluoropyridin-2-yl)piperazin-1-yl]methyl}-1H-benzimidazole; or a pharmaceutically acceptable salt, ester, amide, or prodrug thereof.

In another embodiment, the present invention relates to a method of treating male erectile dysfunction in a male human comprising administering to said male human in need of such treatment a therapeutically effective amount of 2-[(4-pyridin-2-ylpiperazin-1-yl)methyl]-1H-benzimidazole or a pharmaceutically acceptable salt, ester, amide, or prodrug thereof.

In another embodiment, the present invention relates to a method of treating male erectile dysfunction in a male human comprising administering to said male human in need of such treatment a therapeutically effective amount of 2-[(4-pyridin-2-ylpiperazin-1-yl)methyl]-1H-benzimidazole bis((L)tartrate).

In another embodiment, the present invention relates to a method of treating male erectile dysfunction in a male human comprising administering to said male human in need of such treatment a therapeutically effective amount of 2-[(4-pyrimidin-2-ylpiperazin-1-yl)methyl]-1H-benzimidazole or a pharmaceutically acceptable salt, ester, amide, or prodrug thereof.

In another embodiment, the present invention relates to a method of treating male erectile dysfunction in a male human comprising administering to said male human in need of such treatment a therapeutically effective amount of 6-[4-(1H-benzimidazol-2-ylmethyl)piperazin-1-yl]pyridin-3-ol or a pharmaceutically acceptable salt, ester, amide, or prodrug thereof.

In another embodiment, the present invention relates to a method of treating female anorgasmia, clitoral erectile insufficiency, vaginal engorgement, dyspareunia, or vaginismus in a female human comprising administering to said female human in need of such treatment a therapeutically effective amount of a compound of formula (I) or a pharmaceutically acceptable salt, ester, amide, or prodrug thereof.

In another embodiment, the present invention relates to a method of treating female anorgasmia, clitoral erectile insufficiency, vaginal engorgement, dyspareunia, or vaginismus in a female human comprising administering to said female human in need of such treatment a therapeutically effective amount of a compound of formula (I) wherein said compound of formula (I) is selected from 2-{[4-(3-methylpyridin-2-yl)piperazin-1-yl]methyl}-1H-benzimidazole;

2-[4-(1H-benzimidazol-2-ylmethyl)piperazin-1-yl]nicotinonitrile;

5,7-dibromo-2-[(4-pyridin-2-ylpiperazin-1-yl)methyl]-1H-benzimidazole;

5-fluoro-2-[(4-pyridin-2-ylpiperazin-1-yl)methyl]-1H-benzimidazole;

2-{[4-(1,3-thiazol-2-yl)piperazin-1-yl]methyl}-1H-benzimidazole;

isobutyl 2-[(4-pyridin-2-ylpiperazin-1-yl)methyl]-1H-benzimidazole-1-carboxylate;

2-[(4-pyridin-2-ylpiperazin-1-yl)methyl]-1-(pyrrolidin-1-ylcarbonyl)-1H-benzimidazole;

N,N-dimethyl-2-[(4-pyridin-2-ylpiperazin-1-yl)methyl]-1H-benzimidazole-1-carboxamide;

2-[(4-phenylpiperazin-1-yl)methyl]-1H-benzimidazole;

2-[4-(1H-benzimidazol-2-ylmethyl)piperazin-1-yl]benzonitrile;

2-{[4-(2-chlorophenyl)piperazin-1-yl]methyl}-1H-benzimidazole;

2-{[4-(2-fluorophenyl)piperazin-1-yl]methyl}-1H-benzimidazole;

2-{[4-(2-nitrophenyl)piperazin-1-yl]methyl}-1H-benzimidazole;

2-{[4-(2-methoxyphenyl)piperazin-1-yl]methyl}-1H-benzimidazole;

4-[4-(1H-benzimidazol-2-ylmethyl)piperazin-1-yl]phenol;

2-({4-[2-(methylthio)phenyl]piperazin-1-yl}methyl)-1H-benzimidazole;

2-{[4-(2-ethoxyphenyl)piperazin-1-yl]methyl}-1H-benzimidazole;

2-[4-(1H-benzimidazol-2-ylmethyl)piperazin-1-yl]phenol;

2-{[4-(2-methoxyphenyl)piperidin-1-yl]methyl}-1H-benzimidazole;

2-[(4-pyridin-2-ylpiperidin-1-yl)methyl]-1H-benzimidazole;

2-[(4-phenyl-3,6-dihydropyridin-1(2H)-yl)methyl]-1H-benzimidazole;

2-{[4-(6-methylpyridin-2-yl)piperazin-1-yl]methyl}-1H-benzimidazole;

2-[(2-methyl-4-pyridin-2-ylpiperazin-1-yl)methyl]-1H-benzimidazole;

2-{[(2S)-2-methyl-4-pyridin-2-ylpiperazin-1-yl]methyl}-1H-benzimidazole;

2-{[(2R)-2-methyl-4-pyridin-2-ylpiperazin-1-yl]methyl}-1H-benzimidazole;

N-{2-[4-(1H-benzimidazol-2-ylmethyl)piperazin-1-yl]pyridin-3-yl}methanesulfonamide;

2-{[4-(3-fluoropyridin-2-yl)piperazin-1-yl]methyl}-1H-benzimidazole; or a pharmaceutically acceptable salt, ester, amide, or prodrug thereof.

In another embodiment, the present invention relates to a method of treating female anorgasmia, clitoral erectile insufficiency, vaginal engorgement, dyspareunia, or vaginismus in a female human comprising administering to said female human in need of such treatment a therapeutically effective amount of 2-[(4-pyridin-2-ylpiperazin-1-yl)methyl]-1H-benzimidazole or a pharmaceutically acceptable salt, ester, amide, or prodrug thereof.

In another embodiment, the present invention relates to a method of treating female anorgasmia, clitoral erectile insufficiency, vaginal engorgement, dyspareunia, or vaginismus in a female human comprising administering to said female human in need of such treatment a therapeutically effective amount of 2-[(4-pyridin-2-ylpiperazin-1-yl)methyl]-1H-benzimidazole bis((L)tartrate).

In another embodiment, the present invention relates to a method of treating female anorgasmia, clitoral erectile insufficiency, vaginal engorgement, dyspareunia, or vaginismus in a female human comprising administering to said female human in need of such treatment a therapeutically effective amount of 2-[(4-pyrimidin-2-ylpiperazin-1-yl)methyl]-1H-benzimidazole or a pharmaceutically acceptable salt, ester, amide, or prodrug thereof.

In another embodiment, the present invention relates to a method of treating female anorgasmia, clitoral erectile insufficiency, vaginal engorgement, dyspareunia, or vaginismus in a female human comprising administering to said female human in need of such treatment a therapeutically effective amount of a compound of 6-[4-(1H-benzimidazol-2-ylmethyl)piperazin-1-yl]pyridin-3-ol or a pharmaceutically acceptable salt, ester, amide, or prodrug thereof.

In another embodiment, the present invention relates to a method of treating a disorder selected from cardiovascular disorders, infammatory disorders, attention deficit hyperactivity disorder, Alzheimer's disease, drug abuse, Parkinson's disease, anxiety, mood disorders and depression in a human comprising administering to said human in need of such treatment a therapeutically effective amount of a compound of formula (I) or a pharmaceutically acceptable salt, ester, amide, or prodrug thereof.

In another embodiment, the present invention relates to a method of treating a disorder selected from cardiovascular disorders, infammatory disorders, attention deficit hyperactivity disorder, Alzheimer's disease, drug abuse, Parkinson's disease, anxiety, mood disorders and depression in a human comprising administering to said human in need of such treatment a therapeutically effective amount of a compound of formula (I) wherein said compound of formula (I) is selected from 2-{[4-(3-methylpyridin-2-yl)piperazin-1-yl]methyl}-1H-benzimidazole;
2-[4-(1H-benzimidazol-2-ylmethyl)piperazin-1-yl]nicotinonitrile;
5,7-dibromo-2-[(4-pyridin-2-ylpiperazin-1-yl)methyl]-1H-benzimidazole;
5-fluoro-2-[(4-pyridin-2-ylpiperazin-1-yl)methyl]-1H-benzimidazole;
2-{[4-(1,3-thiazol-2-yl)piperazin-1-yl]methyl}-1H-benzimidazole;
isobutyl 2-[(4-pyridin-2-ylpiperazin-1-yl)methyl]-1H-benzimidazole-1-carboxylate;
2-[(4-pyridin-2-ylpiperazin-1-yl)methyl]-1-(pyrrolidin-1-ylcarbonyl)-1H-benzimidazole;
N,N-dimethyl-2-[(4-pyridin-2-ylpiperazin-1-yl)methyl]-1H-benzimidazole-1-carboxamide;
2-[(4-phenylpiperazin-1-yl)methyl]-1H-benzimidazole;
2-[4-(1H-benzimidazol-2-ylmethyl)piperazin-1-yl]benzonitrile;
2-{[4-(2-chlorophenyl)piperazin-1-yl]methyl}-1H-benzimidazole;
2-{[4-(2-fluorophenyl)piperazin-1-yl]methyl}-1H-benzimidazole;
2-{[4-(2-nitrophenyl)piperazin-1-yl]methyl}-1H-benzimidazole;
2-{[4-(2-methoxyphenyl)piperazin-1-yl]methyl}-1H-benzimidazole;
4-[4-(1H-benzimidazol-2-ylmethyl)piperazin-1-yl]phenol;
2-({4-[2-(methylthio)phenyl]piperazin-1-yl}methyl)-1H-benzimidazole;
2-{[4-(2-ethoxyphenyl)piperazin-1-yl]methyl}-1H-benzimidazole;
2-[4-(1H-benzimidazol-2-ylmethyl)piperazin-1-yl]phenol;
2-{[4-(2-methoxyphenyl)piperidin-1-yl]methyl}-1H-benzimidazole;
2-[(4-pyridin-2-ylpiperidin-1-yl)methyl]-1H-benzimidazole;
2-[(4-phenyl-3,6-dihydropyridin-1(2H)-yl)methyl]-1H-benzimidazole;
2-{[4-(6-methylpyridin-2-yl)piperazin-1-yl]methyl}-1H-benzimidazole;
2-[(2-methyl-4-pyridin-2-ylpiperazin-1-yl)methyl]-1H-benzimidazole;
2-{[(2S)-2-methyl-4-pyridin-2-ylpiperazin-1-yl]methyl}-1H-benzimidazole;
2-{[(2R)-2-methyl-4-pyridin-2-ylpiperazin-1-yl]methyl}-1H-benzimidazole;
N-(2-[4-(1H-benzimidazol-2-ylmethyl)piperazin-1-yl]pyridin-3-yl}methanesulfonamide;
2-{[4-(3-fluoropyridin-2-yl)piperazin-1-yl]methyl}-1H-benzimidazole; or a pharmaceutically acceptable salt, ester, amide, or prodrug thereof.

In another embodiment, the present invention relates to a method of treating a disorder selected from cardiovascular disorders, infammatory disorders, attention deficit hyperactivity disorder, Alzheimer's disease, drug abuse, Parkinson's disease, anxiety, mood disorders and depression in a human comprising administering to said human in need of such treatment a therapeutically effective amount of 2-[(4-pyridin-2-ylpiperazin-1-yl)methyl]-1H-benzimidazole or a pharmaceutically acceptable salt, ester, amide, or prodrug thereof.

In another embodiment, the present invention relates to a method of treating a disorder selected from cardiovascular disorders, infammatory disorders, attention deficit hyperactivity disorder, Alzheimer's disease, drug abuse, Parkinson's disease, anxiety, mood disorders and depression in a human comprising administering to said human in need of such treatment a therapeutically effective amount of 2-[(4-pyridin-2-ylpiperazin-1-yl)methyl]-1H-benzimidazole bis((L) tartrate).

In another embodiment, the present invention relates to a method of treating a disorder selected from cardiovascular disorders, infammatory disorders, attention deficit hyperactivity disorder, Alzheimer's disease, drug abuse, Parkinson's disease, anxiety, mood disorders and depression in a human comprising administering to said human in need of such treatment a therapeutically effective amount of 2-[(4-pyrimidin-2-ylpiperazin-1-yl)methyl]-1H-benzimidazole or a pharmaceutically acceptable salt, ester, amide, or prodrug thereof.

In another embodiment, the present invention relates to a method of treating a disorder selected from cardiovascular disorders, infammatory disorders, attention deficit hyperactivity disorder, Alzheimer's disease, drug abuse, Parkinson's disease, anxiety, mood disorders and depression in a human comprising administering to said human in need of such treatment a therapeutically effective amount of 6-[4-(1H-benzimidazol-2-ylmethyl)piperazin-1-yl]pyridin-3-ol or a pharmaceutically acceptable salt, ester, amide, or prodrug thereof.

In another embodiment, the present invention relates to compounds of formula (II)

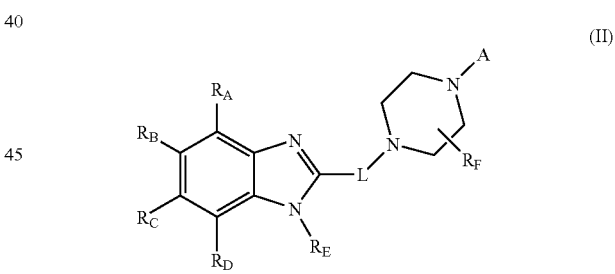

or a pharmaceutically acceptable salt, ester, amide, or prodrug thereof, wherein A is a selected from

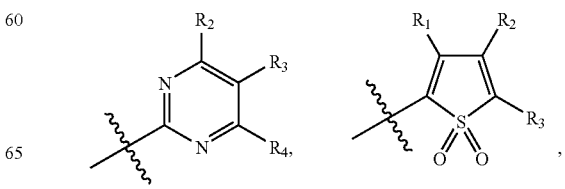

-continued

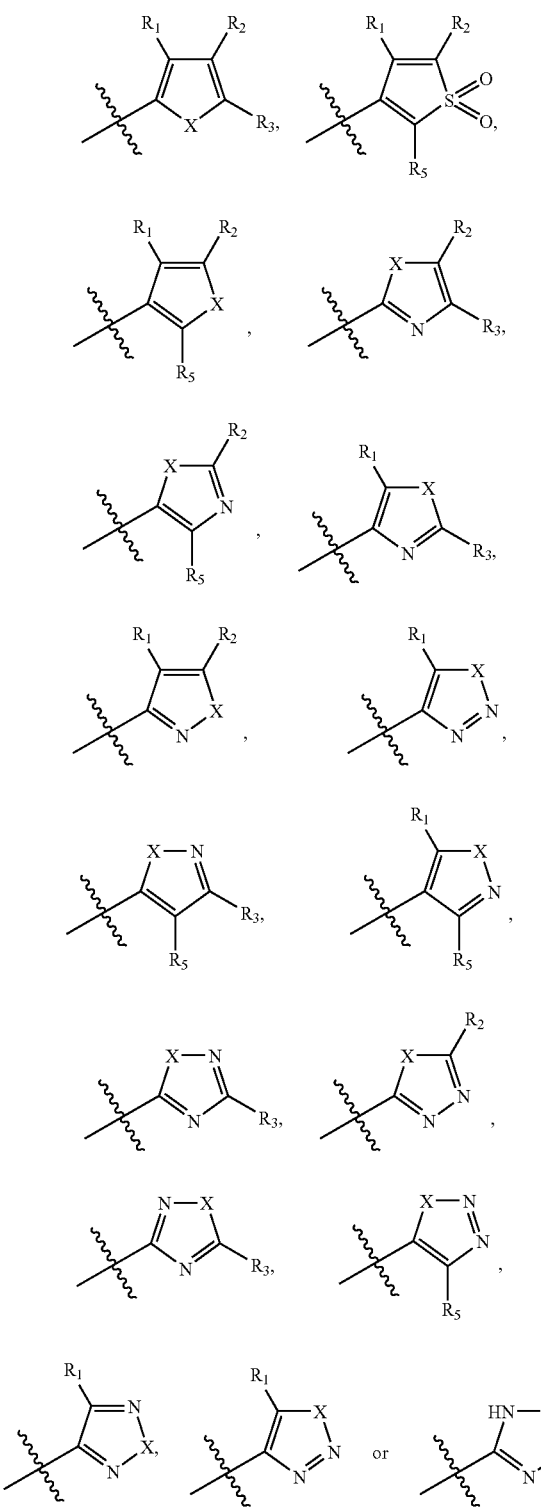

X is selected from NH, O or S;
L is selected from CH₂, CH₂CH₂, CH₂CH₂CH₂ or CH₂CH₂CH₂CH₂;
$R_1$, $R_2$, $R_3$, $R_4$ and $R_5$ are each independently selected from hydrogen, alkoxy, alkenyl, alkyl, alkylsulfinyl, alkylsulfonyl, alkylthio, alkynyl, alkoxycarbonyl, alkylcarbonyl, alkylcarbonyloxy, carboxy, cyano, formyl, halogen, haloalkoxy, haloalkyl, hydroxy, hydroxyalkyl, mercapto, nitro, —NZ₁Z₂ or (NZ₁Z₂)carbonyl wherein Z, and Z₂ are each independently selected from the group consisting of hydrogen, alkyl, alkylcarbonyl, alkylsulfonyl or formyl;

$R_A$, $R_B$, $R_C$ and $R_D$ are each independently selected from hydrogen, alkoxy, alkenyl, alkyl, alkylsulfinyl, alkylsulfonyl, alkylthio, alkynyl, alkoxycarbonyl, alkylcarbonyl, alkylcarbonyloxy, carboxy, cyano, formyl, halogen, haloalkoxy, haloalkyl, hydroxy, hydroxyalkyl, mercapto, nitro, —NZ₁Z₂ or (NZ₁Z₂)carbonyl;

$R_E$ is selected from hydrogen, alkoxycarbonyl, alkyl, alkylcarbonyl, arylcarbonyl, cycloalkylcarbonyl, heterocyclecarbonyl or (NZ₁Z₂)carbonyl; and $R_F$ Is selected from the group consisting of hydrogen or alkyl;

provided that when A is

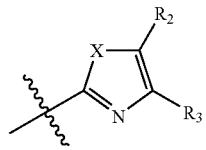

and X is S, then $R_2$ or $R_3$ is other than hydrogen.

In another embodiment, the present invention relates to compounds of formula (II) wherein $R_A$, $R_B$, $R_C$ and $R_D$ are each independently selected from hydrogen or halogen; $R_E$ is hydrogen; A is

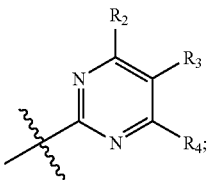

and L, $R_2$, $R_3$ and $R_4$ are as defined in formula (II).

In another embodiment, the present invention relates to compounds of formula (II) wherein $R_A$, $R_B$, $R_C$ and $R_D$ are each independently selected from hydrogen or halogen; $R_E$ and $R_F$ are each hydrogen; L is CH₂; A is

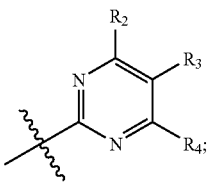

and $R_2$, $R_3$ and $R_4$ are each hydrogen.

In another embodiment, the present invention relates to compounds of formula (III)

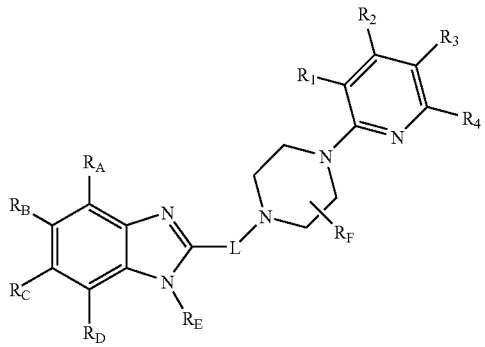

(III)

or a pharmaceutically acceptable salt, ester, amide or prodrug thereof, wherein $R_1$, $R_2$, $R_3$ and $R_4$ are each independently selected from hydrogen, alkylsulfinyl, alkylsulfonyl, alkylsulfonylamino, alkylthio or hydroxy;

L is selected from $CH_2$, $CH_2CH_2$, $CH_2CH_2CH_2$ or $CH_2CH_2CH_2CH_2$;

$R_A$, $R_B$, $R_C$ and $R_D$ are each independently selected from hydrogen, alkoxy, alkenyl, alkyl, alkylsulfinyl, alkylsulfonyl, alkylthio, alkynyl, alkoxycarbonyl, alkylcarbonyl, alkylcarbonyloxy, carboxy, cyano, formyl, halogen, haloalkoxy, haloalkyl, hydroxy, hydroxyalkyl, mercapto, nitro, —$NZ_1Z_2$ or ($NZ_1Z_2$)carbonyl wherein $Z_1$ and $Z_2$ are each independently selected from the group consisting of hydrogen, alkyl, alkylcarbonyl, alkylsulfonyl or formyl;

$R_E$ is selected from hydrogen, alkoxycarbonyl, alkyl, alkylcarbonyl, arylcarbonyl, cycloalkylcarbonyl, heterocyclecarbonyl or ($NZ_1Z_2$)carbonyl; and $R_F$ is selected from the group consisting of hydrogen or alkyl;

provided that when $R_F$ is hydrogen, at least one of $R_1$, $R_2$, $R_3$ or $R_4$ is other than hydrogen.

In another embodiment, the present invention relates to compounds of formula (III) wherein $R_1$, $R_2$, $R_3$ and $R_4$ are each independently selected from hydrogen or hydroxy provided that at least one of $R_1$, $R_2$, $R_3$ or $R_4$ is hydroxy; $R_A$, $R_B$, $R_C$ and $R_D$ are each independently selected from hydrogen or halogen; $R_E$ is hydrogen; and L is as defined in formula (I).

In another embodiment, the present invention relates to compounds of formula (III) wherein $R_1$, $R_2$ and $R_4$ are each hydrogen; $R_3$ is hydroxy; L is $CH_2$; $R_A$, $R_B$, $R_C$ and $R_D$ are each independently selected from hydrogen or halogen; and $R_E$ and $R_F$ are each hydrogen.

In another embodiment, the present invention relates to compounds of formula (III) wherein $R_1$, $R_2$, $R_3$ and $R_4$ are each hydrogen; L is $CH_2$; $R_A$, $R_B$, $R_C$ and $R_D$ are each independently selected from hydrogen or halogen; $R_E$ is hydrogen; and $R_F$ is alkyl.

In another embodiment, the present invention relates to compounds of formula (III) wherein $R_1$, $R_2$, $R_3$ and $R_4$ are each independently selected from hydrogen or alkylsulfonylamino provided that at least one of $R_1$, $R_2$, $R_3$ or $R_4$ is alkylsulfonylamino; $R_A$, $R_B$, $R_C$ and $R_D$ are each independently selected from hydrogen or halogen; $R_E$ is hydrogen; and $R_F$ is as defined in formula (III).

In another embodiment, the present invention relates to compounds of formula (III) wherein $R_1$, $R_3$ and $R_4$ are each hydrogen; $R_1$ is alkylsulfonylamino; L is $CH_2$; $R_A$, $R_B$, $R_C$ and $R_D$ are each independently selected from hydrogen or halogen; and $R_E$ and $R_F$ are each hydrogen.

In another embodiment, the present invention relates to compounds of formula (IV)

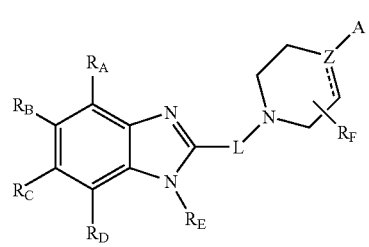

(IV)

or a pharmaceutically acceptable salt, ester, amide, or prodrug thereof, wherein A is a selected from

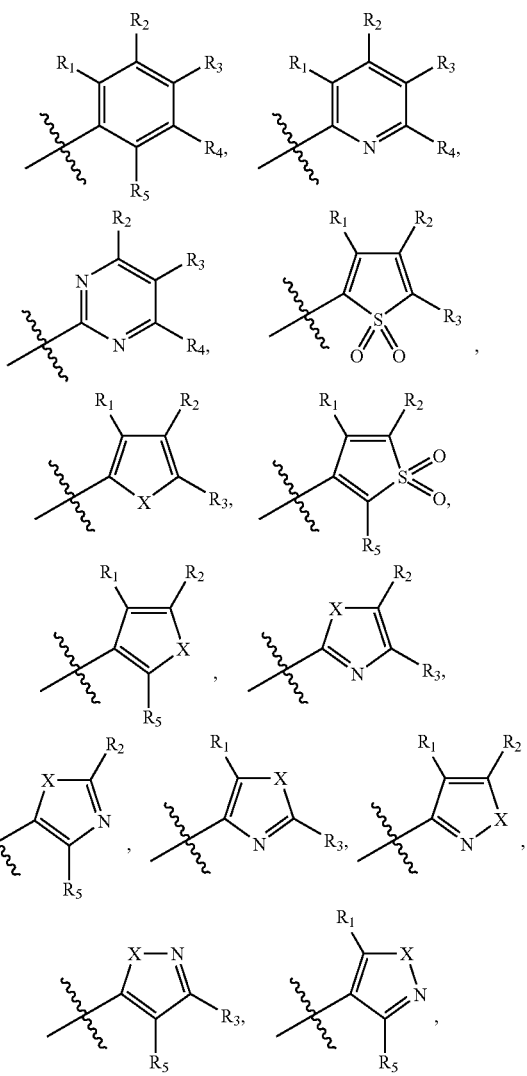

-continued

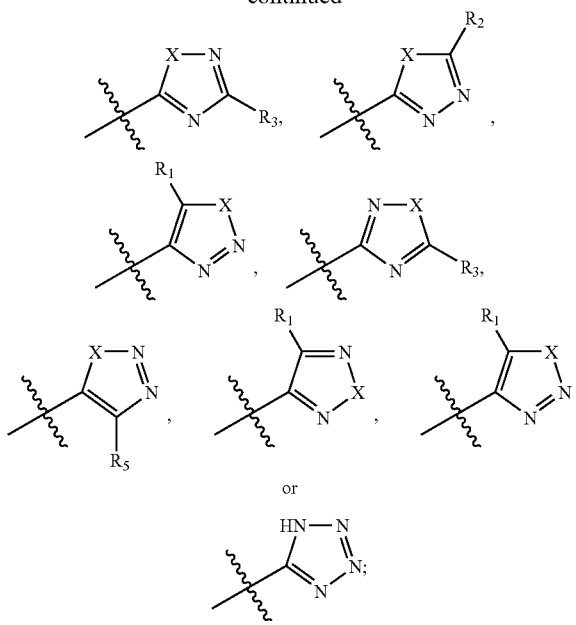

X is selected from NH, O or S;

L is selected from $CH_2$, $CH_2CH_2$, $CH_2CH_2CH_2$ or $CH_2CH_2CH_2CH_2$;

$R_1$, $R_2$, $R_3$, $R_4$ and $R_5$ are each independently selected from hydrogen, alkoxy, alkenyl, alkyl, alkylsulfinyl, alkylsulfonyl, alkylthio, alkynyl, alkoxycarbonyl, alkylcarbonyl, alkylcarbonyloxy, carboxy, cyano, formyl, halogen, haloalkoxy, haloalkyl, hydroxy, hydroxyalkyl, mercapto, nitro, $-NZ_1Z_2$ or $(NZ_1Z_2)$carbonyl wherein $Z_1$ and $Z_2$ are each independently selected from the group consisting of hydrogen, alkyl, alkylcarbonyl, alkylsulfonyl or formyl;

$R_A$, $R_B$, $R_C$ and $R_D$ are each independently selected from hydrogen, alkoxy, alkenyl, alkyl, alkylsulfinyl, alkylsulfonyl, alkylthio, alkynyl, alkoxycarbonyl, alkylcarbonyl, alkylcarbonyloxy, carboxy, cyano, formyl, halogen, haloalkoxy, haloalkyl, hydroxy, hydroxyalkyl, mercapto, nitro, $-NZ_1Z_2$ or $(NZ_1Z_2)$carbonyl;

$R_E$ is selected from hydrogen, alkoxycarbonyl, alkyl, alkylcarbonyl, arylcarbonyl, cycloalkylcarbonyl, heterocyclecarbonyl or $(NZ_1Z_2)$carbonyl;

$R_F$ is selected from hydrogen or alkyl;

Z is selected from C or CH; and

— is a bond when Z is C and — is absent when Z is CH.

In another embodiment, the present invention relates to compounds of formula (IV) wherein $R_A$, $R_B$, $R_C$ and $R_D$ are each independently selected from hydrogen or halogen; $R_E$ is hydrogen; Z is CH; — is absent; A is

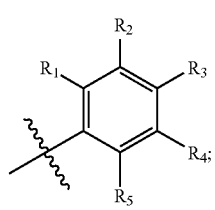

and L, $R_1$, $R_2$, $R_3$, $R_4$ and $R_5$ are as defined in formula (IV).

In another embodiment, the present invention relates to compounds of formula (IV) wherein $R_A$, $R_B$, $R_C$ and $R_D$ are each independently selected from hydrogen or halogen; $R_E$ and $R_F$ are each hydrogen; L is $CH_2$; Z is CH; — is absent; A is

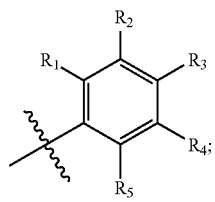

$R_2$, $R_3$ and $R_4$ are each hydrogen; and $R_1$ and $R_5$ are as defined in formula (IV).

In another embodiment, the present invention relates to compounds of formula (IV) wherein $R_A$, $R_B$, $R_C$ and $R_D$ are each independently selected from hydrogen or halogen; $R_E$ is hydrogen; Z is CH; — is absent; A is

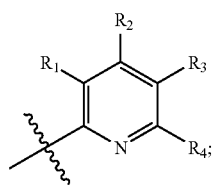

and L, $R_1$, $R_2$, $R_3$ and $R_4$ are as defined in formula (IV).

In another embodiment, the present invention relates to compounds of formula (IV) wherein $R_A$, $R_B$, $R_C$ and $R_D$ are each independently selected from hydrogen or halogen; $R_E$ and $R_F$ are each hydrogen; L is $CH_2$; Z is CH; — is absent; A is

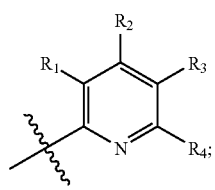

$R_2$, $R_3$ and $R_4$ are each hydrogen; and $R_1$ is as defined in formula (IV).

In another embodiment, the present invention relates to compounds of formula (IV) wherein $R_A$, $R_B$, $R_C$ and $R_D$ are each independently selected from hydrogen or halogen; $R_E$ is hydrogen; Z is C; — is a bond; and A is

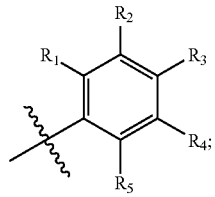

and L, $R_1$, $R_2$, $R_3$, $R_4$ and $R_5$ are as defined in formula (IV).

In another embodiment, the present invention relates to compounds of formula (IV) wherein $R_A$, $R_B$, $R_C$ and $R_D$ are each independently selected from hydrogen or halogen; $R_E$ and $R_F$ are each hydrogen; L is $CH_2$; Z is C; — is a bond; A is

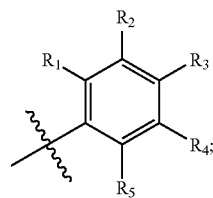

$R_2$, $R_3$ and $R_4$ are each hydrogen; and $R_1$ and $R_5$ are as defined in formula (IV).

Definitions of the Present Invention

As used throughout this specification and the appended claims, the following terms have the following meanings:

The term "alkenyl," as used herein, refers to a straight or branched chain hydrocarbon containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4pentenyl, 5-hexenyl, 2-heptenyl, 2-methyl-1-heptenyl, and 3-decenyl.

The term "alkoxy," as used herein, refers to an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxyalkoxy," as used herein, refers to an alkoxy group, as defined herein, appended to the parent molecular moiety through another alkoxy group, as defined herein. Representative examples of alkoxyalkoxy include, but are not limited to, tert-butoxymethoxy, 2-ethoxyethoxy, 2-methoxyethoxy, and methoxymethoxy.

The term "alkoxyalkyl," as used herein, refers to an alkoxy group, as defined herein, appended to the parent molecular moiety through an alkyl group, as defined herein. Representative examples of alkoxyalkyl include, but are not limited to, tert-butoxymethyl, 2-ethoxyethyl, 2-methoxyethyl, and methoxymethyl.

The term "alkoxycarbonyl," as used herein, refers to an alkoxy group, as defined herein, appended to the parent molecular moiety through a carbonyl group, as defined herein. Representative examples of alkoxycarbonyl include, but are not limited to, methoxycarbonyl, ethoxycarbonyl, and tert-butoxycarbonyl.

The term "alkoxycarbonylalkyl," as used herein, refers to an alkoxycarbonyl group, as defined herein, appended to the parent molecular moiety through an alkyl group, as defined herein. Representative examples of alkoxycarbonylalkyl include, but are not limited to, 3-methoxycarbonylpropyl, 4-ethoxycarbonylbutyl, and 2-tert-butoxycarbonylethyl.

The term "alkoxysulfonyl," as used herein, refers to an alkoxy group, as defined herein, appended appended to the parent molecular moiety through a sulfonyl group, as defined herein. Representative examples of alkoxysulfonyl include, but are not limited to, methoxysulfonyl, ethoxysulfonyl and propoxysulfonyl.

The term "alkyl," as used herein, refers to a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylcarbonyl," as used herein, refers to an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl.

The term "alkylcarbonylalkyl," as used herein, refers to an alkylcarbonyl group, as defined herein, appended to the parent molecular moiety through an alkyl group, as defined herein. Representative examples of alkylcarbonylalkyl include, but are not limited to, 2-oxopropyl, 3,3-dimethyl-2-oxopropyl, 3-oxobutyl, and 3-oxopentyl.

The term "alkylcarbonyloxy," as used herein, refers to an alkylcarbonyl group, as defined herein, appended to the parent molecular moiety through an oxygen atom. Representative examples of alkylcarbonyloxy include, but are not limited to, acetyloxy, ethylcarbonyloxy, and tert-butylcarbonyloxy.

The term "alkylsulfinyl," as used herein, refers to an alkyl group, as defined herein, appended to the parent molecular moiety through a sulfinyl group, as defined herein. Representative examples of alkylsulfinyl include, but are not limited to, methylsulfinyl and ethylsulfinyl.

The term "alkylsulfonyl," as used herein, refers to an alkyl group, as defined herein, appended to the parent molecular moiety through a sulfonyl group, as defined herein. Representative examples of alkylsulfonyl include, but are not limited to, methylsulfonyl and ethylsulfonyl.

The term "alkylsulfonylamino," as used herein, refers to an alkylsulfonyl group, as defined herein, appended to the parent molecular moiety through an NH group. Representative examples of alkylsulfonylamino include, but are not limited to, methylsulfonylamino and ethylsulfonylamino.

The term "alkylthio," as used herein, refers to an alkyl group, as defined herein, appended to the parent molecular moiety through a sulfur atom. Representative examples of alkylthio include, but are not limited to, methylsulfanyl, ethylsulfanyl, tert-butylsulfanyl, and hexylsulfanyl.

The term "alkylthioalkyl," as used herein, refers to an alkylthio group, as defined herein, appended to the parent molecular moiety through an alkyl-group, as defined herein. Representative examples of alkylthioalkyl include, but are not limited, methylsulfanylmethyl and 2-(ethylsulfanyl) ethyl.

The term "alkynyl," as used herein, refers to a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "aryl," as used herein, refers to a monocyclio-ring system, or a bicyclic- or a tricyclic-fused ring system wherein one or more of the fused rings are aromatic. Representative examples of aryl include, but are not limited to, anthracenyl, azulenyl, fluorenyl, indanyl, indenyl, naphthyl, phenyl, and tetrahydronaphthyl.

The aryl groups of this invention can be substituted with 1, 2, 3, 4 or 5 substituents independently selected from alkenyl, alkoxy, alkoxyalkoxy, alkoxyalkyl, alkoxycarbonyl, alkoxycarbonylalkyl, alkoxysulfonyl, alkyl, alkylcarbonyl, alkylcarbonylalkyl, alkylcarbonyloxy, alkylthio, alkylthioalkyl, alkynyl, carboxy, carboxyalkyl, cyano, cyanoalkyl, ethylenedioxy, formyl, haloalkoxy, haloalkyl, halogen, hydroxy, hydroxyalkyl, mercapto, methylenedioxy, nitro, —$NZ_1Z_2$ and ($NZ_1Z_2$)carbonyl.

The term "arylcarbonyl," as used herein, refers to an aryl group, as defined herein, appended to the parent molecular moiety through a carbonyl group, as defined herein. Representative examples of arylcarbonyl include, but are not limited to, benzoyl and naphthoyl.

The term "carbonyl," as used herein, refers to a —C(O)— group.

The term "carboxy," as used herein, refers to a —$CO_2H$ group.

The term "carboxyalkyl," as used herein, refers to a carboxy group, as defined herein, appended to the parent molecular moiety through an alkyl group, as defined herein. Representative examples of carboxyalkyl include, but are not limited to, carboxymethyl, 2-carboxyethyl, and 3-carboxypropyl.

The term "cyano," as used herein, refers to a —CN group.

The term "cyanoalkyl," as used herein, refers to a cyano group, as defined herein, appended to the parent molecular moiety through an alkyl group, as defined herein. Representative examples of cyanoalkyl include, but are not limited to, cyanomethyl, 2-cyanoethyl, and 3-cyanopropyl.

The term "cycloalkyl," as used herein, refers to a saturated cyclic hydrocarbon group containing from 3 to 8 carbons. Examples of cycloalkyl include cyclopropyl, cyclobutyl, cyclopentyl, cyclohexyl, cycloheptyl, and cyclooctyl.

The term "cycloalkylcarbonyl," as used herein, refers to cycloalkyl group, as defined herein, appended to the parent molecular moiety through a carbonyl group, as defined herein. Representative examples of cycloalkylcarbonyl include, but are not limited to, cyclopropylcarbonyl, cyclobutylcarbonyl, and cyclohexylcarbonyl.

The term "ethylenedioxy," as used herein, refers to a —O($CHR_2$)$_2$O— group wherein the oxygen atoms of the ethylenedioxy group are attached to the parent molecular moiety through one carbon atom forming a 5 membered ring or the oxygen atoms of the ethylenedioxy group are attached to the parent molecular moiety through two adjacent carbon atoms forming a six membered ring.

The term "formyl," as used herein, refers to a —C(O)H group.

The term "halo" or "halogen," as used herein, refers to —Cl, —Br, —I or —F.

The term "haloalkoxy," as used herein, refers to at least one halogen, as defined herein, appended to the parent molecular moiety through an alkoxy group, as defined herein. Representative examples of haloalkoxy include, but are not limited to, 2-fluoro-1-chloroethoxy, chloromethoxy, 2-fluoroethoxy, trifluoromethoxy, and pentafluoroethoxy.

The term "haloalkyl," as used herein, refers to at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "heterocycle" or "heterocyclic," as used herein, refers to a monocyclic, bicyclic, or tricyclic ring system. Monocyclic ring systems are exemplified by any 3- or 4-membered ring containing a heteroatom independently selected from oxygen, nitrogen and sulfur; or a 5-, 6- or 7-membered ring containing one, two or three heteroatoms wherein the heteroatoms are independently selected from nitrogen, oxygen and sulfur. The 5-membered ring has from 0-2 double bonds and the 6- and 7-membered ring have from 0-3 double bonds. Representative examples of monocyclic ring systems include, but are not limited to, azetidinyl, azepanyl, aziridinyl, diazepinyl, 1,3-dioxolanyl, dioxanyl, dithianyl, furyl, imidazolyl, imidazolinyl, imidazolidinyl, isothiazolyl, isothiazolinyl, isothiazolidinyl, isoxazolyl, isoxazolinyl, isoxazolidinyl, morpholinyl, oxadiazolyl, oxadiazolinyl, oxadiazolidinyl, oxazolyl, oxazolinyl, oxazolidinyl, piperazinyl, piperidinyl, pyranyl, pyrazinyl, pyrazolyl, pyrazolinyl, pyrazolidinyl, pyridinyl, pyrimidinyl, pyridazinyl, pyrrolyl, pyrrolinyl, pyrrolidinyl, tetrahydrofuranyl, tetrahydrothienyl, tetrazinyl, tetrazolyl, thiadiazolyl, thiadiazolinyl, thiadiazolidinyl, thiazolyl, thiazolinyl, thiazolidinyl, thienyl, thiomorpholinyl, 1,1-dioxidothiomorpholinyl (thiomorpholine sulfone), thiopyranyl, triazinyl, triazolyl, and trithianyl. Bicyclic ring systems are exemplified by any of the above monocyclic ring systems fused to an aryl group as defined herein, a cycloalkyl group as defined herein, or another monocyclic ring system. Representative examples of bicyclic ring systems include but are not limited to, for example, benzimidazolyl, benzodioxinyl, benzothiazolyl, benzothienyl, benzotriazolyl, benzoxazolyl, benzofuranyl, benzopyranyl, benzothiopyranyl, cinnolinyl, indazolyl, indolyl, 2,3-dihydroindolyl, indolizinyl, naphthyridinyl, isobenzofuranyl, isobenzothienyl, isoindolyl, isoquinolinyl, phthalazinyl, pyranopyridinyl, quinolinyl, quinolizinyl, quinoxalinyl, quinazolinyl, tetrahydroisoquinolinyl, tetrahydroquinolinyl, and thiopyranopyridinyl. Tricyclic rings systems are exemplified by any of the above bicyclic ring systems fused to an aryl group as defined herein, a cycloalkyl group as defined herein, or a monocyclic ring system. Representative examples of tricyclic ring systems include, but are not limited to, acridinyl, carbazolyl, carbolinyl, dibenzo[b,d]furanyl, dibenzo[b,d]thienyl, naphtho[2,3-b]furan, naphtho[2,3-b]thienyl, phenazinyl, phenothiazinyl, phenoxazinyl, thianthrenyl, thioxanthenyl and xanthenyl.

The heterocycles of this invention can be substituted with 1, 2, or 3 substituents independently selected from alkenyl, alkoxy, alkoxyalkoxy, alkoxyalkyl, alkoxycarbonyl, alkoxycarbonylalkyl, alkoxysulfonyl, alkyl, alkylcarbonyl, alkylcarbonylalkyl, alkylcarbonyloxy, alkylthio, alkylthioalkyl, alkynyl, carboxy, carboxyalkyl, cyano, cyanoalkyl, ethylenedioxy, formyl, haloalkoxy, haloalkyl, halogen, hydroxy, hydroxyalkyl, mercapto, methylenedioxy, nitro, oxo, —$NZ_1Z_2$ and ($NZ_1Z_2$)carbonyl.

The term "heterocyclecarbonyl," as used herein, refers to a heterocycle, as defined herein, appended to the parent molecular moiety through a carbonyl group, as defined herein. Representative examples of heterocyclecarbonyl include, but are not limited to, pyridin-3-ylcarbonyl and quinolin-3-ylcarbonyl.

The term "hydroxy," as used herein, refers to an —OH group.

The term "hydroxyalkyl," as used herein, refers to at least one hydroxy group, as defined herein, appended to the parent molecular moiety through an alkyl group, as defined herein. Representative examples of hydroxyalkyl include, but are not limited to, hydroxymethyl, 2-hydroxyethyl, 3-hydroxypropyl 2-ethyl-4-hydroxyheptyl and 2,4-dihydroxybutyl.

The term "hydroxy-protecting group" or "O-protecting group," refers to a substituent which protects hydroxyl groups against undesirable reactions during synthetic procedures. Examples of hydroxy-protecting groups include, but are not limited to, substituted methyl ethers, for example, methoxymethyl, benzyloxymethyl, 2-methoxyethoxymethyl, 2-(trimethylsilyl)-ethoxymethyl, benzyl, and triphenylmethyl; tetrahydropyranyl ethers; substituted ethyl ethers, for example, 2,2,2-trichloroethyl and t-butyl; silyl ethers, for example, trimethylsilyl, t-butyldimethylsilyl and t-butyldiphenylsilyl; cyclic acetals and ketals, for example, methylene acetal, acetonide and benzylidene acetal; cyclic ortho esters, for example, methoxymethylene; cyclic carbonates; and cyclic boronates.

The term "mercapto," as used herein, refers to a —SH group.

The term "methylenedioxy," as used herein, refers to a —OCH$_2$O— group wherein the oxygen atoms of the methylenedioxy are attached to the parent molecular moiety through two adjacent carbon atoms.

The term "nitro," as used herein, refers to a —NO$_2$ group.

The term "nitrogen protecting group," as used herein, refers to those groups intended to protect an amino group against undesirable reactions during synthetic procedures. Nitrogen protecting groups comprise carbamates, amides, N-benzyl derivatives, and imine derivatives. Preferred nitrogen protecting groups are acetyl, benzoyl, benzyl, benzyloxycarbonyl (Cbz), formyl, phenylsulfonyl, pivaloyl, tert-butoxycarbonyl (Boc), tert-butylacetyl, trifluoroacetyl, and triphenylmethyl (trityl).

The term "—NZ$_1$Z$_2$," as used herein, refers to two groups, Z$_1$ and Z$_2$, which are appended to the parent molecular moiety through a nitrogen atom. Z$_1$ and Z$_2$ are each independently selected from hydrogen, alkyl, alkylcarbonyl, alkylsulfonyl and formyl. Representative examples of —NZ$_1$Z$_2$ include, but are not limited to, amino, methylamino, dimethylamino, acetylamino, (acetyl)(methyl)amino, and (methylsulfonyl)amino.

The term "(NZ$_1$Z$_2$)carbonyl," as used herein, refers to a —NZ$_1$Z$_2$ group, as defined herein, appended to the parent molecular moiety through a carbonyl group, as defined herein.

Representative examples of (NZ$_1$Z$_2$)carbonyl include, but are not limited to, aminocarbonyl, (methylamino)carbonyl, (dimethylamino)carbonyl, ((acetyl)(methyl)amino)carbonyl and (ethylmethylamino)carbonyl.

The term "(NZ$_1$Z$_2$)sulfonyl," as used herein, refers to a NZ$_1$Z$_2$ group, as defined herein, appended to the parent molecular moiety through a sulfonyl group, as defined herein. Representative examples of (NZ$_1$Z$_2$)sulfonyl include, but are not limited to, aminosulfonyl, (methylamino)sulfonyl, (dimethylamino)sulfonyl, ((acetyl)(methyl)amino)sulfonyl and (ethylmethylamino)sulfonyl.

The term "oxo," as used herein, refers to a =O moiety.

The term "sulfinyl," as used herein, refers to a —S(O)— group.

The term "sulfonyl," as used herein, refers to a —S(O)$_2$— group.

The term "sexual dysfunction," as used herein refers to sexual dysfunction in mammals including human male and human female sexual dysfunction.

The term "male sexual dysfunction," as used herein includes, but is not limited to, male erectile dysfunction and premature ejacualtion.

The term "female sexual dysfunction," as used herein includes, but is not limited to, female anorgasmia, clitoral erectile insufficiency, vaginal engorgement, dyspareunia, and vaginismus.

Compounds of the present invention may exist as stereoisomers wherein, asymmetric or chiral centers are present. These stereoisomers are "R" or "S" depending on the configuration of substituents around the chiral carbon atom. The terms "R" and "S" used herein are configurations as defined in IUPAC 1974 Recommendations for Section E, Fundamental Stereochemistry, Pure Appl. Chem., 1976, 45: 13-30. The present invention contemplates various stereoisomers and mixtures thereof and are specifically included within the scope of this invention. Stereoisomers include enantiomers and diastereomers, and mixtures of enantiomers or diastereomers. Individual stereoisomers of compounds of the present invention may be prepared synthetically from commercially available starting materials which contain asymmetric or chiral centers or by preparation of racemic mixtures followed by resolution well-known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary or (2) direct separation of the mixture of optical enantiomers on chiral chromatographic columns.

Preferred compounds of the present invention include:
2-{[4-(3-methylpyridin-2-yl)piperazin-1-yl]methyl}-1H-benzimidazole;
2-[4-(1H-benzimidazol-2-ylmethyl)piperazin-1-yl]nicotinonitrile;
5,7-dibromo-2-[(4-pyridin-2-ylpiperazin-1-yl)methyl]-1H-benzimidazole;
5-fluoro-2-[(4-pyridin-2-ylpiperazin-1-yl)methyl]-1H-benzimidazole;
2-{[4-(1,3-thiazol-2-yl)piperazin-1-yl]methyl}-1H-benzimidazole;
isobutyl 2-[(4-pyridin-2-ylpiperazin-1-yl)methyl]-1H-benzimidazole-1-carboxylate;
2-[(4-pyridin-2-ylpiperazin-1-yl)methyl]-1-(pyrrolidin-1-ylcarbonyl)-1H-benzimidazole;
N,N-dimethyl-2-[(4-pyridin-2-ylpiperazin-1-yl)methyl]-1H-benzimidazole-1-carboxamide;
2-[(4-phenylpiperazin-1-yl)methyl]-1H-benzimidazole;
2-[4-(1H-benzimidazol-2-ylmethyl)piperazin-1-yl]benzonitrile;
2-{[4-(2-chlorophenyl)piperazin-1-yl]methyl}-1H-benzimidazole;
2-{[4-(2-fluorophenyl)piperazin-1-yl]methyl}-1H-benzimidazole;
2-{[4-(2-nitrophenyl)piperazin-1-yl]methyl}-1H-benzimidazole;
2-{[4-(2-methoxyphenyl)piperazin-1-yl]methyl}-1H-benzimidazole;
4-[4-(1H-benzimidazol-2-ylmethyl)piperazin-1-yl]phenol;
2-({4-[2-(methylthio)phenyl]piperazin-1-yl}methyl)-1H-benzimidazole;
2-{[4-(2-ethoxyphenyl)piperazin-1-yl]methyl}-1H-benzimidazole;
2-[4-(1H-benzimidazol-2-ylmethyl)piperazin-1-yl]phenol;
2-{[4-(2-methoxyphenyl)piperidin-1-yl]methyl}-1H-benzimidazole;
2-[(4-pyridin-2-ylpiperidin-1-yl)methyl]-1H-benzimidazole; and
2-[(4-phenyl-3,6-dihydropyridin-1(2H)-yl)methyl]-1H-benzimidazole; or a pharmaceutically acceptable salt, ester, amide, or prodrug thereof.

More preferred compounds of the present invention are
6-[4-(1H-benzimidazol-2-ylmethyl)piperazin-1-yl]pyridin-3-ol and
2-[(4-pyrimidin-2-ylpiperazin-1-yl)methyl]-1H-benzimidazole.

The most preferred compound of the present invention is 2-[(4-pyridin-2-ylpiperazin-1-yl)methyl]-1H-benzimidazole.

Abbreviations

Abbreviations which have been used in the descriptions of the Schemes and the Examples that follow are: $BF_3OEt_2$ for boron trifluoride diethyl ether complex; BINAP for 2,2'-bis(diphenylphosphino)-1,1'-binaphthyl; Boc for tert-butoxycarbonyl; nBuLi for n-butyllithium; dba for dibenzylideneacetone; DME for dimethoxyethane; DMF for N,N-dimethylformamide; DMSO for dimethylsulfoxide; EtOH for ethanol; MeOH for methanol; TEA for triethylamine; TFA for trifluoroacetic acid; THF for tetrahydrofuran; THP for tetrahydropyran; TLC for thin layer chromatography.

Preparation of Compounds of the Present Invention

The compounds of this invention may be prepared by a variety of synthetic routes. Representative procedures are described in Schemes 1-5.

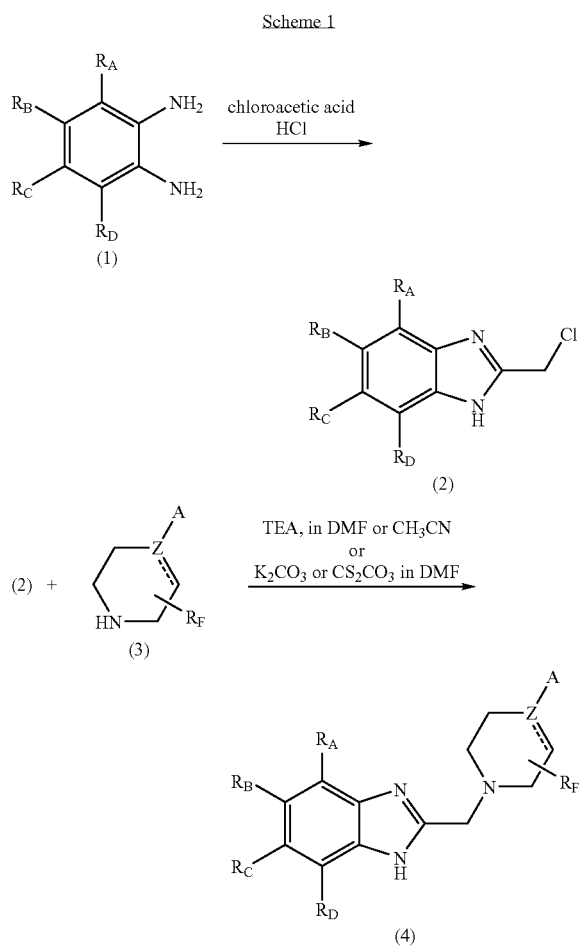

Benzimidazoles of general formula (4), wherein $R_A$, $R_B$, $R_C$, $R_D$, $R_F$, A, Z and — are as defined in formula (I), can be prepared as described in Scheme 1. Benzene-1,2-diamines of general formula (1) can be treated with chloroacetic acid and an acid such as 6N HCl to provide 2-chloromethylbenzimidazoles of general formula (2).

2-Chloromethylbenzimidazoles of general formula (2) can be treated with compounds of general formula (3) in the presence of a base such as triethylamine, potassium carbonate or cesium carbonate in a solvent such as acetonitrile or N,N-dimethylformamide to provide benzimidazoles of general formula (4).

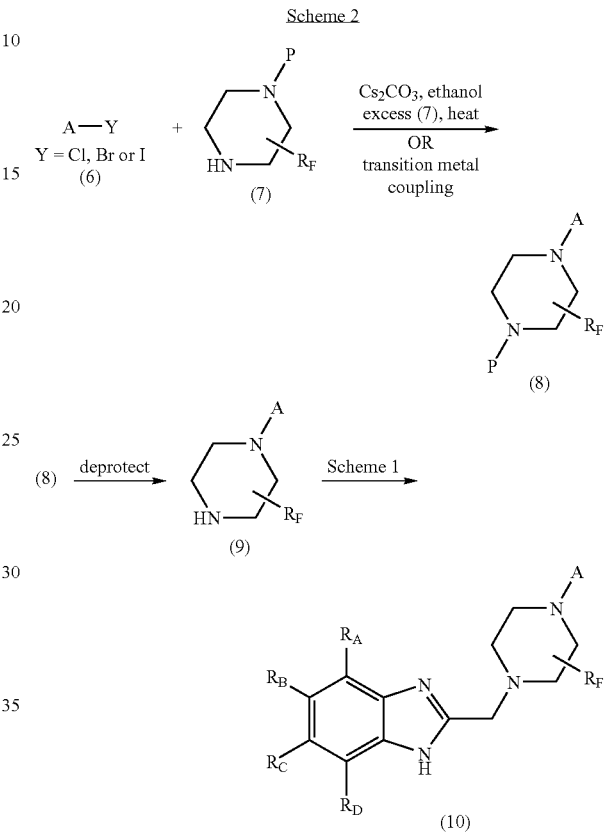

Benzimidazoles of general formula (10), wherein $R_A$, $R_B$, $R_C$, $R_D$, $R_F$ and A are as defined in formula (I), can be prepared as described in Scheme 2. Haloheterocycles of general formula (6), wherein Y is a halogen, can be treated with an excess of a N-protected piperazine of general formula (7), wherein P is a nitrogen protecting group such as —C(O)OC(CH$_3$)$_3$ or —C(O)OCH$_2$Ph, in a solvent such as ethanol or n-butanol with heat in the presence of a base such as cesium carbonate (or without base) to provide N-protected piperazines of general formula (8). Alternatively, haloheterocycles of general formula (6) and N-protected piperazines of general formula (7) can be treated with a transition metal catalyst as described in Wagaw and Buchwald, JOC 61 (1996) 7240-7241; Harris et al., JOC 64 (1999) 6019-6022; or Yang and Buchwald, J. of Organometallic Chem. 576 (1999) 125-146 to provide N-protected piperazines of general formula (8). N-Protected piperazines of general formula (8) can be deprotected using conditions known to those of skill in the art. For example, acidic conditions can be used to remove —C(O)OC(CH$_3$)$_3$ such as trifluoroacetic acid in methylene chloride or 4N HCl in 1,4-dioxane. Hydrogenation conditions, such as the use of palladium on carbon under 1 to 4 atmospheres of hydrogen in a solvent such as methanol, ethanol or ethyl acetate, can be used to remove —C(O)OCH$_2$Ph. Deprotected piperazines of general formula (9) can be processed as described in Scheme 1 to provide benzimidazoles of general formula (10).

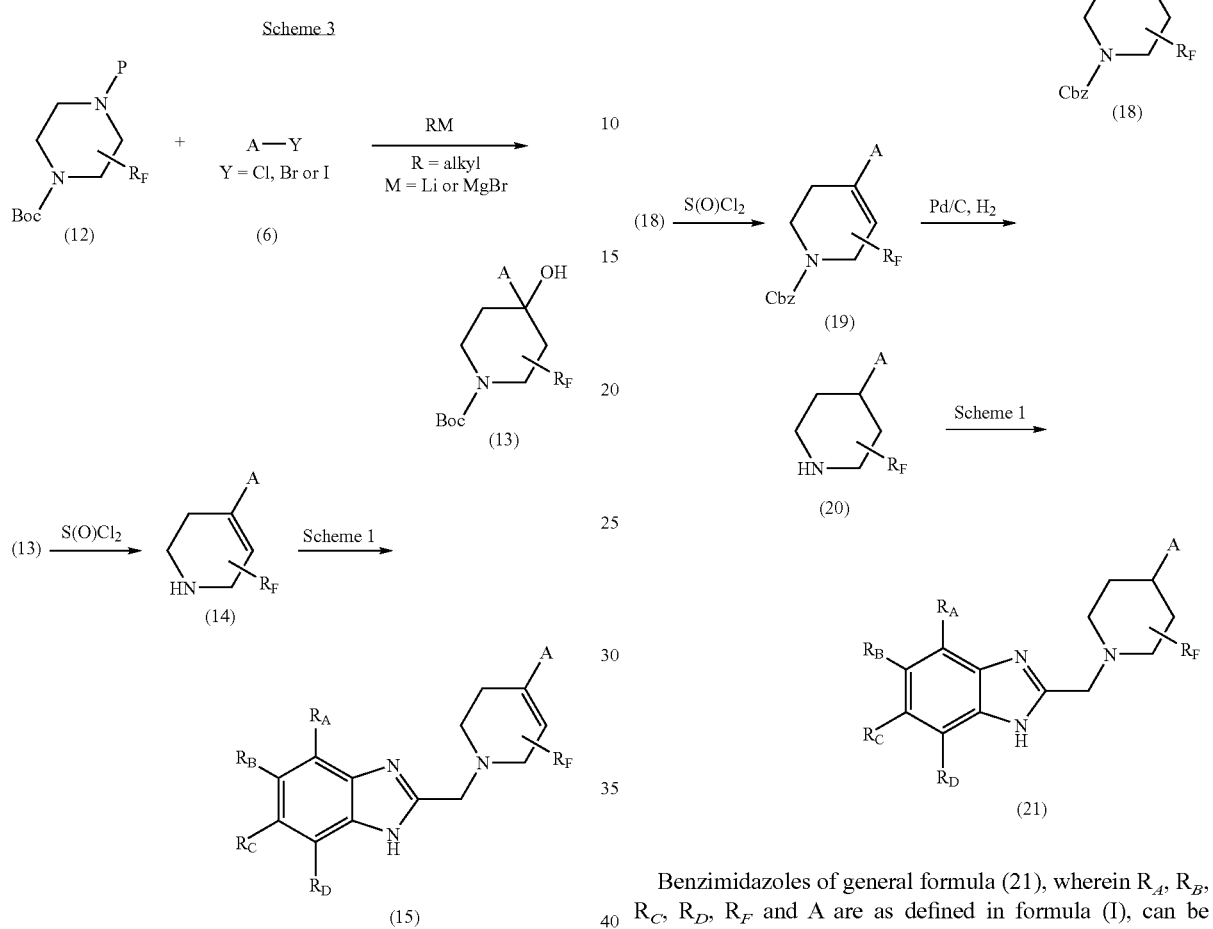

Benzimidazoles of general formula (15), wherein $R_A$, $R_B$, $R_C$, $R_D$, $R_F$ and A are as defined in formula (I), can be prepared as described in Scheme 3. tert-Butyl 4-oxopiperidine-1-carboxylate, purchased from Aldrich, can be treated with haloheterocycle of general formula (6) and an organolithium reagent or a Grignard reagent to provide alcohols of general formula (13). Alcohols of general formula (13) can be treated with thionyl chloride to provide tetrahydropyridines of general formula (14). Tetrahydropyridines of general formula (14) can be processed as described in Scheme 1 to provide benzimidazoles of general formula (15).

Benzimidazoles of general formula (21), wherein $R_A$, $R_B$, $R_C$, $R_D$, $R_F$ and A are as defined in formula (I), can be prepared as described in Scheme 4. Benzyl 4-oxopiperidine-1-carboxylate, purchased from Aldrich, can be treated with haloheterocycle of general formula (6) and an organolithium reagent or a Grignard reagent to provide alcohols of general formula (18). Alcohols of general formula (18) can be treated with thionyl chloride to provide tetrahydropyridines of general formula (19). Tetrahydropyridines of general formula (19) can be treated with a transition metal catalyst such as palladium on carbon under a hydrogen atmosphere to provide piperidines of general formula (20). Piperidines of general formula (20) can be processed as described in Scheme 1 to provide benzimidazoles of general formula (21).

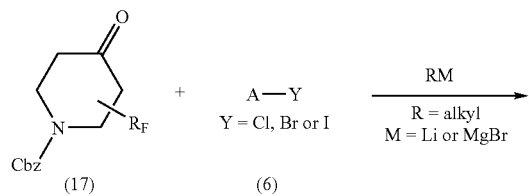

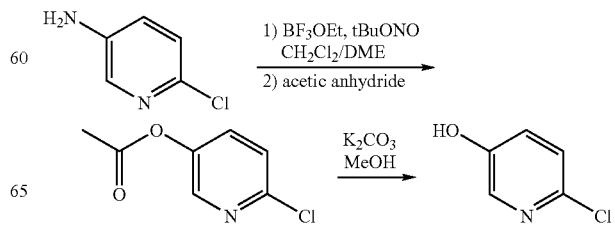

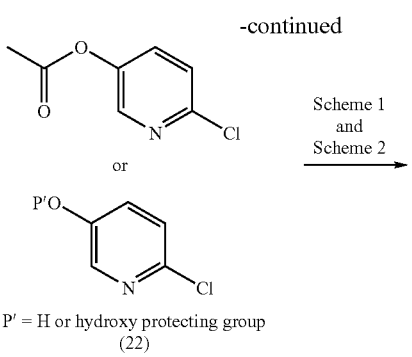

-continued

Scheme 1 and Scheme 2

P' = H or hydroxy protecting group
(22)

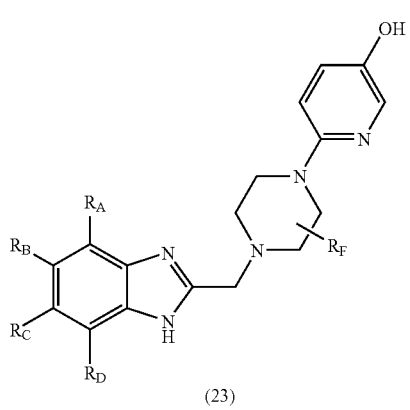

(23)

Benzimidazoles of general formula (23), wherein $R_A$, $R_B$, $R_C$, $R_D$ and $R_F$ are as defined in formula (I), can be prepared as described in Scheme 5. 5-Amino-2-chloropyridine, purchased from Aldrich, can be processed as described in Lynch et at., Tetrahedron Asymmetry 9 (1998) 2791-2794 and Koch and Schnatterer, Synthesis (1990) 499-501 to provide 6-chloropyridin-3-yl acetate and 6-chloropyridin-3-ol. 6-Chloropyridin-3-ol or 6-chloropyridin-3-yl acetate can be processed as described in Schemes 1 and 2 to provide benzimidazoles of general formula (23). Alternatively, 6-chloropyridin-3-ol can be treated with a hydroxy protecting reagent such as benzyl bromide or benzyl chloride in DMF with a base such as cesium carbonate to provide hydroxy protected chloropyridines of general formula (22) wherein P' is benzyl. Hydroxy protected chloropyridines of general formula (22) can be processed as described in Schemes 1 and 2 to provide benzimidazoles of general formula (23) following deprotection of the hydroxy protecting group using standard deprotecting methods known to those of skill in the art. For example, a benzyl hydroxy protecting group group can be removed with a transition metal catalyst such as palladium on carbon under a hydrogen atmosphere in a solvent such as methanol, ethanol or ethyl acetate.

EXAMPLE 1

2-[(4-pyridin-2-ylpiperazin-1-yl)methyl]-1H-benzimidazole maleate

EXAMPLE 1A

2-[(4-pyridin-2-ylpiperazin-1-yl)methyl]-1H-benzimidazole

To a rapidly stirred solution of 1-(2-pyridyl)piperazine (5.9 g, 36 mmol) in DMF (15 mL) in a large round bottom flask in a water bath at 20° C. was added 2-chloromethyl-benzimidazole powder (6 g, 36 mmol) over 2 minutes. Triethylamine (7.5 mL, 1.5 eq) was added, and the reaction was stirred for 16 hours, until TLC indicated complete consumption of starting material. The reaction was then treated with 5 mL of triethylamine followed by the slow dropwise addition of water (70 mL). After one hour, the precipitate was collected by suction filtration and washed with 400 mL of water and dried to give 9 grams of product. The solid was recrystallized twice from boiling n-butanol to give 7.6 grams (72% yield purified) of the title compound as a buff powder. mp 220-221° C. $^1$H NMR (d$_6$-DMSO, 300 MHz) δ 2.55 (4H, J=4.5 Hz), 3.52 (4H, J=4.5 Hz), 3.77 (s, 2H), 6.62 (1H, J=6.6, 4.5 Hz), 6.81 (1H, J=8.7 Hz), 7.14 (2H, m), 7.41-7.58 (3H, m), 8.09 (1H, J=4.5, 1.8 Hz). MS (DCI/NH$_3$) m/z 294 (M+H)$^+$. Anal. Calcd for $C_{17}H_{19}N_5$: C, 69.60; H, 6.53; N, 23.87. Found: C, 69.47; H, 6.58; N, 23.87.

EXAMPLE 1B

2-[(4-pyridin-2-ylpiperazin-1-yl)methyl]-1H-benzimidazole maleate

The product from Example 1A (1.66 g) and maleic acid (657 mg) were combined in enough ethanol to affect dissolution with mild heating. The mixture was allowed to cool to room temperature and the resultant solid was collected via filtration and crystallized from ethanol to give the maleate salt as a white powder. mp 189-190° C. Anal. Calcd for $C_{17}H_{19}N_5 \cdot C_4H_4O_4$: C, 61.60; H, 5.66; N, 17.10. Found: C, 61.42; H. 5.88; N, 17.12.

EXAMPLE 2

2-[(4-pyrimidin-2-ylpiperazin-1-yl)methyl]-1H-benzimidazole

The title compound was prepared following the procedure for Example 1A, substituting 1-(2-pyrimidyl)piperazine for 1-(2-pyridyl)piperazine and replacing DMF with CH$_3$CN as solvent. mp 198-200° C. $^1$H NMR (CD$_3$OD, 300 MHz) δ 2.60 (t, J=6 Hz, 4H), 3.86 (t, J=6 Hz, 4H), 3.85 (s, 2H), 6.58 (t, J=5 Hz, 1H), 7.23 (m, 2H), 7.52 (brm, 2H), 8.30 (d, J=5 Hz, 2H). MS (DCI/NH$_3$) m/z 295 (M+H)$^+$. Anal. Calcd for $C_{16}H_{18}N_6 \cdot (0.25 \text{ hexanes})$: C, 66.54; H, 6.86; N, 26.60. Found: C, 66.41; H, 6.91; N, 26.41.

EXAMPLE 3

2-{[4-(6-methylpyridin-2-yl)piperazin-1-yl]methyl}-1H-benzimidazole

The title compound was prepared following the procedure for Example 2, substituting 1-(6-methylpyridin-2yl)piperazine for 1-(2-pyrimidyl)piperazine. $^1$H NMR (CD$_3$OD, 300 MHz) δ 2.55 (s, 3H), 2.86 (t, J=5 Hz, 4H), 3.83 (t, J=5 Hz, 4H), 4.22 (s, 2H), 6.84 (d, J=7 Hz, 1H), 7.17 (d, J=9 Hz, 1 H), 7.59 (m, 2H), 7.79 (m, 2H), 7.92 (dd, J=7, 9 Hz, 1H). MS (DCI/NH$_3$) m/z 308 (M+H)$^+$.

EXAMPLE 4

2-[4-(1H-benzimidazol-2-ylmethyl)piperazin-1-yl]nicotinonitrile

The title compound was prepared following the procedure for Example 2, substituting 1-(3-cyanopyridin-2yl)piperazine for 1-(2-pyrimidyl)piperazine. mp 208-210° C. $^1$H NMR (CD)$_3$OD, 300 MHz) δ 2.72 (t, J=6 Hz, 4H), 3.74 (t, J=6 Hz, 4H), 3.87 (s, 2H), 6.87 (dd, J=7, 6 Hz, 1H), 7.22 (2H, m), 7.54 (brm, 1H), 7.93 (dd, J=7, 3 Hz, 1H), 8.35 (dd, J=6, 3 Hz, 1H). MS (DCI/NH$_3$) m/z 319 (M+H)$^+$. Anal. Calcd for C$_{18}$H$_{18}$N$_6$: C, 67.68; H, 5.66; N, 26.22. Found: C, 67.91; H, 5.70; N, 26.40.

EXAMPLE 5

5,7-dibromo-2-[(4-pyridin-2-ylpiperazin-1-yl)methyl]-1H-benzimidazole

The title compound was prepared following the procedures for Example 6A and Example 6B, substituting 4,6-dibromo-1,2-phenylenediamine for 4-fluoro-1,2-phenylenediamine in Example 6A. $^1$H NMR (CDCl$_3$, 300 MHz) δ 2.70 (t, J=6 Hz, 4H), 3.58 (t, J=6 Hz, 4H), 3.90 (s, 2H), 6.67 (m, 2H), 7.53 (m, 2H,), 7.65 (brm, 1H), 8.18 (m, 1H). MS (DCI/NH$_3$) m/z 450, 452, 454 (M+H)$^+$. Anal. Calcd for C$_{17}$H$_{17}$Br$_2$N$_5$: C, 45.26; H, 3.80; N, 15.52. Found: C, 44.96; H, 3.87; N, 15.26.

EXAMPLE 6

5-fluoro-2-[(4-pyridin-2-ylpiperazin-1-yl)methyl]-1H-benzimidazole

EXAMPLE 6A

5-Fluoro-2-choromethylbenzimidazole

To a 250 mL round bottom flask was added 4-fluoro-1,2-phenylenediamine (39.70 mmol, 5.0 g), chloroacetic acid (51.60 mmol, 4.87 g) and 6 N HCl (25 mL) and the mixture was heated at 95° C. for 12 hours. The mixture was cooled to room temperature and neutralized with K$_2$CO$_3$, extracted with ethyl acetate (5×, 500 mL), dried (MgSO$_4$), filtered and concentrated under reduced pressure. The product was purified on SiO$_2$ and eluted with 10% MeOH/CH$_2$Cl$_2$ to give a brown foam (2.65 g) in 36% yield. $^1$H NMR (CD$_3$OD, 300 MHz) δ 4.87 (br s, 2H), 7.05 (td, J=3.0, 9.0 Hz, 1H), 7.27 (dd, J=3.0, 9.0 Hz, 1H), 7.51-7.55 (m, 1H). MS (DCI/NH$_3$) m/z 185 (M+H)$^+$.

EXAMPLE 6B 5-fluoro-2-[(4-pyridin-2-ylpiperazin-1-yl)methyl]-1H-benzimidazole The title compound was prepared following the procedure for Example 1A, substituting 5-fluoro-2-chlorobenzimidazole for 2-chlorobenzimidazole. $^1$H NMR (CD$_3$OD, 300 MHz) δ 2.62-2.69 (t, J=5.8 Hz, 4H), 3.52-3.59 (t, J=6.0 Hz, 4H), 3.84 (s, 2H), 6.77 (dd, J=2.0, 6.0 Hz, 1H), 6.82 (d, J=9.0 Hz, 1H), 7.02 (dt, J=3.0, 9.0 Hz, 1H), 7.24 (dd, J=2.0, 9.0 Hz, 1H), 7.48-7.59 (m, 2H), 8.05-8.10 (m, 1H). MS (DCI/NH$_3$) m/z 312 (M+H)$^+$. Anal. Calcd for C$_{17}$H$_{18}$N$_5$F.0.20 MeOH: C, 65.01; H, 5.96; N, 22.04. Found: C, 64.79; H, 5.97; N, 22.17.

EXAMPLE 7

2-{[4-(1,3-thiazol-2-yl)piperazin-1-yl]methyl}-1H-benzimidazole

EXAMPLE 7A 1-(2-thiazoyl)piperazine

To a suspension of t-butyl 1-piperazinecarboxylate (2 g, 10.74 mmol) in toluene was added 2-bromothiazole (1.75 g, 10.74 mmol), cesium carbonate (6.65 g, 20.4 mmol), racemic BINAP (0.2 g, 0.32 mmol) and tris(dibenzylideneacetone-dipalladium (0) (0.2 g, 0.2 mmol). The mixture was heated to reflux for 16 hours and cooled. The reaction mixture was partitioned between water and ethyl acetate. The organic layers were combined, dried (MgSO4) and concentrated under reduced pressure. Purification using flash SiO$_2$ column provided 0.45 g (16%) of the desired N-Boc piperazine derivative as a yellow solid. The Boc-piperazine derivative (0.45 g, 1.68 mmol) was stirred with concentrated HCl (8 mL) for 10 minutes at room temperature. The reaction mixture was diluted with water, neutralized to pH 8-9 with solid Na$_2$CO$_3$ and extracted with ethyl acetate. The organic layers were combined, washed with brine and dried (Na$_2$CO$_3$) and the filtratre concentrated under reduced pressure to provide the title compound as a yellow solid (0.33 g) which was used without further purification.

EXAMPLE 7B

2-{[4-(1,3-thiazol-2-yl)piperazin-1-yl]methyl}-1H-benzimidazole

The title compound was prepared following the procedure for Example 1A, substituting 1-(2-thiazolyl)piperazine for 1-(2-pyridyl)piperazine. mp 203-205° C. $^1$H NMR (d$_6$-DMSO, 300 MHz) δ 2.58-2.62 (t, J=5.8 Hz, 4H), 3.42-3.46 (t, J=6.0 Hz, 4H), 3.79 (s, 2H), 6.84 (d, J=3.0 Hz, 1H), 7.11-7.15 (m, 2H), 6.18 (d, J=3.0 Hz, 1H), 7.42-7.46 (m, 1H), 7.53-7.57 (m, 1H). MS (DCI/NH$_3$) m/z 300 (M+H)$^+$. Anal. Calcd for C$_{15}$H$_{17}$N$_5$S.0.25 H$_2$O: C, 59.31; H, 5.77; N, 23.06. Found: C, 59.60; H, 5.97; N, 23.17.

EXAMPLE 8 isobutyl 2-[(4-pyridin-2-ylpiperazin-1-yl)methyl]-1H-benzimidazole-1-carboxylate To a stirred solution of Example 1A (0.77 g, 2.6 mmol) in dichloromethane (7 mL) was added isobutyl chloroformate (0.375 mL, 2.9 mmol). The mixture was stirred at room temperature for 16 hours, concentrated under reduced pressure and the residue was purified by flash column on SiO$_2$ eluting with 1.3% methanol/dichloromethane to give 0.5 g (49%) of the title compound as an oil. $^1$H NMR (CDCl$_3$, 300 MHz) δ 1.10 (d, J=6 Hz, 6H), 2.22 (m, 1H), 2.86 (bm, 4H), 3.67 (bm, 4H), 4.18 (bs, 2H), 4.33 (d, J=7 Hz, 2H), 6.66 (m, 2H), 7.35 (m, 2H), 7.53 (m, 1H), 7.76 (m, 1H), 7.93 (m, 1H), 8.19 (m, 1H). MS (DCI/NH$_3$) m/z 394 (M+H)$^+$.

EXAMPLE 9

2-[(4-pyridin-2-ylpiperazin-1-yl)methyl]-1-(pyrrolidin-1-ylcarbonyl)-1H-benzimidazole To a stirred solution of Example 1A (0.66 g, 2.2 mmol) in dichloromethane (7 mL) was added 1-pyrrolidinecarbonyl chloride (0.28 mL, 2.2 mmol) and triethylamine (0.625 mL, 4.5 mmol). The mixture was heated in a sealed vial for 17 hours, allowed to cool to room temperature, diluted dichloromethane, washed with 5% $NaHCO_3$, dried and concentrated under reduced pressure. The residue was purified by flash column on $SiO_2$ eluting with 20% hexanes/ethyl acetate to give 0.4 g (40%)of the title compound. mp 120-121° C. $^1$H NMR ($CDCl_3$, 300 MHz) δ 1.79-2.10 (m, 4H), 2.70 (m, 4H), 3.13 (m, 1H), 3.35-3.78 (bm, 8H), 4.32 (m, 1H), 6.65 (m, 2H), 7.30 (m, 3H), 7.49 (m, 1H), 7.76 (m, 1H), 8.28 (m, 1H). MS ($DCI/NH_3$) m/z 391 $(M+H)^+$. Anal. Calcd for $C_{22}H_{26}N_6O·½H_2O$: C, 66.14; H, 6.81; N, 21.04. Found: C, 66.22; H, 6.68; N, 21.11.

EXAMPLE 10

N,N-dimethyl-2-[(4-pyridin-2-ylpiperazin-1-yl)methyl]-1H-benzimidazole-1-carboxamide The title compound was prepared following the procedure for Example 9, substituting N,N-dimethylcarbamoyl chloride for 1-pyrrolidinecarbonyl chloride. mp 174-176° C. $^1$H NMR ($CDCl_3$, 300 MHz) δ 2.68 (bm, 4H), 2.93 (bm, 3H), 3.21 (bm, 3H), 3.48 (bm, 4H), 3.71 (bm, 1H), 4.25 (bm, 1H), 6.64 (m, 2H), 7.29 (m, 3H), 7.48 (m, 1H), 7.76 (m, 1H), 8.18 (m, 1H). MS ($DCI/NH_3$) m/z 365 $(M+H)^+$. Anal. Calcd for $C_{20}H_{24}N_6O$: C, 65.91; H, 6.64; N, 23.06. Found: C, 65.28; H, 6.56; N, 22.97.

EXAMPLE 11

2-[(4-phenylpiperazin-1-yl)methyl]-1H-benzimidazole

The title compound was prepared following the procedure for Example 2, substituting 1-phenylpiperazine for 1-(2-pyrimidyl)piperazine. mp 285-260° C. $^1$H NMR ($CD_3OD$, 300 MHz) δ 3.01 (m, 4H), 3.39 (m, 4H), 4.28 (s, 2H), 6.97 (m, 1H), 7.08 (m, 2H), 7.31 (m, 2H), 7.57 (m, 2H), 7.78 (m, 2H). MS ($DCI/NH_3$) m/z 393 $(M+H)^+$. Anal. Calcd for $C_{18}H_{20}N_4$: C, 73.94; H, 6.89; N, 19.16. Found: C, 73.76; H, 6.99; N, 19.23.

EXAMPLE 12

2-[4-(1H-benzimidazol-2-ylmethyl)piperazin-1-yl]benzonitrile

The title compound was prepared following the procedure for Example 2, substituting 1-(2-cyanophenyl)piperazine for 1-(2-pyrimidyl)piperazine. mp 236-237° C. $^1$H NMR ($CD_3OD$, 300 MHz) δ 2.77 (m, 4H), 3.27 (m, 4H), 3.89 (s, 2H), 7.07 (m, 1H), 7.15 (m, 1H), 7.23 (m, 2H), 7.56 (m, 4H). MS ($DCI/NH_3$) m/z 318 $(M+H)^+$. Anal. Calcd for $C_{19}H_{19}N_5$: C, 71.90; H, 6.03; N, 22.07. Found: C, 71.76; H, 6.03; N, 22.16.

EXAMPLE 13

2-{[4-(2-chlorophenyl)piperazin-1-yl]methyl}-1H-benzimidazole

The title compound was prepared following the procedure for Example 2, substituting 1-(2-chlorophenyl)piperazine for 1-(2-pyrimidyl)piperazine. mp 245-246° C. $^1$H NMR ($CD_3OD$, 300 MHz) δ 3.02 (m, 4H), 3.20 (m, 4H), 4.29 (s, 2H), 7.04 (m, 1H), 7.17 (dd, J=9, 2 Hz, 1H), 7.28 (m, 1H), 7.47 (dd, J=9, 2 Hz, 1H), 7.55 (m, 2H), 7.75 (m, 2H). MS ($DCI/NH_3$) m/z 327 $(M+H)^+$. Anal. Calcd for $C_{18}H_{19}ClN_4$: C, 66.15; H, 5.86; N, 17.14. Found: C, 66.07; H, 5.95; N, 17.15.

EXAMPLE 14

2-{[4-(2-fluorophenyl)piperazin-1-yl]methyl}-1H-benzimidazole

The title compound was prepared following the procedure for Example 2, substituting 1-(2-fluorophenyl)piperazine for 1-(2-pyrimidyl)piperazine. mp 262-264° C. $^1$H NMR ($CD_3OD$, 300 MHz) δ 2.96 (m, 4H), 3.24 (m, 4H), 4.26 (s, 2H), 7.06 (m, 4H), 7.55 (m, 2H), 7.66 (m, 2H). MS ($DCI/NH_3$) m/z 311 $(M+H)^+$. Anal. Calcd for $C_{18}H_{19}FN_4$: C, 69.66; H, 6.17; N, 18.05. Found: C, 69.51; H, 6.19; N, 18.12.

EXAMPLE 15

2-{[4-(2-nitrophenyl)piperazin-1-yl]methyl}-1H-benzimidazole

The title compound was prepared following the procedure for Example 2, substituting 1-(2-nitrophenyl)piperazine for 1-(2-pyrimidyl)piperazine. Purification was done using acetonitrile/TFA as the eluent on reverse phase support to give the title compound as the TFA salt. $^1$H NMR ($CD_3OD$, 300 MHz) δ 2.89 (m, 4H), 3.20 (m, 4H), 4.22 (s, 2H), 7.17 (m, 1H), 7.24 (m, 1H), 7.57 (m, 3H), 7.77 (m, 3H). MS ($DCI/NH_3$) m/z 338 $(M+H)^+$.

EXAMPLE 16

2-{[4-(2-methoxyphenyl)piperazin-1-yl]methyl}-1H-benzimidazole

The title compound was prepared following the procedure for Example 15, substituting 1-(2-methoxyphenyl)piperazine for 1-(2-nitrophenyl)piperazine. $^1$H NMR ($CD_3OD$, 300 MHz) δ 3.13 (m, 4H), 3.46 (m, 4H), 3.93 (s, 3H), 4.33 (s, 2H), 7.03 (m, 1H), 7.12 (m, 1H), 7.35 (m, 2H), 7.55 (m, 2H), 7.76 (m, 2H). MS ($DCI/NH_3$) m/z 323 $(M+H)^+$.

EXAMPLE 17

4-[4-(1H-benzimidazol-2-ylmethyl)piperazin-1-yl]phenol

The title compound was prepared following the procedure for Example 2, substituting 1-(4-hydroxyphenyl)piperazine for 1-(2-pyrimidyl)piperazine. mp 206-209° C. $^1$H NMR ($CD_3OD$, 300 MHz) δ 3.12 (m, 4H), 3.55 (m, 4H), 4.32 (s, 2H), 6.93 (m, 2H), 7.32 (m, 2H), 7.60 (m, 2H), 7.80 (m, 2H). MS ($DCI/NH3$) m/z 309 $(M+H)^+$.

EXAMPLE 18

2-({4-[2-(methylthio)phenyl]piperazin-1-yl}methyl)-1H-benzimidazole

The title compound was prepared following the procedure for Example 2, substituting 1-(2-methylthiophenyl)piperazine for 1-(2-pyrimidyl)piperazine. mp 214-216° C. $^1$H NMR (CDCl$_3$, 300 MHz) δ 2.14 (s, 3H), 2.77 (m, 4H), 3.07 (m, 4H), 3.94 (s, 2H), 7.06 (m, 1H), 7.12 (m, 3H), 7.25 (m, 2H), 7.59 (m, 2H). MS (DCI/NH$_3$) m/z 339 (M+H)$^+$. Anal. Calcd for C$_{19}$H$_{22}$N$_4$O.¼ H$_2$O: C, 66.54; H, 6.61; N, 16.34. Found: C, 66.23: H, 6.54; N, 16.36.

EXAMPLE 19

2-{[4-(2-ethoxyphenyl)piperazin-1-yl]methyl}-1H-benzimidazole

The title compound was prepared following the procedure for Example 2, substituting 1-(2-ethoxyphenyl)piperazine for 1-(2-pyrimidyl)piperazine. mp 95-100° C. $^1$H NMR (CDCl$_3$, 300 MHz) δ 1.45 (t, J=6 Hz, 3H), 2.39 (m, 4H), 3.33 (m, 4H), 4.03 (s, 2H), 4.07 (q, J=6 Hz, 2H), 6.83-7.03 (m, 3H), 7.26 (m, 3H), 7.60 (m, 2H). MS (DCI/NH$_3$) m/z 337 (M+H)$^+$. Anal. Calcd for C$_{20}$H$_{24}$N$_4$O: C, 71.40; H, 7.19; N, 16.65. Found: C, 68.97; H, 6.90, N, 16.01.

EXAMPLE 20

2-[4-(1H-benzimidazol-2-ylmethyl)piperazin-1-yl]phenol

The title compound was prepared following the procedure for Example 2, substituting 1-(2-hydroxyphenyl)piperazine for 1-(2-pyrimidyl)piperazine. mp 208-216° C. $^1$H NMR (CDCl$_3$, 300 MHz) δ 2.78 (m, 4H), 2.97 (m, 4H), 3.93 (s, 2H), 6.83-6.95 (m, 2H), 7.05 (m, 1H), 7.14 (dd, J=7, 2 Hz, 1H), 7.59 (m, 2H). MS (DCI/NH$_3$) m/z 309 (M+H)$^+$. Anal. Calcd for C$_{18}$H$_{20}$N$_4$O.½H$_2$O: C, 68.12; H, 6.67; N, 17.65. Found: C, 68.34; H, 6.53; N, 17.28.

EXAMPLE 21

2-{[4-(2-methoxyphenyl)piperidin-1-yl]methyl}-1H-benzimidazole

A mixture of 4-(2-methoxyphenyl)piperidine (0.2 g, 1.06 mmol), 2-chloromethyl-benzimidazole (186, 1.1 mmol) and Cs$_2$CO$_3$ (0.36 g, 0.36 mmol) in DMF (8 mL) were stirred at room temperature for 18 hours. The reaction mixture was poured into water (30 mL) and extracted with ethyl acetate (20 mL). The organic layer was washed with brine (2×30 mL) and dried over MgSO$_4$, filtered and the filtrate concentrated under reduced pressure. The residue was purified by flash chromatography eluting with 5% methanol in dichloromethane to give the title compound (82 mg, 25%). $^1$H NMR (CDCl$_3$, 300 MHz) δ 1.69 (m, 4H), 2.19 (m, 2H), 2.87(m, 1H), 2.96 (m, 2H), 3.75 (s, 2H), 3.77 (s, 3H), 6.92 (m, 2H), 7.15 (m, 4H), 7.45 (m, 1H), 7.55 (m, 1H), 12.26 (s, 1H). MS (DCI-NH$_3$) m/z 322 (M+H)$^+$.

EXAMPLE 22

2-[(4-pyridin-2-ylpiperidin-1-yl)methyl]-1H-benzimidazole

EXAMPLE 22A benzyl 4-hydroxy-4-pyridin-2-ylpiperidine-1-carboxylate

A solution of 2-bromopyridine (0.47 mL, 5 mmol) in THF (20 mL) was cooled to −60° C. and treated dropwise with nBuLi (1.6M in hexanes, 5.2 ml, 5.2 mmol). The reaction mixture was stirred for 30 minutes at −60° C. and then benzyl 4-oxo-1-piperidine carboxylate 1.14 g, 4.9 mmol) in THF (10 mL) was slowly added to the reaction mixture. The reaction mixture was stirred at −60° C. for 15 minutes and then quenched with saturated NH$_4$Cl. The cooling bath was removed and reaction mixture was allowed to warm to room temperature. The mixture was were extracted with CH$_2$Cl$_2$ and the organics were dried (MgSO$_4$), filtered and the filtrate concentrated under reduced pressure. The residue was purified by flash chromatography using hexane:ethyl acetate (1:1) to provide the title compound, 400 mg (27%). $^1$H NMR (d$_6$-DMSO, 300 MHz) δ 1.54 (m, 4H), 2.05 (m, 4 H), 3.25 (m, 4H), 3.95 (m, 4H), 5.11 (s, 2H), 5.35 (s, 1H), 7.25 (m, 2H), 7.35 (m, 5H), 7.68 (m, 1H), 7.79 (m, 1H), 8.5 (m, 1H); MS (DCI/NH$_3$) m/z 313 (M+H)$^+$.

EXAMPLE 22B 4-(pyrid-2yl)piperidine

The product from Example 22A (0.4 g, 1.28 mmol) in thionyl chloride (6 mL) was refluxed for 3 hours, allowed to cool to room temperature and concentrated under reduced pressure. The residue was treated with ice and 40% NaOH and then extracted with CH$_2$Cl$_2$. The organics were separated, washed with brine, dried (Na$_2$SO$_4$), filtered and the filtrate concentrated to give 332 mg of dehydration product.

The crude dehydration product was then hydrogenated using 10% Pd/C (250 mg) at 60 psi and 50° C. for 40 hours to give the title compound (150 mg 88%). MS (DCI/NH$_3$) m/z 163 (M+H)$^+$.

EXAMPLE 22C

2-[(4-pyridin-2-ylpiperidin-1-yl)methyl]-1H-benzimidazole

The product from Example 22B (0.6 g, 0.36 mmol), 2-chloromethyl-benzimidazole (0.62 g, 0.36 mmol) and Cs$_2$CO$_3$ (0.12 g, 0.36 mmol) in DMF (8 mL) were stirred at room temperature for 18 hours. The reaction mixture was poured into water (30 mL) and extracted with ethyl acetate (20 mL). The organic layer was washed with brine (2×30 mL), dried over MgSO$_4$, filtered and the filtrate concentrated under reduced pressure. The residue was purified by flash chromatography eluting with 5% MeOH/CH$_2$Cl$_2$ to give the title compound (11.2 mg, 11%). $^1$H NMR (CDCl$_3$, 300 MHz) δ 2.0 (m, 5H), 2.51 (m, 2H), 2.79 (m, 1H), 3.14 (m, 2H), 4.01 (s, 2H), 7.09 (m, 3H), 7.29 (m, 1H), 7.55 (m, 3H), 8.49 (m, 1H). MS (DCI/NH$_3$) m/z 293 (M+H)$^+$.

EXAMPLE 23

2-[(4-phenyl-3,6-dihydropyridin-1(2H)-yl)methyl]-1H-benzimidazole

The title compound was prepared as described in Example 22C except substituting 4-phenyl-1,2,3,6-tetrahydropyridine hydrochloride for 4-(pyridin-2yl)piperidine. $^1$H NMR (CD$_3$OD+1 drop of CDCl$_3$+1 drop of TFA, 300 MHz) 62.90 (m, 2H), 3.52 (t, 2H), 3.92 (m, 2H), 4.7 (s, 2H), 6.14 (m, 1H), 7.34 (m, 3H), 7.46 (m, 2H), 7.52 (m, 2H), 7.78 (m, 2H). MS (DCI/NH$_3$) m/z 290 (M+H)$^+$.

EXAMPLE 24

2-[(2-methyl-4-pyridin-2-ylpiperazin-1-yl)methyl]-1H-benzimidazole

EXAMPLE 24A

3-methyl-1-pyridin-2-ylpiperazine hydrobromide

2-Methylpiperazine (1.0 g, 0.01 mol, racemic mixture) and 2-bromopyridine (10 mL, 0.1 mol) were combined and heated at 120° C. for 16 hours. The reaction mixture was cooled to 23° C. and partitioned between ethyl acetate and water. The layers were separated, and the water layer was concentrated under reduced pressure. The residue was triturated with ethyl acetate, dichloromethane, and methanol to afford 460 mg (26% yield) of the title compound as an off-white solid. $^1$H NMR (300 MHz, DMSO-d$_6$) δ 1.27 (d, J=6.6 Hz, 3H), 2.90 (dd, J=10.5, 14.1 Hz, 1H), 3.10 (m, 2H), 3.40 (m, 2H), 4.32 (m, 2H), 6.77 (dd, J=4.8, 6.9 Hz, 1H), 6.98 (d, J=8.1 Hz, 1H), 7.64 (m, 1H), 8.15 (m, 1H), 8.63 (bs, 1H), 8.92 (bs, 1H); MS (APCI) m/e 178 (M+H)$^+$.

EXAMPLE 24B

2-[(2-methyl-4-pyridin-2-ylpiperazin-1-yl)methyl]-1H-benzimidazole

The product from Example 24A (0.50 g, 1.93 mmol) in N,N-dimethylformamide (10 mL) at 0° C. was slowly treated with a solution of 2-chloromethyl-1H-benzimidazole (0.31 g, 1.83 mmol) in N,N-dimethylformamide (10 mL). After 5 minutes, the mixture was treated with cesium carbonate (0.60 mmol, 1.83 mmol) and the cooling bath was removed. After 1 hour, the reaction mixture was diluted with ethyl acetate and washed with water (3×) and brine, dried over Na$_2$SO$_4$, filtered, and the filtrate concentrated under reduced pressure. The residue was chromatographed on flash silica gel (2% methanol/dichloromethane) to afford 201 mg (36% yield) of the title compound. mp 207-209° C.; $^1$H NMR (300 MHz, DMSO-d$_6$) δ 1.18 (d, J=6.0 Hz, 3H), 2.38 (m, 1H), 2.52 (m, 1H), 2.78 (m, 2H), 3.02 (m, 1H), 3.67 (d, J=14.4 Hz, 1H), 3.97 (m, 2H), 4.08 (d, J=14.4 Hz, 1H), 6.62 (dd, J=5.1, 6.9 Hz, 1H), 6.81 (d, J=8.4 Hz, 1H), 7.14 (m, 2H), 7.50 (m, 3H), 8.08 (m, 1H), 12.22 (bs, 1H); MS (ESI) m/e 308 (M+H)$^+$; Anal. calcd for C$_{18}$H$_{21}$N$_5$: C, 70.33; H, 6.89; N, 22.78. Found: C, 70.15; H, 6.92; N, 22.46.

EXAMPLE 25

2-{[(2S)-2-methyl-4-pyridin-2-ylpiperazin-1-yl]methyl}-1H-benzimidazole

EXAMPLE 25A

(3S)-3-methyl-1-pyridin-2-ylpiperazine (S)-(+)-2-Methylpiperazine (0.50 g, 0.005 mol, Aldrich) and 2-bromopyridine (5 mL, 0.05 mol) were combined and heated at 120° C. for 14 hours. The reaction mixture was allowed to cool to 23° C. and partitioned between ethyl acetate and water. The layers were separated, and the water layer extracted twice with ethyl acetate. The aqueous phase was brought to pH ~11 with a solution of saturated sodium bicarbonate and solid sodium carbonate. Sodium chloride was added, and the saturated aqueous solution was extracted with ethyl acetate (2×) and dichloromethane (2×). The combined organic extracts were dried over Na$_2$SO$_4$, filtered, and the filtrate concentrated under reduced pressure to afford 0.6 g (67% yield) of the title compound. $^1$H NMR (400 MHz, DMSO-d$_6$) δ 1.02 (d, J=6.0 Hz, 3H), 2.27 (dd, J=10, 12 Hz, 1), 2.67 (m, 3H), 2.92 (m, 1H), 4.07 (m, 2H), 6.58 (dd, J=6, 8 Hz, 1H), 6.77 (d, J=8 Hz, 1H), 7.49 (m, 1H), 8.08 (m, 1H); MS (ESI) m/e 178 (M+H)$^+$.

EXAMPLE 25B

2-{[(2S)-2-methyl-4-pyridin-2-ylpiperazin-1-yl]methyl}-1H-benzimidazole

The product of Example 25B (0.24 g, 1.33 mmol) in N,N-dimethylformamide (10 mL) was treated with 2-chloromethyl-1H-benzimidazole (0.21 g, 1.27 mmol) and cesium carbonate (0.41 mmol, 1.27 mmol) at 23° C. with stirring for 3 hours. The reaction mixture was diluted with ethyl acetate and washed with water (3×) and brine, dried over Na$_2$SO$_4$ filtered, and the filtrate concentrated under reduced pressure. The residue was chromatographed on flash silica gel (1-3% methanol/dichloromethane gradient) to afford 178 mg (46% yield) of the title compound as a light yellow solid. mp 149-151° C.; $^1$H NMR (400 MHz, DMSO-d$_6$) δ 1.18 (d, J=6 Hz, 3H), 2.38 (m, 1H), 2.53 (m, 1H), 2.76 (dd, J=8, 11.2 Hz, 1H), 2.83 (m, 1H), 3.03 (m, 1H), 3.69 (d, J=14 Hz, 1H), 3.94 (m, 1H), 4.00 (m, 1H), 4.07 (d, J=14 Hz, 1H), 6.60 (dd, J=4.8, 6.4 Hz, 1H), 6.80 (d, J=8.4 Hz, 1H), 7.13 (m, 2H), 7.60 (m, 3H), 8.08 (m, 1H), 12.22 (bs, 1H); MS (ESI) m/e 308 (M+H)$^+$; Anal. calcd for C$_{18}$H$_{21}$N$_5$: C, 70.33; H, 6.89; N, 22.78. Found: C, 70.21; H, 6.77; N, 22.62.

EXAMPLE 26

2-{[(2R)-2-methyl-4-pyridin-2-ylpiperazin-1-yl]methyl}-1H-benzimidazole

EXAMPLE 26A

(3R)-3-methyl-1-pyridin-2-ylpiperazine (R)-(−)-2-Methylpiperazine (0.50 g, 0.005 mol, Aldrich) and 2-bromopyridine (5 mL, 0.05 mol) were combined and heated at 120° C. for 14 hours. The reaction mixture was allowed to cool to 23° C. and partitioned between a large volume of ethyl acetate and water. The layers were separated, and then additional water was added to the ethyl acetate solution. Drops of 1 N HCl solution were added to the water/ethyl acetate mixture with vigorous mixing. The layers were separated, and the combined aqueous phases were basified to pH ~11 with a solution of saturated sodium bicarbonate and solid sodium carbonate. Sodium chloride was added, and the saturated aqueous solution was extracted with chloroform containing a few drops of isopropyl alcohol (5×). The combined organic extracts were dried over $Na_2SO_4$, filtered, and the filtrate concentrated under reduced pressure to afford 0.79 g (89% yield) of the title compound. $^1H$ NMR (400 MHz, DMSO-$d_6$) δ 1.02 (d, J=6.0 Hz, 3H), 2.27 (dd, J=10, 12 Hz, 1), 2.67 (m, 3H), 2.92 (m, 1H), 4.07 (m, 2H), 6.58 (dd, J=6, 8 Hz, 1H), 6.77 (d, J=8 Hz, 1H), 7.49 (m, 1H), 8.08 (m, 1H); MS (ESI) m/e 178 (M+H)$^+$.

EXAMPLE 26B

2-{[(2R)-2-methyl-4-pyridin-2-ylpiperazin-1-yl]methyl}-1H-benzimidazole

The product of Example 26A (0.79 g, 4.43 mmol) and N,N-dimethylformamide (15 mL) at 0° C. was treated with a solution of the 2-chloromethyl-1H-benzimidazole (0.70 g, 4.21 mmol) in N,N-dimethylformamide (15 mL). After 10 minutes, the mixture was treated with cesium carbonate (1.37 mmol, 4.21 mmol) and the cooling bath was removed. After 1 hour, the reaction mixture was diluted with ethyl acetate and washed with water (3×) and brine, dried over $Na_2SO_4$, filtered, and the filtrate concentrated under reduced pressure. The residue was chromatographed on flash silica gel (1-3% methanol/dichloromethane gradient) to afford 0.50 g (39% yield) of the title compound as a light yellow solid. mp 151-153° C.; $^1H$ NMR (400 MHz, DMSO-$d_6$) δ 1.18 (d, J=6 Hz, 3H), 2.38 (m, 1H), 2.53 (m, 1H), 2.76 (dd, J=8, 11.2 Hz, 1H), 2.83 (m, 1H), 3.03 (m, 1H), 3.69 (d, J=14 Hz, 1H), 3.94 (m, 1H), 4.00 (m, 1H), 4.07 (d, J=14 Hz, 1H), 6.60 (dd, J=4.8, 6.4 Hz, 1H), 6.80 (d, J=8.4 Hz, 1H), 7.13 (m, 2H), 7.60 (m, 3H), 8.08 (m, 1H), 12.22 (bs, 1H); MS (ESI) m/e 308 (M+H)$^+$; Anal. calcd for $C_{18}H_{21}N_5$: C, 70.33; H, 6.89; N, 22.78. Found: C, 70.10; H, 7.03; N, 22.63.

EXAMPLE 27

N-{2-[4-(1H-benzimidazol-2-ylmethyl)piperazin-1-yl]pyridin-3-yl}methanesulfonamide

EXAMPLE 27A

N-(2-chloropyridin-3-yl)methanesulfonamide

2-Chloro-pyridin-3-ylamine (1.00 g, 7.75 mmol) in dichloromethane (20 mL) at 23° C. was treated with methane sulfonyl chloride (2.23 g, 19.4 mmol) and triethylamine (1.96 g, 19.4 mmol). After stirring for 48 hours, the reaction mixture was diluted with water, the layers were separated, and the aqueous phase was extracted with dichloromethane (2×). The organic layers were combined, dried over $MgSO_4$, filtered, and the filtrate concentrated under reduced pressure. The residue was chromatographed on flash silica gel (20% ethyl acetate:hexanes), concentrated under reduced pressure, and added to a 10% aqueous sodium hydroxide solution (32 mL). The solution was stirred vigorously for about 0.5 hours until homogeneous. The solution was then neutralized to pH~7 with 2N HCl, saturated with $Na_2SO_4$, and extracted with ethyl acetate (3×). The combined extracts were dried over $Na_2SO_4$, filtered, and the filtrate concentrated under reduced pressure to afford 1.5 g (93% yield) of the title compound. References: Tetrahedron Letters 38, 26, 4667-4670, 1997; Eur. J. Org. Chem. 2000, 1263-1270. $^1H$ NMR (300 MHz, DMSO-$d_6$) δ 3.12 (s, 3H), 7.46 (dd, J=4.5, 8.4 Hz, 1H), 7.89 (dd, J=1.5, 8.4 Hz, 1H), 8.27 (dd, J=1.5, 4.5 Hz, 1H), 9.72 (bs, 1H); MS (ESI) m/e 205 (M)$^-$.

EXAMPLE 27B

N-(2-piperazin-1-ylpyridin-3-yl)methanesulfonamide

Piperazine (5.2 g, 60.2 mmol), the product from Example 27A (1.24 g, 6.02 mmol), and n-butanol (90 mL) were combined and refluxed for 3 days. The reaction mixture was allowed to cool to 23° C. and concentrated under reduced pressure. The residue was chromatographed on flash silica gel (33% methanol/dichloromethane with 1% acetic acid) to afford 2.0 g (~88% yield) the title compound. $^1H$ NMR (300 MHz, $CD_3OD$) δ1.97 (s, $CH_3$ from $CH_3CO_2H$), 3.13 (s, 3H), 3.42 (m, 8H), 7.13 (dd, J=4.5, 8.4 Hz, 1H), 7.78 (dd, J=1.5, 8.4 Hz, 1H), 8.12 (dd, J=1.5, 4.5 Hz, 1H); MS (DCI/$NH_3$) m/e 257 (M+H)$^+$.

EXAMPLE 27C

N-{2-[4-(1H-benzimidazol-2-ylmethyl)piperazin-1-yl]pyridin-3-yl}methanesulfonamide The product from Example 27B (0.066 g, 0.21 mmol) and cesium carbonate (0.137 g, 0.42 mmol) were combined in N,N-dimethylformamide (2 mL) at 23° C. and stirred for 5 minutes. The mixture was then treated with 2-chloromethyl-1H-benzimidazole (0.035 g, 0.21 mmol). After 1 hour, the reaction mixture was concentrated under reduced pressure. The residue was impregnated onto flash silica gel and chromatographed on flash silica gel (10% methanol/dichloromethane) to afford 22 mg (27% yield) of the title compound. $^1H$ NMR (500 MHz, DMSO-$d_6$) δ 2.64 (m, 4H), 3.12 (s, 3H), 3.23 (m, 4H), 3.79 (s, 2H), 5.75 (s, 2H), 6.98 (dd, J=5, 8.5 Hz, 1H), 7.14 (m, 2H), 7.44 (bd, J=7.5 Hz, 1H), 7.57 (bd, J=7.5 Hz, 1H), 7.58 (dd, J=1, 7 Hz, 1H), 8.08 (dd, J=1, 5 Hz, 1H), 8.76 (bs, 1H); MS (ESI) m/e 387 (M+H)$^+$.

EXAMPLE 28

2-{[4-(3-fluoropyridin-2-yl)piperazin-1-yl]methyl}-1H-benzimidazole

EXAMPLE 28A 2-chloro-3-fluoropyridine 1,4-Diazabicyclo[2.2.2]octane (5.78 g, 51.5 mmol) in diethyl ether (130 mL) was treated dropwise with n-butyllithium (32.2 mL, 51.5 mmol, 1.6M solution in hexanes) at –78 ° C. The reaction mixture was warmed to –20° C. for 1 hour and then recooled to –78° C. The recooled mixture was treated with 3-fluoropyridine (5.0 g, 51.5 mmol) in diethyl ether (5 mL) dropwise. After stirring for 2 hours at –78° C., the mixture was treated with hexachloroethane (12.2 g, 51.5 mmol) in tetrahydrofuran (24 mL). After stirring for one hour at –78° C., the reaction mixture was treated with a solution of water (15 mL) and tetrahydrofuran (25 mL). The reaction mixture was warmed to 0° C. and, after 30 minutes, additional water and diethyl ether were added to the mixture. The layers were separated and the aqueous phase extracted with diethyl ether (2×). The combined ethereal layers were dried over $Na_2SO_4$, filtered, and the filtrate concentrated under reduced pressure. The residue was chromatographed on flash silica gel (10% ethyl acetate/hexanes) to afford 3.5 g (52% yield) of the title compound. $^1$H NMR (300 MHz, DMSOd$_6$) δ 7.54 (m, 1H), 7.96 (m, 1H), 8.31 (m, 1H); MS (ESI) m/e 154 (M+Na)$^+$.

EXAMPLE 28B 1-(3-fluoropyridin-2-yl)piperazine

The product of Example 28A (3.3 g, 0.025 mol) in n-butanol (150 mL) at 23° C. was treated with piperazine (21.5 g, 0.25 mol) and then reflux for 3 days. The reaction mixture was allowed to cool to 23° C. and concentrated under reduced pressure. The residue was slurried with water and ethyl acetate. The ethyl acetate solution was separarted, dried over Na$_2$SO$_4$, filtered, and the filtrate concentrated under reduced pressure to afford 3.3 g (73% yield) of the title compound. $^1$H NMR (500 MHz, DMSO-d$_6$) δ 2.80 (m, 4H), 3.38 (m, 4H), 6.84 (m, 1H), 7.47 (m, 1H), 7.98 (m, 1H); MS (ESI) m/e 182 (M+H)$^+$.

EXAMPLE 28C

2-{[4-(3-fluoropyridin-2-yl)piperazin-1-yl]methyl}-1H-benzimidazole

The product of Example 28B (0.50 g, 2.76 mmol), 2-chloromethyl-1H-benzimidazole (0.48 g, 2.90 mmol), and cesium carbonate (1.8 g, 5.52 mmol) were combined in N,N-dimethylformamide (28 mL) at 23° C. and stirred for 1.25 hours. The mixture was concentrated under reduced pressure and rinsed with 10% methanol/dichloromethane. The solid was filtered off and the filtrate concentrated under reduced pressure. The residue was impregnated onto flash silica gel and chromatographed on flash silica gel (10% methanol/dichloromethane) to afford 311 mg (36% yield) of the title compound. mp 210-212°° C.; $^1$H NMR (300 MHz, DMSO-d$_6$) δ 2.62 (m, 4H), 3.43 (m, 4H), 3.78 (s, 2H), 6.87 (m, 1H), 7.14 (m, 2H), 7.50 (m, 3H), 8.00 (m, 1H); MS (APCI) m/e 312 (M+H)$^+$; Anal. calcd for C$_{17}$H$_{18}$FN$_5$ 0.4 H$_2$O: C, 64.10; H, 5.95; N, 21.98. Found: C, 64.16; H, 5.86; N, 21.95.

EXAMPLE 29

6-[4-(1H-benzimidazol-2-ylmethyl)piperazin-1-yl]pyridin-3-ol

EXAMPLE 29A 5-(benzyloxy)-2-chloropyridine

2-Chloro-5-hydroxypyridine (2.6 g, 20 mmol) and cesium carbonate (7.2 g, 22 mmol) in 8 mL of DMF were treated with benzyl bromide (2.6 mL). After stirring at 23° C. for 6 hours, the reaction mixture was diluted with water, adjusted to pH 7 with saturated aqueous NaH$_2$PO$_4$, and extracted with dichloromethane. The organic extract was dried over Na$_2$SO$_4$ filtered and the filtrate concentrated under reduced pressure. The residue was purified by flash chromatography (eluting with CH$_2$Cl$_2$) to provide the title compound as a white solid (3.44 g, 79%). mp<50° C.; R$_f$=0.4 (CH$_2$Cl$_2$); MS 220 (M+H)$^+$; $^1$H NMR (300 MHz, DMSO-d$_6$) δ 8.20 (d, 1H, J=2.7 Hz), 7.55 (dd, 1H, J=9, 2.7 Hz), 7.3-7.5 (m, 6H), 5.19 (s, 2H).

EXAMPLE 29B tert-butyl 4-[5-(benzyloxy)pyridin-2-yl]piperazine-1-carboxylate

The product from Example 29A (2.63 g), Pd$_2$(dba)$_3$ (0.33 g), racemic BINAP (0.45 g), sodium tert-butoxide (2.3 g), and tert-butyl piperazine-1-carboxylate (4.46 g) were combined in toluene (80 mL) and heated at 95° C. for 3 hours. The reaction mixture was treated with toluene (50 mL) and diethyl ether (200 mL). The mixture was washed with water and the organic phase was dried over Na$_2$SO$_4$, filtered, and the filtrate concentrated under reduced pressure. The residue was purified by flash chromatography, eluting with 1:4 ethyl acetate/hexans to provide the title compound (4.06 g, 92%). mp 93-94° C.; R$_f$=0.21 (1:4 ethyl acetate/hexanes); MS 370 (M+H)$^+$.

EXAMPLE 29C

1-[5-(benzyloxy)pyridin-2-yl]piperazine

The product from Example 29B (1.96 g) was treated with trifluoroacetic acid (3.5 mL) with stirring at 23° C. for 2 hours. The mixture was partitioned between CH$_2$Cl$_2$ (100 mL)/n-butanol (5 mL) and water (400 mL)/NH$_4$OH (5 mL). The organic phase was separated, dried over Na$_2$SO$_4$, filtered, and the filtrate concentrated under reduced pressure to provide the title compound as a white powder which was used in the next step without further purification.

EXAMPLE 29D 2-({4-[5-(benzyloxy)pyridin-2-yl]piperazin-1-yl}methyl)-1H-benzimidazole The product from Example 29C and 2-chloromethyl-1H-benzoimidazole (0.88 mg) were combined and dissolved in DMF (7 mL)/triethylamine (1.5 mL). After stirring at 23° C. for 2 hours, the mixture was treated with acetonitrile (20 mL) and then allowed to stir for 24 hours. The reaction mixture was partitioned between CH$_2$Cl$_2$ (100 mL)/n-butanol (5 mL) and water (800 mL)/NH$_4$OH (5 mL). The organic phase was separated, dried over Na$_2$SO$_4$, filtered, and the filtrate concentrated under reduced pressure. The residue was purified by flash chromatography to provide the title as a white solid (1.169 g (55%). mp 62-64° C.; R$_f$=0.26 (95:5 CH$_2$Cl$_2$:methanol:0.1% NH$_4$OH); MS 400 (M+H)$^+$; $^1$H NMR (300 MHz, DMSO-d$_6$) δ 12.3 (bs, NH, 1H), 7.90 (d, 1H, J=3 Hz), 7.55 (m, 1H), 7.3-7.5 (m, 8H), 7.15 (m, 2H), 6.80 (d, 1H, J=9 Hz), 5.05 (s, 2H), 3.76 (s, 2H), 3.39 (t, 4H, J=5.1 Hz), 2.57 (t, 4H, J=5.1 Hz).

EXAMPLE 29E

6-[4-(1H-benzimidazol-2-ylmethyl)piperazin-1-yl]pyridin-3-ol

The product from Example 29D (800 mg) in ethyl acetate (35 mL) was treated with 10% palladium on carbon (85 mg) under a blanket of hydrogen gas at 23° C. until TLC indicated consumption of starting material. The mixture was filtered and the filter cake washed with with methanol and CH$_2$Cl$_2$. The filtrates were combined and concentrated under reduced pressure. The residue was purified by flash chromatography (eluting with 90:10:0.1 CH$_2$Cl$_2$:methanol:NH$_4$OH) to provide the title compound pure as a white solid (566 mg, 92%). mp 144-145° C.; $R_f$=0.08; (95:5 $CH_2Cl_2$: methanol:0.1% $NH_4OH$); MS 310 (M+H)$^+$; $_1$H NMR (300 MHz, MeOD) δ 7.72 (d, 1H, J=2.7 Hz), 7.53 (m, 2H), 7.21 (m, 2H), 7.12 (dd, 1H, J=9, 3 Hz), 6.75 (d, 1H, J=9 Hz), 3.85 (s, 2H), 3.40 (t, 4H, J=5.1 Hz) 2.69 (t, 4H, J=5.1 Hz); Analysis calculated for $C_{17}H_{19}N_5O$ (1.0 equivalent methanol, 0.1 equivalent dichloromethane): C, 62.13; H, 6.68; N, 20.01. Found: C, 62.04; H, 6.57; N, 19.67.

EXAMPLE 30

2-{[4-(3-methylpyridin-2-yl)piperazin-1-yl]methyl}-1H-benzimidazole

The title compound can be prepared following the procedure for Example 2, substituting 1-(3-methylpyridin-2yl)piperazine for 1-(2-pyrimidyl)piperazine.

In Vivo Data Rat Penile Erection Model

Wistar rats were used as a primary animal model to study penile erection in vivo. All experiments were carried out between 9:00 AM and 3:00 PM in a diffusely illuminated testing room with a red light. Animals were weighed and allowed to adapt to the testing room for 60 minutes before the beginning of experiments. Rats were placed individually in a transparent cage (20×30×30 cm) after drug injection. The number of penile erections were recorded by direct observation for a period of 60 minutes after drug dosing, and the number of animals exhibiting 1 or more erections is expressed as incidence (%).

TABLE 1

Induced Penile Erection in Rats for
2-[(4-pyridin-2-ylpiperazin-1-yl)methyl]-1H-benzimidazole

| Dose (μmol/kg) | Incidence (%) |
| --- | --- |
| vehicle | 25 |
| 0.003 | 25 |
| 0.01 | 50 |
| 0.03 | 83 |
| 0.10 | 58 |

(L)-Ascorbic acid in saline (1 mg/mL) was used as vehicle. Twelve animals were used per dose. Apomorphine was used as a positive control at a dose of 0.1 μmol/kg which resulted in an 83% incidence of rat penile erections.

The data in Table 1 demonstrates that 2-[(4-pyridin-2-ylpiperazin-1-yl)methyl]-1H-benzimidazole induced statistically significant penile erections in rats after subcutaneous administration for doses of 0.01 μmol/kg to 0.10 μmol/kg.

TABLE 2

Induced Penile Erection in Rats for
6-[4-(1H-benzimidazol-2-ylmethyl)piperazin-1-yl]pyridin-3-ol

| Dose (μmol/kg) | Incidence (%) |
| --- | --- |
| vehicle | 25 |
| 0.01 | 42 |
| 0.03 | 58 |
| 0.1 | 58 |
| 0.3 | 33 |

(L)-Ascorbic acid in saline (1 mg/mL) was used as vehicle. Twelve animals were used per dose. Apomorphine was used as a positive control at a dose of 0.1 μmol/kg which resulted in an 93% incidence of rat penile erections.

The data in Table 2 demonstrates that 6-[4-(1H-benzimidazol-2-ylmethyl)piperazin-1-yl]pyridin-3-ol induced statistically significant penile erections in rats after subcutaneous administration for doses of 0.01 μmol/kg to 0.10 μmol/kg.

Preferred compounds of the present invention induced at least a 50% incidence of penile erections in rats at doses of about 0.003 μmol/kg to about 1.0 μmol/kg.

Emesis Model in Ferrets

Male Fitch ferrets (body weights 1.0-1.5 kg) were obtained from Marshall Farms. Ferrets were fasted overnight before experimentation. Apomorphine or a compound of the present invention was administrated subcutaneously; animals were placed individually in observation cages and the drug-induced emesis and signs of nausea were determined (by direct observation) for a period of 90 minutes following drug injection. Nausea was characterized by behaviors such as licking, gagging, backing, head burying, and intense abdominal grooming. Emesis was usually preceded by these behaviors and was characterized by rhythmic abdominal contractions which were associated with vomiting or retching movement.

TABLE 3

Induced Emesis in Rats
for 2-[(4-pyridin-2-ylpiperazin-1-yl)methyl]-1H-benzimidazole

| Dose μmol/kg | Incidence (%) |
| --- | --- |
| vehicle | 0 |
| 0.03 | 0 |
| 0.3 | 0 |
| 3.0 | 0 |

Sterile saline was used as vehicle. Six animals were used per dose. Apomorphine was used as a positive control in Table 3 at a dose of 0.3 μmol/kg which resulted in an 100% incidence of ferrets exhibiting emesis.

As shown in Table 3, 2-[(4-pyridin-2-ylpiperazin-1-yl)methyl]-1H-benzimidazole did not induce emesis in ferrets after subcutaneous administration.

Apomorphine has been included as a positive control in these studies. These data indicate that 2-[(4-pyridin-2-ylpiperazin-1-yl)methyl]-1H-benzimidazole offers a significant advantage over apomorphine, as it facilitates penile erection without inducing emesis.

Compounds of the present invention, in particular 2-[(4-pyridin-2-ylpiperazin-1-yl)methyl]-1H-benzimidazole, can be used in combination with phosphodiesterase 5 inhibitors including, but not limited to, sildenafil or vardenafil as method of treating sexual dysfunction in a mammal.

Compounds of the present invention, in particular 2-[(4-pyridin-2-ylpiperazin-1-yl)methyl]-1H-benzimidazole, can be used in combination with an adrenergic receptor antagonist including, but not limited to, terazosin, prazosin or tamsulosin as method of treating sexual dysfunction in a mammal.

Compounds of the present invention, in particular 2-[(4-pyridin-2-ylpiperazin-1-yl)methyl]-1H-benzimidazole, can be used in combination with a dopamine agonist including, but not limited to, apomorphine as a method of treating sexual dysfunction in a mammal.

Compounds of the present invention, in particular 2-[(4-pyridin-2-ylpiperazin-1-yl)methyl]-1H-benzimidazole, are dopamine agonists and therefore are useful for the treatment of female sexual dysfunction, attention deficit hyperactivity disorder, Alzheimer's disease, drug abuse, Parkinson's disease, anxiety, schizophrenia, mood disorders and depression as described in The dopamine $D_4$ receptor: a controversial therapeutic target. N. J. Hrib. Drugs of the future 25:587-611 (2000); Dopamine and sexual behavior. M. Melis and A. Argiolas. Neuroscience and Biobehavioral Reviews 19:19-38 (1995); and Dopamine receptors: from structure to function. C. Missale, S. R. Nash, S. Robinson, M. Jabber and M. Caron. Physiological Reviews 78: 189-225 (1998).

Compounds of the present invention, in particular 2-[(4-pyridin-2-ylpiperazin-1-yl)methyl]-1H-benzimidazole, are dopamine agonists and therefore are useful for the treatment of cardiovascular disorders. Dopamine and dopaminergic agents have been reported to exert pharmacologically significant cardiovascular effects on blood pressure and heart rate and can be useful in the treatment of cardiovascular disorders (Chen F F, and Lin M T, Effects of dopamine, apomorphine gamma-hydroxybutyric acid, haloperidol, and pimozide on reflex bradycardia in rats, Journal of Pharmacology and Experimental Therapeutics (1980) 214: 427-432), and it has been reported that primate data support the potential clinical utility of dopamine receptor agonists in treating cardiovascular disease (Hahn, R A and MacDonald B R, Primate cardiovascular responses meditated by dopaminine receptors: effects of N,N-dipropyidopamine and LY171555, Journal of Pharmacology and Experimental Therapeutics (1984) 229: 132-138.

Compounds of the present invention, in particular 2-[(4-pyridin-2-ylpiperazin-1-yl)methyl]-1H-benzimidazole, are dopamine agonists and therefore are useful for the treatment of inflammation. Dopaminergic agents can exert anti-inflammatory effects and be useful for the treatment of diseases where inflammation plays a deleterious role (Bendele A M, Spaethe S M, Benslay D N, and Bryant H U, Anti-inflammatory activity of pergolide, a dopamine receptor agonist, in Journal of Pharmacology of Pharmacology and Experimental Therapeutics (1991) 259: 169-175. Dopaminergic agents can also be of utility in the treatment of cancers (Lissoni P, Mandala M, Giani L, Malugani F, Secondino S, Zonato S, Rocco F, Gardani G, Efficacy of Bromocriptine in the Treatment of Metastatic Breast Cancer and Prostate Cancer-related Hyperprolactinemia, Neuroendocrinology Letters (2000) 21:-405-408).

The term agonist, as used herein, refers to a compound that interacts with one or more dopamine receptor subtypes and elicits an observable intracellular biochemical response. The response is measured relative to a full agonist like dopamine.

The term "pharmaceutically acceptable carrier," as used herein, means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The present invention provides for pharmaceutical compositions which comprise compounds of the present invention formulated together with one or more non-toxic pharmaceutically acceptable carriers. The pharmaceutical compositions can be formulated for oral administration in solid or liquid form, for parenteral injection or for rectal administration.

Further included within the scope of the present invention are pharmaceutical compositions comprising one or more dopamine agonists prepared and formulated in combination with one or more non-toxic pharmaceutically acceptable compositions. The pharmaceutical compositions can be formulated for oral administration in solid or liquid form, for parenteral injection or for rectal administration.

The pharmaceutical compositions of this invention can be administered to humans and other mammals orally, sublingually, rectally, parenterally, intracisternally, intraurethrally, intravaginally, intraperitoneally, topically (as by powders, ointments or; drops), bucally or as an oral or nasal spray. The term "parenterally," as used herein, refers to modes of administration which include intravenous, intramuscular, intraperitoneal, subcutaneous, intraarticular injection and infusion.

Preferred administration to humans is oral or sublingual.

Pharmaceutical compositions of this invention for parenteral injection comprise pharmaceutically acceptable sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity may be maintained, for example, by the use of a coating such as lecithin, by the maintenance of the required particle size in the case of dispersions, and by the use of surfactants.

These compositions may also contain adjuvants such as preservative agents, wetting agents, emulsifying agents, and dispersing agents. Prevention of the action of microorganisms may be ensured by various antibacterial and antifungal agents, for example, parabens, chlorobutanol, phenol, sorbic acid, and the like. It may also be desirable to include isotonic agents, for example, sugars, sodium chloride and the like. Prolonged absorption of the injectable pharmaceutical form may be brought about by the use of agents delaying absorption, for example, aluminum monostearate and gelatin.

In some cases, in order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Suspensions, in addition to the active compounds, may contain suspending agents, as, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

If desired, and for more effective distribution, compounds of the present invention can be incorporated into slow-release or targeted-delivery systems such as polymer matrices, liposomes, and microspheres. They may be sterilized, for example, by filtration through a bacteria-retaining filter or by incorporation of sterilizing agents in the form of sterile solid compositions, which may be dissolved in sterile water or some other sterile injectable medium immediately before use.

Compounds of the present invention may also be in micro-encapsulated form, if appropriate, with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound can be admixed with at least one inert diluent such as sucrose, lactose, or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of such composition that they release the active ingredient(s) only, or preferentially, in a certain part of the intestinal tract in a delayed manner. Examples of embedding compositions which can be used include polymeric substances and waxes.

Injectable depot forms are made by forming microencapsulated matrices of the compounds of the present invention in biodegradable polymers such as polylactide-polyglycolide. Depending upon the ratio of compounds of the present invention to polymer and the nature of the particular polymer employed, the rate of compounds of the present invention can be controlled. Examples of other biodegradable polymers include poly(orthoesters) and poly(anhydrides) Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic, parenterally acceptable diluent or solvent such as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Solid dosage forms for oral administration include capsules, tablets, pills, powders, and granules. In such solid dosage forms, a compound or compounds of the present invention are mixed with at least one inert, pharmaceutically acceptable excipient or carrier such as sodium citrate or calcium phosphate and/or a) fillers or extenders such as starches, lactose, sucrose, glucose, mannitol, and silicic acid; b) binders such as carboxymethylcellulose, alginates, gelatin, polyvinylpyrrolidinone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as cetyl alcohol and glycerol monostearate;) absorbents such as kaolin and bentonite clay; and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract in a delayed manner. Examples of embedding compositions which can be used include polymeric substances and waxes.

Liquid dosage forms for oral administration include pharmaceutically acceptable emulsions, microemulsions, solutions, suspensions, syrups and elixirs. In addition to compounds of the present invention, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition compounds of the present invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to compounds of the present invention, excipients such as lactose, talc, silicic acid, aluminum hydroxide, calcium silicates and polyamide powder, or mixtures of these substances. Sprays can additionally contain customary propellants such as chlorofluorohydrocarbons.

Compounds of the present invention can be used in the form of pharmaceutically acceptable salts derived from inorganic or organic acids. By "pharmaceutically acceptable salt" is meant those salts which are, within the scope of sound medical judgement, suitable for use in contact with the tissues of mammals, in particular humans, without undue toxicity, irritation, allergic response and the like and are commensurate with a reasonable benefit/risk ratio. Pharmaceutically acceptable salts are well-known in the art. For example, S. M. Berge et al. describe pharmaceutically acceptable salts in detail in J. Pharmaceutical Sciences, 1977, 66: 1 et seq. The salts can be prepared in situ during the final isolation and purification of the compounds of the invention or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsufonate, digluconate, glycerophosphate, hemisulfate, heptanoate, hexanoate, fumarate, hydrochloride, dihydrochloride, trihydrochloride, hydrobromide, hydroiodide, 2-hydroxyethansulfonate (isethionate), lactate, maleate, methanesulfonate, nicotinate, 2-naphthalenesulfonate, oxalate, pamoate, pectinate, persulfate, 3-phenylpropionate, picrate, pivalate, propionate, succinate, sulfate, bis(tartrate), tartrate, (L) tartrate, bis((L) tartrate), (D) tartrate, bis((L) tartrate), (DL) tartrate, bis((DL) tartrate), meso-tartrate, bis(meso tartrate), thiocyanate, phosphate, glutamate, bicarbonate, p-toluenesulfonate and undecanoate.

Preferred pharmaceutically acceptable salts of the present invention are bis((D)tartrate), bis((DL)tartrate), bis(bromide), bis(sulfate), bis(phosphate), fumarate and tris(hydrochloride).

A most preferred pharmaceutically acceptable salt of the present invention is the bis((L)tartrate).

The term "pharmaceutically acceptable prodrug" or "prodrug," as used herein, represents those prodrugs of compounds of the present invention which are, within the scope of sound medical judgement, suitable for use in contact with the tissues of mammals, in particular humans, without undue toxicity, irritation, allergic response, and the like, commensurate with a reasonable benefit/risk ratio, and effective for their intended use. Prodrugs of compounds of the present invention may be transformed in vivo to compounds of the present invention, for example, by hydrolysis in blood. A thorough discussion is provided in T. Higuchi and V. Stella, Pro-drugs as Novel Delivery Systems, V. 14 of the A.C.S. Symposium Series, and in Edward B. Roche, ed., Bioreversible Carriers in Drug Design, American Pharmaceutical Association and Pergamon Press (1987). For example, compounds of formula (I) substituted at $R_E$ with alkoxycarbonyl, alkyl, alkylcarbonyl, arylcarbonyl, cycloalkylcarbonyl, heterocyclecarbonyl or $(NZ_1Z_2)$carbonyl are prodrugs. In particular, isobutyl 2-[(4-pyridin-2-ylpiperazin-1-yl)methyl]-1H-benzimidazole-1-carboxylate; 2-[(4-pyridin-2-ylpiperazin-1-yl)methyl]-1-(pyrrolidin-1-ylcarbonyl)-1H-benzimidazole; and N,N-dimethyl-2-[(4-pyridin-2-ylpiperazin-1-yl)methyl]-1H-benzimidazole-1-carboxamide are representative examples of prodrugs of compounds of formula (I).

The term "pharmaceutically acceptable ester" or "ester," as used herein, refers to esters of compounds of the present invention which hydrolyze in vivo and include those that break down readily in the human body to leave the parent compound or a salt thereof. Examples of pharmaceutically acceptable, non-toxic esters of the present invention include $C_1$-to-$C_6$ alkyl esters and $C_5$-to-$C_7$ cycloalkyl esters, although $C_1$-to-$C_4$ alkyl esters are preferred. Esters of the compounds of formula (I) may be prepared according to conventional methods.

The term "pharmaceutically acceptable amide" or "amide," as used herein, refers to non-toxic amides of the present invention derived from ammonia, primary $C_1$-to-$C_6$ alkyl amines and secondary $C_1$-to-$C_6$ dialkyl amines. In the case of secondary amines, the amine may also be in the form of a 5- or 6-membered heterocycle containing one nitrogen atom. Amides derived from ammonia, $C_1$-to-$C_3$ alkyl primary amides and $C_1$-to-$C_2$ dialkyl secondary amides are preferred. Amides of the compounds of formula (I) may be prepared according to conventional methods.

Dosage forms for topical administration of compounds of the present invention may include powders, sprays, ointments and inhalants. The active compound is mixed under sterile conditions with a pharmaceutically acceptable carrier and any needed preservatives, buffers or propellants which can be required. Opthalmic formulations, eye ointments, powders and solutions are also contemplated as being within the scope of this invention.

Actual dosage levels of active ingredients in the pharmaceutical compositions of this invention can be varied so as to obtain an amount of the compound or compounds of the present invention which are effective to achieve the desired therapeutic response for a particular patient, compositions and mode of administration. The selected dosage level will depend upon the activity of the particular compound, the route of administration, the severity of the condition being treated and the condition and prior medical history of the patient being treated. However, it is within the skill of the art to start doses of the compounds of the present invention at levels lower than required for to achieve the desired therapeutic effect and to gradually increase the dosage until the desired effect is achieved.

The present invention contemplates compopunds of the present invention either chemically synthesized or formed for example, by administration of a prodrug and subsequent in vivo biotransformation to a compound of the present invention.

When used in the above or other treatments, a therapeutically effective amount of compounds of the present invention can be employed in pure form or, where such forms exist, in pharmaceutically acceptable salt or prodrug form. Alternatively, compounds of the present invention can be administered as a pharmaceutical composition containing a compound or compounds of the present invention in combination with one or more pharmaceutically acceptable excipients. The phrase "therapeutically effective amount" of the compound of the present invention means a sufficient amount of a compound or compounds of the present invention to treat sexual dysfunction, at a reasonable benefit/risk ratio applicable to any medical treatment. It will be understood, however, that the total daily usage of a compound or compounds of the present invention and compositions thereof will be decided by the attending physician within the scope of sound medical judgement. The specific therapeutically effective dose level for any particular patient will depend upon a variety of factors including the sexual dysfunction being treated and the severity of the sexual dysfunction; activity of the compound or compounds of the present invention employed; the specific composition employed; the age, body weight, general health, sex and diet of the patient; the time of administration, route of administration, and rate of excretion of the compound or compounds of the present invention; the duration of the treatment; drugs used in combination or coincidental with a compound or compounds of the present invention; and like factors well known in the medical arts. For example, it is well within the skill of the art to start doses of an agonist at levels lower than required to achieve the desired therapeutic effect and to gradually increase the dosage until the desired effect is achieved.

The total daily dose of compounds of the present invention administered to a human or other mammal may range from about 0.001 to about 30 mg/kg/day. For purposes of oral administration, more preferable doses can be in the range of from about 0.01 to about 10 mg/kg/day. For purposes of sublingual administration, more preferable doses can be in the range of from about 0.001 to about 0.15 mg/kg/day. If desired, the effective daily dose can be divided into multiple doses for purposes of administration; consequently, single dose compositions may contain such amounts or submultiples thereof to make up the daily dose.

What is claimed is:

1. A compound of formula (I)

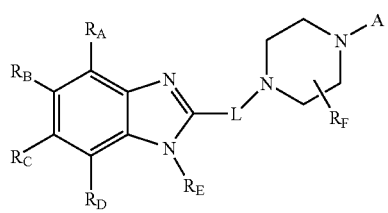

(I)

wherein $R_A$, $R_B$, $R_C$ and $R_D$ are each independently selected from the group consisting of hydrogen and halogen;

$R_F$ and $R_E$ are hydrogen;

L is $CH_2$;

A is

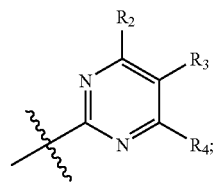

and $R_2$, $R_3$ and $R_4$ are each hydrogen.

2. The compound according to claim 1 that is 2-[(4-pyrimidin-2-ylpiperazin-1-yl)methyl]-1H-benzimidazole.

3. A compound of formula (II)

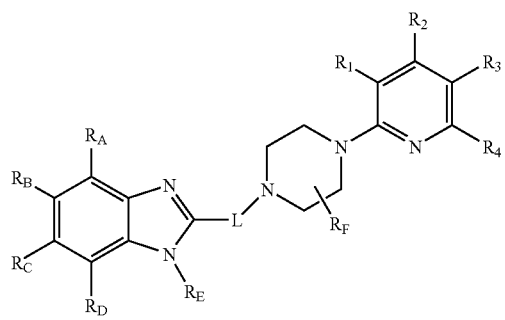

(II)

wherein $R_1$, $R_2$ and $R_4$ are each hydrogen;

$R_3$ is hydroxy;

L is $CH_2$;

$R_A$, $R_B$, $R_C$ and $R_D$ are each independently selected from the group consisting of hydrogen and halogen; and $R_F$ and $R_E$ are hydrogen.

4. The compound according to claim 3 that is 6-[4-(1H-benzimidazol-2-ylmethyl)piperazin-1-yl]pyridin-3-ol.

5. A compound of formula (II)

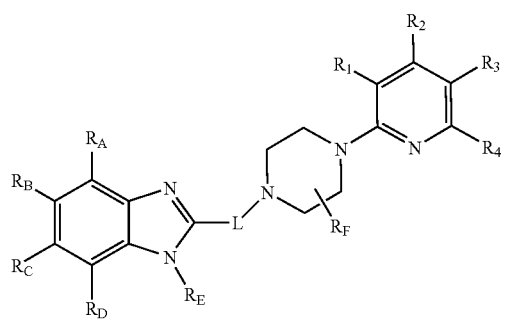

(II)

wherein $R_1$, $R_2$, $R_3$ and $R_4$ are each independently selected from the group consisting of hydrogen and alkylsulfonylamino, provided that at least one of $R_1$, $R_2$, $R_3$, or $R_4$ is other than hydrogen;

L is $CH_2$;

$R_F$ and $R_E$ are hydrogen; and $R_A$, $R_B$, $R_C$ and $R_D$ are each independently selected from the group consisting of hydrogen and halogen.

6. The compound according to claim 5 wherein $R_2$, $R_3$ and $R_4$ are each hydrogen; and $R_1$ is alkylsulfonylamino.

7. The compound according to claim 6 that is N-{2-[4-(1H-benzimidazol-2-ylmethyl)piperazin-1-yl]pyridin-3-yl}methanesulfonamide.

* * * * *